United States Patent
Graham et al.

(10) Patent No.: US 10,466,165 B2
(45) Date of Patent: *Nov. 5, 2019

(54) COMPOUND OPTICAL FLOW CELLS AND METHOD OF MANUFACTURE AND USE

(71) Applicant: Beckman Coulter, Inc., Brea, CA (US)

(72) Inventors: Marshall Donnie Graham, Nicholasville, KY (US); William Gerry Graham, Nicholasville, KY (US); James P. Clarkin, Scottsdale, AZ (US); Mark A. Wells, Davie, FL (US); Jose M. Cano, Miami, FL (US); Carlos Alberto Arboleda, Miami, FL (US); Armando J. Sanchez, Miami, FL (US)

(73) Assignee: Beckman Coulter, Inc., Brea, CA (US)

( * ) Notice: Subject to any disclaimer, the term of this patent is extended or adjusted under 35 U.S.C. 154(b) by 144 days.

This patent is subject to a terminal disclaimer.

(21) Appl. No.: 15/714,473

(22) Filed: Sep. 25, 2017

(65) Prior Publication Data

US 2018/0188154 A1    Jul. 5, 2018

Related U.S. Application Data

(63) Continuation of application No. 14/770,930, filed as application No. PCT/US2014/029460 on Mar. 14, 2014, now Pat. No. 9,772,274.

(Continued)

(51) Int. Cl.
*G01N 21/05* (2006.01)
*C03B 23/047* (2006.01)
(Continued)

(52) U.S. Cl.
CPC .......... *G01N 21/05* (2013.01); *C03B 23/047* (2013.01); *C03C 27/00* (2013.01);
(Continued)

(58) Field of Classification Search
None
See application file for complete search history.

(56) References Cited

U.S. PATENT DOCUMENTS 2,656,508 A   10/1953   Coulter
3,380,584 A   4/1968   Fulwyler
(Continued)

FOREIGN PATENT DOCUMENTS

JP    62168033 A    7/1987
WO    2014144868 A1    9/2014

OTHER PUBLICATIONS

Johnson, et al.; "Modification of a Laser-Based Flow Cytometer for High-Resolution DNA Analysis of Mammalian Spermatozoa", Cytometry 7, May 1986 pp. 268-27.

(Continued)

*Primary Examiner* — Hina F Ayub
*Assistant Examiner* — Amanda Merlino
(74) *Attorney, Agent, or Firm* — Schwegman Lundberg & Woessner, P.A.

(57) ABSTRACT

An improved optical flow cell adapted for use in a flow cytometer for differentiating formed bodies (e.g., blood cells) in liquid suspensions. Preferably manufactured by assembling, aligning, and optically joining at least two elements made from transparent material, the improved flow cell has a seamless internal flow channel of preferably non-circular cross-section in a cylindrical first element through which prepared samples can be metered and an independent second element having an external envelope suited to acquisition of optical parameters from formed bodies in such suspensions, the second element being conforming and alignable to the first element so that non-axisymmetric refractive effects on optical characterizing parameters of formed bodies passing through the flow channel in the first element may be minimized before the (Continued)

two elements are optically joined and fixed in working spatial relationship.

18 Claims, 17 Drawing Sheets

Related U.S. Application Data

(60) Provisional application No. 61/792,802, filed on Mar. 15, 2013.

(51) Int. Cl.
*G01N 15/14* (2006.01)
*C03C 27/00* (2006.01)
*G01N 15/10* (2006.01)

(52) U.S. Cl.
CPC . *G01N 15/1434* (2013.01); *G01N 2015/1006* (2013.01); *G01N 2015/149* (2013.01); *G01N 2015/1452* (2013.01); *G01N 2015/1486* (2013.01); *G01N 2201/02* (2013.01); *Y02P 40/57* (2015.11)

(56) References Cited

U.S. PATENT DOCUMENTS

| | | | |
|---|---|---|---|
| 3,502,974 A | 3/1970 | Coulter et al. | |
| 4,348,107 A | 9/1982 | Leif | |
| 4,673,288 A | 6/1987 | Thomas et al. | |
| 4,818,103 A | 4/1989 | Thomas et al. | |
| 5,088,816 A | 2/1992 | Tomioka et al. | |
| 5,125,737 A * | 6/1992 | Rodriguez | G01N 15/1459 356/338 |
| 5,412,466 A | 5/1995 | Ogino | |
| 5,690,895 A | 11/1997 | Matsumoto et al. | |
| 5,825,477 A | 10/1998 | Furuie | |
| 6,228,652 B1 | 5/2001 | Rodriguez et al. | |
| 8,189,187 B2 | 5/2012 | Graham et al. | |
| 9,772,274 B2 | 9/2017 | Graham et al. | |
| 2004/0086216 A1 | 5/2004 | Elster et al. | |
| 2005/0180885 A1 | 8/2005 | Tateishi et al. | |
| 2007/0085997 A1 | 4/2007 | Thomas | |
| 2010/0118298 A1 | 5/2010 | Bair et al. | |
| 2016/0011098 A1 | 1/2016 | Graham et al. | |

OTHER PUBLICATIONS

Kachel, et al., "Uniform Lateral Orientation, Caused by Flow Forces, of Flat Particles in Flow-Through Systems", Journal of Histochemistry and Cytochemisty, 25, Jul. 1977, pp. 774-780.

Leif, et al., "Optical analysis of the AMAC IIIS transducer", Applied Optics, vol. 26, No. 16, Aug. 15, 2987, pp. 3244-3248.

Leif, et al., "Use of a Spherical Multiparameter Transducer for Flow Cytometry", Cytometry 20, Jun. 1995, pp. 185-190.

Pinkel, et al., "Flow Cytometry of Mammalian Sperm Progress in DNS and Morphology Measurement", The journal of Histochemistry and Cytochemistry, vol. 27, Issue. 1, Jan. 1979, pp. 356-358.

Stovel, et al., "A Means for Orienting Flat Cells in Flow Systems", Biophysics Journal, vol. 23, Issue 1, Jul. 1978, pp. 1-5.

International Search Report and Written Opinion of related PCT/US2014/029460, dated Jul. 17, 2014, all pages.

* cited by examiner

COMPOUND OPTICAL FLOW CELLS AND METHOD OF MANUFACTURE AND USE

CROSS-REFERENCES TO RELATED APPLICATIONS

This application is a continuation of U.S. patent application Ser. No. 14/770,930 filed on Mar. 14, 2014, (which will issue as U.S. Pat. No. 9,772,274 on Sep. 26, 2017), which is a U.S. National Stage Entry under § 371 of International Application No. PCT/US2014/029460, filed Mar. 14, 2014, which claims the benefit of priority to U.S. Provisional Patent Application No. 61/792,802 filed Mar. 15, 2013. This application is also related to U.S. Pat. No. 8,189,187. The entire content of each of the above filings is incorporated herein by reference for all purposes.

BACKGROUND OF THE INVENTION

Embodiments of the present invention relate generally to apparatus and methods for differentiating constituent types of formed bodies (e.g., cells or other small particles) in liquid samples (e.g., whole blood or other particle-suspending liquids). More particularly, embodiments relate to improvements in transducer assemblies for use in hematology analyzers and other flow cytometers that function to sense, characterize, and differentiate formed bodies in such samples by various optical parameters, often in combination with non-optical parameters acquired via the Coulter Principle. Embodiments of the invention further relate to improvements in optical flow cells used in such transducer assemblies and to improvements in methods for sensing characterizing parameters from formed bodies transiting the parameter-acquisition portion of such flow cells.

The analyses of patient body fluids can be automated as an aid in diagnosing a patient's state of health. Such analyses can include flowing a prepared portion of such body fluids through a transducer assembly to derive certain parameters characteristic of the several different types or subpopulations of constituent formed bodies therein, differentiating and enumerating the several types or subpopulations of the formed bodies on the basis of the derived parameters, and processing or correlating the resultant information to provide desired diagnostics. For example, these tasks can be accomplished for whole blood via characterization of blood cells therein by automated hematology analyzers and flow cytometers.

A fundamental performance limit of some current instruments of the type noted above originates in the transduction of formed-body properties into the characterizing parameters used to assign individual formed bodies to specific subpopulations. For many applications, optical transductive methods alone provide effective means for characterizing formed bodies. In these applications, a portion of a prepared sample is interrogated with optical radiation as it flows through a passageway formed in an optically transparent element, or flow cell, forming a portion of a transducer module. Suitable photo-detectors, also forming part of the module, are positioned to detect various optical parameters from an irradiated formed body including, for example, its optical absorbance of the interrogating beam, its fluorescence at different wavelengths, and its light-scattering effect within one or more angular ranges. In these optical-only applications, it will be appreciated that the physical extent of the flow-cell passageway can be relatively large without adversely affecting the determination of these optical parameters. However, in other cytometric applications where such optical parameters are combined with simultaneously determined non-optical parameters, in particular those based on the Coulter Principle (discussed below), both the cross-section and at least a length of a portion of the flow-cell passageway may need to be dramatically restricted to achieve suitable signal strength.

Due to the limitations of then-existing optical sensing methods, W. H. Coulter devised an electronic method for characterizing minute formed bodies suspended in a liquid. The now-familiar Coulter Principle enables determination of the volume of formed bodies, by flowing a sample portion prepared in an electrically conductive liquid through a particle-sensing zone (or volumeter conduit) simultaneously with an electric current. The electrical resistivity of the particle-suspending liquid differs from that of the particles, the electrical contrast permitting counting and sizing of particles transiting the volumeter conduit. Although other geometries were discussed in Coulter's U.S. Pat. No. 2,656,508, volumeter conduits are usually cylindrical bores in a thin insulative wafer, the conduit's cross-sectional area and length determining volumetric sensitivity, coincidence volume, and maximum passable formed-body dimension; thus, conduit diameters are typically at most an order of magnitude greater than the diameter of the typical formed bodies to be analyzed. The volumeter conduit forms the only fluidic communication between two insulative chambers of the transducer assembly, with no requirement on the optical characteristics of the wafer material surrounding the conduit. Initially, a direct current (DC) was provided through the conduit, and resistive Coulter volume (V) signals proportional to the volume of transiting formed bodies were acquired via electrodes positioned outside the opposite ends of the volumeter conduit. In U.S. Pat. No. 3,380,584 differences in the Coulter V signals were adapted to sort subpopulations of such formed bodies to separate collection sites. In U.S. Pat. No. 3,502,974 to W. H. Coulter and W. R. Hogg, the excitation current through the conduit was made to include at least one alternating current (AC), thereby permitting determination of not only the resistive but also reactive components of the conduit current resulting from its modulation by passage of a formed body. When such currents include one having a frequency in the radio-frequency (RF) range (e.g., 22.5 MHz), the respective components permit estimation of the volume (V) and electrical conductivity (C) of a formed body, and the ratio of the reactive to resistive components is said to be the "opacity" of the formed body.

In commonly assigned U.S. Pat. No. 5,125,737 to C. M. Rodriguez and W. H. Coulter (hereinafter, the '737 patent) the Coulter V and C parameters are combined with optical scatter (S) parameters. In certain hematology analyzers incorporating this VCS technology, a diluted blood sample is passed through a cytometric transducer assembly that includes an optical flow cell made from a short segment of optically transparent cylindrical tubing. It is known in the glass-working art to draw tubing from a larger preform of various inner and outer diameters and having a cylindrical wall up to several centimeters thick. During the drawing operation, the preform is heated to a predetermined temperature at which its viscosity permits deformation, whereupon it is drawn axially, usually in a vertically downward direction, at a constant and predetermined rate. During this process the diameters of the inner and outer cross-sections of the preform are substantially reduced with the original circular shapes being substantially retained, such shapes being the minimum energy shape, and the wall of the preform is significantly reduced in thickness. This drawing process has been adapted to form thick-wall transparent tubing for use in producing seamless single-piece (monolithic) flow cells such as described in the '737 patent. After a preform is drawn to a preferred inner diameter (e.g., 50 micra), the tubing is cut into segments of a preferred length (e.g., about 6 mm), and a suitable flat (e.g., 1 mm wide) is lapped and polished on the exterior cylindrical surface of the segments which, as a result of the drawing, has been reduced to a diameter of about 3.5 mm. The flat provides an optical port through which a radiation beam (e.g., from a HeNe laser) can be coupled, substantially perpendicular thereto and along a diameter, to the central cylindrical channel in the drawn tube. The flat is made substantially parallel to the channel axis at an arbitrary location on the outer cylindrical surface, e.g., to avoid or eliminate an objectionable optical defect in the segment wall. The cylindrical channel is partially enlarged by boring a segment from both ends to a suitable diameter (e.g., about 1.2 mm), leaving in situ a short length (e.g., about 65 micra) of the original channel in the middle of the flow cell that opens at each end into a cup-shaped recess (e.g., of radius about 600 micra) substantially coaxial with the original channel and continuous with the end bores. In use, the length of the original channel in the longitudinal section thus formed functions as a Coulter volumeter conduit, and the cylindrical bores of the resulting passageway communicate with external electrode chambers in said transducer assembly, whereby the sample liquid in a hydrodynamically-focusing sheath liquid can be made to pass centrally through the volumeter conduit. Coulter V and C parameters are acquired from electrodes as described in aforesaid U.S. Pat. Nos. 2,656,508 and 3,502,974 as formed bodies pass through the volumeter conduit; meanwhile, optical scatter (S) parameters from the radiation beam are simultaneously acquired from the individual formed bodies as they pass seriatim through said beam traversing the parameter sensing zone formed by the cylindrical volumeter conduit.

In certain hematology analyzers, the repeatable circular cross-section of the flow-cell volumeter conduit is of designed dimension, and the flatted cylindrical surface forming the envelope of the '737 flow cell is substantially parallel to the axis of the conduit. The incoming radiation beam is brought through the flat to a minimum cross-sectional area within the circular volumeter conduit. Light from the beam is scattered by passing nucleated cells in the sample, and photo-detectors suitably positioned near the optical axis detect the forward-scattered radiation within specific angular bands, thereby allowing the aforesaid S parameters to be developed. Such forward-scatter (FS) signals acquired through the wall of such flow cells permit reliable enumeration, differentiation, and classification of normal individual leukocytes into monocytes, lymphocytes, neutrophils, eosinophils, and basophils when appropriately correlated with Coulter V and C parameters. These diagnostic data have a proven history of clinical usefulness.

At interfaces between dissimilar transparent materials an incident radiation ray of wavelength $\lambda$, the normal to the interfacial tangent at the point of the ray's incidence, and the ray emerging from the interface are all co-planar. The ray paths follow Snell's Law, $n_1(\lambda) \sin \theta_1 = n_2(\lambda) \sin \theta_2$, where $\theta_1$ and $\theta_2$ are the respective angles at which a ray is incident on the interface and emerges from it, both with respect to said normal, and $n_1(\lambda)$ and $n_2(\lambda)$ are the refractive indices on the incident and exit sides of the interface. Its low refractive index $[n(\lambda) \approx 1.457]$ led to fused silica ($SiO_2$) being preferred for use in aforesaid '737 flow cells. For typical suspending liquids the refractive index is about 1.333, while that of air is 1.000. For any wall geometry in fused silica and $\sin \theta_2$ less than unity, rays originating near the flow-cell axis will be refracted toward the surface normal at their incidence on the conduit surface ($\sin \theta_2 \approx 0.915 \sin \theta_1$) but away from it at their incidence on the envelope surface ($\sin \theta_2 \approx 1.457 \sin \theta_1$). Scattered radiation propagating from formed bodies within the '737 volumeter conduit to the relevant photodetectors passes through suspending liquid in contact with the cylindrical conduit surface and the cylindrical envelope surface in contact with ambient air, the cylindrical wall between said surfaces thus being a non-axisymmetric refractive element. For rays originating on the axis of '737 flow cells and exiting the volumeter conduit in the plane including the optical axis of the incoming radiation beam, $\theta_1 = \theta_2 = 0$, and such rays pass through both surfaces of the flow-cell wall without significant refraction. However, if $n_1(\lambda) \neq n_2(\lambda)$ such rays propagating at any angle $\theta$ to said plane will be refracted at both wall surfaces, the refractive deviation from the path of incidence increasing with the combined effects of $\theta$ and the mismatch between $n_1(\lambda)$ and $n_2(\lambda)$ with the refraction being symmetric about said plane. Thus, a circular cone of rays exiting through the flow-cell wall from an origin at the intersection of the optical and conduit axes will be asymmetrically refracted, with refractive deviation ranging from zero where said plane intersects either the conduit or envelope surface to total internal reflection at the envelope surface if $\theta_1$ makes $1.457 \sin \theta_1 \geq 1$. Due to these non-axisymmetric refractive effects, scattered radiation passing through the flow-cell wall acquires substantial astigmatism that, affecting scatter from small objects more than that from larger objects, affects the ability to differentiate formed bodies characterized by granular structure. Parallel planar wall surfaces minimize such asymmetric refractive effects, and such a cone of rays experiences uniform refraction about the optical axis of the radiation beam as determined by the angle of incidence and the difference between $n_1(\lambda)$ and $n_2(\lambda)$ across both wall surfaces. Such walls improve acquisition of not only S but other optical signals, and extensive effort has been directed toward flow cells having a prismatic channel surrounded by planar walls, e.g., a modified embodiment in the '737 patent incorporates a flow cell that includes a square volumeter conduit within a similar envelope.

In commonly assigned U.S. Pat. No. 6,228,652 to C. M. Rodriguez et al. (hereinafter, the '652 patent), experimental apparatus is disclosed that can provide simultaneous acquisition of various optical, Coulter V, and Coulter C signals from an individual formed body, with subsequent differentiation of formed-body subpopulations in whole blood based thereon. One of the square flow-cell structures illustrated in the '737 patent is the preferred flow cell in the '652 patent and is discussed regarding FIG. 3 therein. This flow cell comprises an optically transparent element having a prismatic exterior envelope of square cross-section, measuring about 4.2 mm on each side, and having a length of about 6.3 mm. (As used hereinafter, the word "prismatic" refers to any three-dimensional figure composed of three or more intersecting sides that are planar, and a pair of opposing ends that are polygonal in shape. Hereinafter, "polygonal" is used to refer to any closed plane figure having at least three substantially straight sides, and "planar" as used herein refers to a surface having an area that is predominantly flat.) Centrally located within said prismatic element is a prismatic volumeter conduit having a square cross-section about 50 micra on each side and a length of about 65 micra; the relatively small cross-section and length of the conduit are necessary to attain a reasonable volumetric sensitivity and coincidence volume for acquiring said V and C signals. Thus, the ratio of the respective cross-sectional areas of said conduit and envelope is approximately 0.00014, and the wall thickness is about 2.075 mm. To acceptably limit aberrational content of optical signals, surfaces of the prismatic envelope and conduit should be substantially parallel, with optical planarity. This combination of square/square cross-sectional geometries, wall thickness, wall surface parallelism, and wall flatness is difficult to achieve, a difficulty compounded by the small dimensions required for volumeter conduits.

To manufacture flow cells of the type preferred in the '652 patent, a relatively complex planarization process has been used wherein four transparent plates, e.g., preferably made of a form of silica, are polished to predetermined thickness and finish and assembled to form the composite structure of FIG. 1. During assembly, a pair of said plates CC1 and CC3 is spaced apart by the other pair CC2 and CC4 to form two walls of flow cell 20, with the pair of equal-thickness spacer plates appropriately spaced apart a predetermined distance so that their opposing edges complete an internal channel 22. Preferably, complementary elements CC1-CC4 are of appropriate dimensions and joined at their interfaces by fusion to form a prismatic rod having an internal, longitudinally-extending, straight channel 22 of a desired uniform square cross-section therein. This rod is then cut to a desired length, e.g., 6.3 mm, and the segments polished to the desired external geometry and dimensions to form a flow cell having a prismatic envelope, e.g., opposing planar sides 50 in FIG. 1 having a flat-to-flat separation of 4.2 mm. Such composite optical flow cells having prismatic flow channels of constant longitudinal section but various square cross-sections have been made by varying the thickness and separation of the two spacer plates CC2 and CC4. For acquisition of Coulter parameters, a passageway including a prismatic volumeter conduit, e.g., the 50 micra by 50 micra square conduit described above, is formed in such flow cells by boring square channel 22 from both ends as described above for the '737 flow cell to form a parameter-acquisition zone. The longitudinal section of said passageway is such that the sample liquid in a hydrodynamically-focusing sheath liquid passes centrally through the square volumeter conduit thus formed within the flow cell. Spacer plates may also be separated by a spacing differing from their thickness, to form flow channels having rectangular cross-sections as in U.S. Pat. No. 4,786,165. Various embodiments of flow cells made by the planarization process have been adapted to function in certain flow cytometers. Flow cells suited to application in such instruments and made by the method of the present invention are illustrated in respective FIGS. 7A, 7B, 12, and 14 and will be discussed as embodiments of the present invention.

Although useful flow cells of the type preferred in the '652 patent have been produced by the above-described planarization process, the yield of such flow cells processed to include a volumeter conduit is very low, typically less than 1 in 3, due to weakness in the fused joins. For formed bodies transiting the internal volumeter conduit of useful flow cells (e.g., BC2 in FIG. 1), optical signals acquired through the two windows may be substantially repeatable (e.g., the forward-scatter signals FS resulting from a sensor placed outside window CC1 and on the optical axis OA opposite the entry window CC3 for radiation beam B in FIG. 1). However, those acquired through the two walls of flow cell 20 containing spacer plates (e.g., side-scatter signal SS acquired through CC2 and fluorescence signal F acquired through CC4 in FIG. 1) demonstrate both sensitivity to excitation beam position in individual cases and unit-to-unit variability in the resulting optical signals, even though joins are systematically positioned relative to the axis of optical excitation. And because liquid flows and Coulter excitation currents through the flow-cell passageway contact the exposed assembly joins, flow cells made by the planarization process (e.g., flow cell 20 in FIG. 1) are also prone to subsequent failure modes: Firstly, irregularities and air pockets in the fused joins characteristic of the planarization method result in localized heating due to the RF component of the conduit excitation current, with consequent failure of the join; secondly, join imperfections tend to enlarge when sample flows are accompanied by significant cyclic pressure; and finally, flow cells left in stored apparatus tend to separate along the joins due to crystallization of salts if residual reagents are allowed to evaporate.

More-complex production processes, wherein various transparent solids of predetermined geometry are appropriately assembled, have also been used to make composite optical flow cells having prismatic volumeter conduits of a desired geometry and dimensions. If the flow-cell wall were to consist of a spherical envelope containing a concentric spherical cavity, a cone of rays originating at the intersection of the optical and conduit axes would be propagated with no refraction; a flow-cell wall including a spherical envelope centered on the axis of the volumeter conduit enables propagation of scattered radiation with minimal wall-induced refractive aberrations to the extent that $n_1(\lambda)$ approximates $n_2(\lambda)$ at the surface of the conduit. Thus, commonly assigned U.S. Pat. No. 4,348,107 (hereinafter, the '107 patent) discloses optical flow cells in which a volumeter conduit having a preferably square cross-section is contained within an envelope having an exterior spherical surface or other surface of revolution. (Flow cells having such envelope, but made by method embodiments of the present invention, are illustrated in FIG. 13A-13C and will be discussed as embodiments of the present invention.) As illustrated in the '107 patent, such flow cells are made by joining together four complementary, truncated, square-based pyramids formed of a transparent material. The apex is polished from each pyramid parallel to its base and to a depth calculated to yield one side of the desired volumeter conduit, and the pyramids then appropriately assembled and adhesively joined together so that the truncated apexes form an unobstructed square prismatic conduit, the adjacent faces of the joined pyramids forming a tapering longitudinal section at one or both ends of the conduit. Although optical signals may be acquired through the planar surfaces of the resulting prismatic envelope, it is preferred that means unspecified in the '107 patent then provide the flow cell an envelope formed as a surface of revolution. An extension allowing coupling of the sample liquid and a hydrodynamically-focusing sheath liquid through the conduit is sealed to the resulting flow cell where its surface is intersected by one or both of the approaches formed by the exposed sides of the four pyramids. The '107 patent notes that optical and mechanical characteristics of said structure proved suboptimal, the adhesive joins potentially fluorescing or separating, but provides no alternative joining method. A theoretical comparison, of the optical properties of the idealized '107 flow-cell structure with those of a flow cell having a square cross-section in a square prismatic envelope, was published in *Applied Optics* (26:3244-3248, 1987) by the inventor and one of the present co-inventors; no method for production of either flow-cell structure was described. The inventor and other co-workers later verified some of those theoretical predictions in a comparison (*Cytometry* 20:185-190, 1995)

of an embodiment of the '107 flow cell, one having the four pyramids fused together and thus avoiding said problems of adhesive joins, to a monolithic cylindrical flow cell as discussed above regarding certain hematology analyzers incorporating VCS technology; FIG. 2 in said publication shows the '107 flow cell sealed, after production of a polished spherical exterior envelope, between extensions of the plastic chambers housing electrodes enabling acquisition of Coulter V and C signals. As disclosed in U.S. Pat. Nos. 4,673,288 and 4,818,103, variations of the approach disclosed in the '107 patent have been used to provide prismatic volumeter conduits having a triangular cross-section in a similarly shaped envelope, with square, five-sided, etc., structures said to be within the scope of the invention. To allow efficient collection by a microscope objective of optical signals from such triangular volumeter conduits, in U.S. Patent Application 2007/0085997 a thin transparent plate (window) is substituted for one of the truncated pyramids, with the envelope completed by the remaining two complementary components modified to facilitate interrogation of formed bodies by optical radiation through their walls. As will be appreciated, multiple joins, exposed to conduit contents and subject to the disadvantages described above for the planarization process, are required in such composite flow cells comprising a plurality of such fused elements. Further, tolerances in machining apexes from multiple elements, in assembly of the elements, and in joining them to form a volumeter conduit combine to produce variable conduit geometry and dimensions, making this approach both costly and unattractive as a production process and one yielding unit-to-unit variability in the result.

Other disadvantages originate in imperfections in the exposed joins used to assemble prior-art composite flow cells such as described in the '652 patent or in U.S. Patent Application 2007/0085997 and its precursors. Such joins have been made via adhesive processes, low-temperature glass-bonding processes using chemical agents or solder glasses, or high-temperature fusion processes in which surfaces of the complementary components to be joined are placed in close proximity and heated sufficiently to cause those surfaces to soften and bond to each other. Joins formed by the first two methods are significantly less durable than those formed by fusion of the complementary components and may result in background fluorescence that interferes with the weak fluorescent radiation emitted by formed bodies transiting the resulting parameter-acquisition zone; in addition, bonding agents may extend or leave a residue beyond the machined surfaces intended to define corner geometry of the sensing zone and thus cause unpredictable unit-to-unit variability in liquid flow through the zone. Alternatively, insufficient bonding agent may inadequately fill the gap between adjacent components of the composite flow cell, leaving a void extending between such components along the length of the corner these components were intended to form. Viscous forces acting on adjacent surfaces of non-cylindrical flow channels combine such that fluid flows near the corners experience additional resistance, and so slower flow velocities, than near the mid-portions of the surfaces. Consequently, formed bodies outside near-axial flow in non-cylindrical channels experience lower flow rates and may migrate into the corners of such flow channels (e.g., during flow transitions required for flushing of one sample from, and introduction of a different sample into, the transducer assembly). Due to the small dimensions of volumeter conduits and potential issues related to thoroughly flushing them, certain challenges may arise when Coulter V and/or C parameters are acquired and involve additional complexity in practical instrumentation. Typical formed bodies are at most several micra in dimension and thus can be sequestered in such interstices in imperfect joins during such transitions. On resumption of continuous flow the viscosity-induced low flow rates near channel corners may be insufficient to sweep all such sequestered cells out, allowing the potential carry-over of formed bodies from one sample into a subsequent sample. If such a sequestered formed body were of the rare cell types critical to diagnosis, it would not only be absent from the first sample, but could occur in a following normal sample. Misleading diagnostic information could result from the subsequent processing of parameters acquired from both samples as a result of carryover of formed bodies from one patient sample into another patient sample. Because of the difficulty in flushing the small volumeter conduits required for sensing Coulter V and/or C parameters, instrumentation using prior-art composite flow cells including fusion joins is subject to the latter fault and its implications as well. It was noted above regarding the monolithic cylindrical flow cells that these were readily formed because the channel shape was the minimum-energy shape for the glass when softened for drawing. Minimum-energy considerations also apply during fusion-joining of complementary components and result in rounding of the intersection of the surfaces to be joined and the surfaces intended to form the non-cylindrical flow channel. Thus, for example, in flow cells such as used in the experimental instrumentation described in the '652 patent (i.e., flow cell 20 in FIG. 1), the edges of the two spacer plates soften and round over about a center within the spacer plates before the bulk glass softens sufficiently to bond the surfaces to be joined; such rounding is indicated for one such edge of CC4 by R' in FIG. 1, but applies to both such edges of spacer plates CC2 and CC4. As indicated in FIG. 1, the cross-section of resulting channel 22 is not truly rectilinear, but rather has imposed at said four corners interstices adjacent to the two window plates CC1 and CC3 and extending back from the intended corner for several micra. Interstices extending more than 15 micra away from the flow channel and along much of the channel length have been observed in commercial planarized flow cells used during development of said '652 instrumentation; these have a perceptible radius of several micra at both corners of both spacer plates CC2 and CC4. Such join interstices are subject to the aforesaid risk for carryover of formed bodies, with attendant regulatory and liability concerns.

Requiring no joins, truly monolithic flow cells made from a single piece of transparent material, e.g., flow cells of the aforesaid '737 construction, surround the liquid flows and any Coulter excitation currents with a joinless homogeneous wall and so can avoid the limitations and disadvantages described above for certain flow cells comprising joined components of complementary geometries. The single-piece design of such flow cells yields a robust sensing element providing both controlled geometry and dimensions in the flow channel and reliable function in service. When used in data acquisition as described in the '737 patent, forward-scatter (FS) signals acquired from such flow cells permit reliable differentiation and enumeration of individual formed bodies when suitably correlated with Coulter V and C signals. But as discussed above, due to the necessarily small diameters of their circular volumeter conduits, the wall of the '737 flow cells acts as a non-axisymmetric refractive element, with greater refraction for scatter from small objects than for larger objects, and scatter (S) signals acquired through it incur substantial astigmatism that limit the ability to differentiate between certain types of formed bodies. While such differentiation can be improved by adding fluorescence (F) signals at different wavelengths as in the '652 patent, e.g., by selectively tagging the formed bodies with fluorescent dyes or dye-bead conjugates, dispersion due to n(λ) causes F signals to be even more disadvantageously affected by wall-induced refractive artifacts than are scatter signals. Composite flow cells having a prismatic parameter-acquisition zone enclosed by planar wall surfaces (e.g., the square volumeter conduit disclosed in the '652 patent or the triangular volumeter conduit disclosed in U.S. Patent Application 2007/0085997 and its precursors) can also minimize dispersion effects. As noted, however, such flow cells are difficult to make by conventional production methods; exposed joins required for assembly not only introduce optical inhomogeneities, but have the potential in service for both carry-over of formed bodies between samples and failure over time.

A recurring cytometric need is to simultaneously acquire several different types of optical signals resulting from interaction of the formed bodies with one or more radiation sources, i.e., some combination of axial light-loss (ALL) signals; scatter (S) signals such as forward-scatter (FS), side-scatter (SS), or back-scatter (BS) signals; and multiple-wavelength fluorescence (F) signals. In such applications the three or four envelope surfaces on certain flow cells (i.e., those described in respective U.S. Patent Application 2007/0085997 and its precursors or the '652 patent) require that a plurality of sensors view the parameter-acquisition zone through complex beam-splitting and/or wavelength differentiating optics which, in addition to adding cost, introduce alignment and other optical difficulties. The need for more optical sensing paths might be addressed by adding planar surfaces to the flow-cell envelope (i.e., as illustrated in Japanese Unexamined Patent Application No. 62-168033) whereby the envelope could have a pentagonal, hexagonal, heptagonal, etc., cross-section, so that each optical measurement of interest could be made through a separate surface of the envelope. As implicit in discussion above of Snell's Law, such flow cells having a polygonal envelope and a cylindrical parameter-acquisition zone can reduce asymmetric refractive effects below those experienced with flow cells in which both envelope and sensing zone have cylindrical surfaces. Experimental flow cells, made by forming additional planar surfaces in appropriate spatial relation to the optical port lapped onto the drawn '737 flow cell, were found to reduce asymmetric refractive effects for some optical characterizing parameters acquired through said surfaces but, due to the cylindrical surface of the small-diameter sensing zone, not sufficiently for desired acquisition of other such parameters. In addition, further unit-to-unit variability in optical performance resulted from difficulty in aligning such planar surfaces with the drawn flow channel. Conversely, if the flow channel were made to comprise planar surfaces by assembly of complementary components, the manufacture of such composite flow cells would be impractically complex, time-consuming, and costly for commercial incorporation into cytometric instruments, and optically inhomogeneous joins may constrain such designs by incursion on a desired pattern of light collection. Further, reliability and liability implications would result during service, due to the aforesaid contact of the joins by the operational contents of the flow channel.

U.S. Pat. No. 8,189,187 to Graham et. al., (hereinafter, the '187 patent) discloses various embodiments and applications of monolithic optical flow cells formed from a prismatic flow cell, i.e., a monolithic structure made of silicon dioxide by glass-forming methods and having a through channel formed during that process suitable for containing cells in a fluid stream, said channel being defined by at least three substantially planar surfaces and of sufficient length as to permit measurement of cell characteristics by cytometric methods. Such prismatic flow cells are purchased having an as-drawn substantially cylindrical envelope coaxial with the prismatic through-channel, only said through-channel and a thicker wall distinguishing them geometrically from the aforesaid thick-wall transparent tubing used in producing monolithic flow cells as described regarding the '737 patent. To avoid the non-axisymmetric refraction inherent to such cylindrical envelopes, after receipt such prismatic flow cells are improved by providing them, via secondary machining processes, with an integral non-cylindrical envelope, thereby producing the monolithic optical flow cells of the '187 patent. Such monolithic flow cells comprising an envelope of square cross-section coaxial and parallel with a portion of prismatic interior channel of similar cross-section (i.e., a version of flow cell 20' in FIG. 2) are used, according to other teachings of the '187 patent. Within the Coulter volumeter conduit Z so formed, Coulter V and C parameters as well as optical forward-scatter (FS) signals at multiple angles and axial light-loss (ALL) signals are acquired without the aforesaid functional limitations inherent in prior-art composite flow cells such as illustrated in the '737 patent and described in the '652 patent (e.g., flow cell 20 in FIG. 1) or disclosed in U.S. Patent Application 2007/0085997 and its several precursors. These cytometric characterization parameters enable improved discrimination of formed bodies, and the clinical value of diagnostics provided by these analyzers is now recognized. Further, the optical multi-port capability of Japanese Unexamined Patent Application No. 62-168033 is provided without the non-axisymmetric refraction inherent to its cylindrical flow channels. It has been found, however, that potential optical variability arising in the fabrication methods for monolithic flow cells may require selection of the resulting product at an advanced processing stage and so may limit the functional yield of flow cells that provide acceptable optical characterization parameters.

Prismatic flow cells are made via glass-forming methods, more fully described in the '187 patent, in which a relatively large cylindrical glass preform having an oversize internal prismatic channel of a desired polygonal cross-section is heated to a predetermined temperature at which its viscosity permits deformation and drawn axially on a conventional drawing tower to reduce the channel to a desired cross-sectional area. The necessary preform wall thickness is attained by sliding over, heating to cause a viscosity permitting deformation, collapsing onto, and fusing to a first silica tube, caused to have the desired channel cross-section by heating to cause a viscosity permitting deformation and collapsing said tube onto a mandrel having the desired channel geometry, a second larger cylindrical tube of appropriate inner and outer diameters (a sleeve tube) so as to seamlessly increase the wall thickness of the preform. Such oversleeving step is repeated with additional sleeve tubes of appropriate increasing inner and outer diameters until the preform wall thickness will provide a desired flow-cell wall thickness after the preform is drawn to yield the desired channel cross-sectional area and the drawn preform is machined to yield the desired envelope of a monolithic flow cell. Each of the aforesaid several tubes is preferably a form of silica ($SiO_2$), most preferably synthetic amorphous silica, and each of the several heat cycles produces a viscosity in the range between $60 \times 10^6$ and $1 \times 10^6$ poise, more preferably between $28 \times 10^6$ and $3 \times 10^6$ poise. Such oversleeving process may result in a reduced yield of functional flow cells via four potential artifacts that may arise in one or more of the oversleeving cycles: a) air bubbles may be entrapped between the growing preform and the next sleeve tube, subsequently being drawn into air lines in a wall between the flow channel and an envelope surface (e.g., respectively Z and 50 in FIG. 2) of a finished flow cell that may interfere with acquisition of optical parameters; b) concentricity of the successive outer surfaces of the growing preform with the channel axis may be lost, whereby optical paths originating at the intersection of the channel and optical axes encounter refractive profiles through the wall of a finished flow cell that depend upon their angle with respect to the optical axis; c) the growing preform may soften sufficiently that wall surfaces of the internal flow channel (e.g., Z in FIG. 2) lose necessary flatness, thereby causing sub-wavelength random differences in optical path length through a finished wall that may produce limiting refractive and dispersive effects in acquired optical parameters; and d) the effective brittleness of the preform may increase, with increased tendency to chipping during processing of the drawn preform into prismatic flow cells or such flow cells into monolithic flow cells of the '187 patent. Each of such potential glass-forming artifacts may vary along the length of the drawn preform, so causing unit-to-unit variability in optical parameters acquired from different monolithic flow cells as well as in those acquired through individual walls of a specific flow cell (e.g., 20' in FIG. 2). Moreover, the yield of monolithic flow cells processed in the aforesaid manner to comprise Coulter volumeter conduits may be significantly reduced by chipping at critical volumeter orifices.

The integral non-cylindrical envelope of monolithic flow cells according to the '187 patent is formed directly on at least a portion of prismatic flow cells by secondary machining processes. In addition to aforesaid glass-forming artifacts, machining artifacts may also adversely affect optical cytometric characterization parameters provided by a finished flow cell. As a first example of such artifacts, a wedge angle (i.e., a in FIG. 2) may occur in the flow-cell wall between any planar surface machined on a prismatic flow cell (e.g., 50 in FIG. 2) and the corresponding substantially planar surfaces of the prismatic channel formed in the glass-drawing operation (e.g., Z in FIG. 2). For optical flow cells including Coulter volumeter conduits as described in the '187 patent, the small conduit widths W' (e.g., 52 micra) make controlling such wedge angle to a desired tolerance difficult during formation of the flow-cell envelope by available processes, and although the internal radius R at the jointless corners of flow channel Z is hydrodynamically advantageous, it further reduces the extent of W' that is available as an alignment reference. As a preferable alternative, the '187 patent teaches machining a flat on the cylindrical surface of the final oversleeving tube, parallel to a planar surface of the channel, prior to drawing the preform whereby such flatted preforms have a cross-section that is substantially circular, i.e., they are substantially cylindrical. Such flats enable improved control over wall wedge angle when used as a reference during the first stages of the secondary envelope-forming processes; however, controlling the preform wedge angle between such flats and a channel surface to less than about two degrees of angle requires exceptional care, additional variability being introduced via typical flow-cell mounting techniques used during the secondary formation of envelope surfaces. While allowing acceptable coefficients of variation in lateral characterizing parameters (e.g., such as side scatter SS and fluorescence F from blood cell BC2 in FIG. 2), small variations in wall wedge angle between corresponding channel and envelope surfaces can produce disadvantageous coefficients of variation in other parameters, such as axial light loss (ALL) and low-angle forward scatter FS, that are acquired near the optical axis OA of the transducer assembly. As another example of machining artifacts, generation of a non-cylindrical surface of revolution (e.g., spherical) to provide such non-cylindrical envelope surface on a portion of a drawn preform requires such portion being centered on an axis having a desired relation to the flow-channel axis and use of, e.g., a form tool, with consequent envelope geometry depending on the accuracy and use of the forming method. Even sub-wavelength differences in optical path length between the flow channel and an envelope surface formed by secondary machining may produce refractive and dispersive effects that limit the quality of optical characterization parameters and complicate alignment of the finished flow cell during integration into a transducer assembly. Such optical artifacts originating in machining artifacts may also occur not only unit-to-unit for FIG. 2 flow cell 20', but also for individual walls of a specific flow cell 20'.

Unacceptable optical effects of aforesaid manufacturing variability arising in both glass-forming and secondary machining can be eliminated by selection of monolithic flow cells 20'. Transducer assemblies comprising flow cells 20' selected to provide optimum performance along FIG. 2 optical axis OA provide characterizing parameters of exceptional diagnostic quality, and certain hematology analyzers incorporate such assemblies that have survived multiple such selections. However, need for some such selection processes may not be evident until a monolithic flow cell 20' can be functionally tested in a partial transducer assembly; rework of a flow cell 20' or of a partial transducer assembly giving unacceptable performance adds disadvantageous costs, as well as reducing yields of both useful flow cells and transducer components.

Regardless of design, flow cells that allow acquisition of acceptable optical characterization parameters from spherical formed bodies demonstrate greater variation in such parameters acquired from formed bodies lacking at least quasi-spheroidal shape. If significantly asymmetric, such formed bodies typically transit the parameter-acquisition zone of a flow cell with their major dimension substantially aligned with the axis of sample flow, but with random orientation about said axis (i.e., the lateral profile presented at the acquisition axis is random with respect to the flow axis). Numerous formed bodies of clinical interest are asymmetric, and their random rotational orientation produces disadvantageous coefficients of variation in acquired optical characterizing parameters, with consequent increased coefficients of variation in their subpopulation data. It is known that flow channels having a rectangular cross-section preferentially orient fixed discoid red-blood cells introduced via an axisymmetric sample inlet tube (*Journal of Histochemistry and Cytochemistry*, 25:774-778, 1977), and this configuration has been used in flow cells for acquisition of cellular images (e.g., U.S. Pat. Nos. 5,088,816; 5,412,466; and 5,825,477). Non-axisymmetric nozzles on sample inlet tubes (e.g., as in aforesaid U.S. Pat. No. 5,825,477) and appropriately beveled tips of an axisymmetric inlet tube generate such orienting rotational forces; the latter have been used in experimental transducer assemblies to obtain S signals from oriented fixed discoid red-blood cells (*Biophysical Journal*, 23:1-5, 1978) or F signals from oriented stripped spermatozoa (*Journal of Histochemistry and Cytochemistry*, 27:353-358, 1979; *Cytometry*, 7:268-273, 1986). Reduced coefficients of variation in acquired optical characterization parameters, with consequent improved classification of formed bodies into subpopulations, make desirable transducer assemblies that apply such orienting rotational forces to asymmetric formed bodies in samples.

In summary, transducer assemblies comprising optical flow cells having not only aforesaid advantages of monolithic flow cells as disclosed in the '187 patent, but also enabling improved yields with less selection from production through integration into acceptably functioning transducer assemblies, would advantageously facilitate acquiring the various distinguishing parameters used by automated hematology analyzers and flow cytometers to differentiate and characterize various formed-bodies in liquid samples. Transducer assemblies comprising such flow cells having a flow-channel cross-section so formed as to apply an orienting force to formed bodies presenting asymmetric profiles when passing through the parameter-acquisition portion thereof, either separately or in combination with a sample inlet tube so formed as to apply an orienting force to such formed bodies, would advantageously decrease variability in optical cytometric characterization parameters acquired during the transductive process in such formed-body analyzers.

BRIEF SUMMARY OF THE INVENTION

Exemplary embodiments as described and claimed herein are based on the finding that, by providing flow-channels and envelopes in independent components of insulative transparent material, improved control may be attained over both the quality of flow-channel wall surfaces and the alignment of envelope surfaces to flow-channel surfaces of compound flow cells comprising such components, whereby optical characterization parameters acquired through the wall of such flow cells become more consistent, selection of acceptable flow cells may be made at a significantly lower level of integration into a transducer assembly, and advantageously significant reductions in costs and improvement in yields of both flow cells and transducer assemblies may be obtained. According to one aspect of the invention, flow channels of such compound flow cells are provided via improvements in methods used to make prismatic flow cells that retain the many proven advantages of monolithic (i.e., joinless) flow cells but reduce the probability of artifacts to which such methods are liable. According to another aspect of the invention, envelopes of such compound flow cells are provided via adaptation of commercial optical components of high precision and quality.

In view of the foregoing discussion, an object of this invention is to provide an improved method for making optical flow cells for flow cytometric characterization of formed bodies in a liquid sample, said method offering advantageously significant reduction in costs and improved yields by providing two elements of insulative transparent material, the first a substantially cylindrical monolithic element surrounding a seamless interior flow channel at least an axial portion of which is surrounded by a continuous surface of preferably non-circular cross-section and the second element having both a concave surface conformed to such first element and an exterior non-cylindrical optical envelope of predetermined form and orientation relative to such concave surface, assembling said elements so that such concave surface of said second element may be positioned with respect to and joined to said first element, and optically joining said second element to said first element to form a compound flow cell having a desired fixed spatial relationship between a reference feature of the first element and a reference feature of the second element whereby non-axisymmetric refractive effects on optical characterizing parameters acquired from formed bodies passing through said flow channel are minimized.

A second object of this invention is to provide optical flow cells having the cytometric advantages of monolithic flow cells, but at reduced costs and with improved production yields, said flow cells comprising two elements made of insulative transparent material, the first a substantially cylindrical monolithic element surrounding a seamless internal flow channel at least an axial portion of which is surrounded by a continuous surface of preferably non-circular cross-section so as to define an acquisition zone for cytometric characterizing parameters and the second an annular element having both a concave surface conformed to receive such first element and an exterior non-cylindrical optical envelope in a predetermined spatial relationship to said concave surface, whereby prior to such second element being optically joined fixedly in final working configuration to said first element a reference feature of said second element may be spatially positioned and aligned with respect to a reference feature of said first element so as to minimize variation due to refractive effects on optical characterizing parameters acquired on a predetermined parameter-acquisition axis from formed bodies passing through such parameter-acquisition zone in the first element of the compound optical flow cell so formed.

A third object of this invention is to provide an improved method for cytometrically differentiating various types of formed bodies in liquid suspension using a flow cell according to the invention that comprises at least one wall, such wall being between and defined by a seamless interior flow channel at least an axial portion of which is surrounded by a continuous surface of preferably non-circular cross-section and an exterior envelope at least a portion of which is non-cylindrical, through which various cytometric optical parameters may be derived of formed bodies transiting said flow channel.

A fourth object of this invention is to provide an improved method for cytometrically differentiating various types of formed bodies in liquid suspension using a flow cell according to the invention that comprises at least one wall, said wall being between and defined by a seamless interior flow channel at least an axial portion of which is surrounded by a continuous surface of preferably non-circular cross-section and an exterior envelope at least a portion of which is non-cylindrical, through which various cytometric optical parameters may be derived of formed bodies transiting such flow channel in which at least one of the Coulter volume (V) and conductivity (C) parameters is detectable.

According to yet another aspect, aforesaid improved method for making such monolithic first elements has been found to improve control over the cross-sectional geometry of non-axisymmetric flow channels so that sample-introduction tubes for use in cytometric transducer assemblies may provide more predictable rotational orienting forces about such channel axes, whereby a greater number of asymmetric formed bodies in liquid samples transiting such channels may be preferentially presented in a desired orientation relative to an optical interrogation beam through the parameter-acquisition zone of such transducer assemblies.

A fifth object of this invention is to provide an improved method for making sample-introduction tubes for use in cytometric transducer assemblies, said method providing a non-axisymmetric cross-section in flow channels therein whereby an orienting rotational force about such tube axis is applied to asymmetric formed bodies in liquid samples exiting said sample inlet tube.

A sixth object of the invention is to provide sample inlet tubes for use in cytometric transducer assemblies, said tubes having an asymmetric cross-section in the tube flow-channel, nozzle, or tip whereby an orienting rotational force about such inlet-tube axis is applied to asymmetric formed bodies suspended in liquid samples exiting the inlet tube.

A seventh object of the invention is to provide an improved method for cytometrically differentiating various types of formed bodies in liquid suspension using a sample inlet tube according to the invention, whereby a greater number of asymmetric formed bodies are caused to transit the parameter-acquisition portion of a flow-cell flow channel in a predetermined lateral orientation relative to a selected feature of the flow cell, thereby reducing randomness in lateral presentation of such bodies to an optical interrogation beam through the parameter-acquisition zone of such transducer assemblies.

A final object of the invention is to provide cytometric transducer assemblies providing improved control over sample flow rates through the parameter-acquisition zone of the flow cell therein in combination with orienting rotational forces applied to asymmetric bodies in such sample flows.

All features of the described systems are applicable to the described methods mutatis mutandis, and vice versa.

In one aspect, embodiments of the present invention encompass methods for making a transparent compound optical flow cell of the type used to characterize formed bodies passing through the flow cell, the optical flow cell having formed therein a rectilinear internal flow channel. An exemplary method can include the steps of providing a cylindrical monolithic preform having a thick-wall glass tube having an axially-extending channel therethrough and a transition temperature, the channel having a substantially uniform original cross-section of a desired shape, heating the preform to a predetermined temperature above the transition temperature of the glass tube, axially drawing the preform at a controlled rate, for a controlled time, and at a constant angular orientation, to achieve a desired reduced cross-sectional area of the axially-extending channel, providing an optical element, the optical element having a conforming surface that conforms to a segment of the drawn preform, and an exterior non-cylindrical envelope of predetermined form and orientation relative to the conforming surface, assembling the optical element on the segment so that the optical element and the segment are in a desired spatial relationship, and the conforming surface of the optical element is positioned so as to minimize non-axisymmetric refractive effects on optical characterizing parameters acquired from formed bodies passing through the reduced cross-sectional area of the axially-extending channel, and optically joining the optical element to the segment so as to fix the optical element and the segment in the desired spatial relationship.

In another aspect, embodiments of the present invention encompass methods where the shape of the original channel cross-section is a circle.

In another aspect, embodiments of the present invention encompass methods where the reduced cross-sectional area of the axially-extending channel has a shape selected from the group consisting of a square, a hexagon, a rectangle, and an ellipse.

In another aspect, embodiments of the present invention encompass methods where the cylindrical monolithic preform includes an insulative transparent material and the optical element includes an insulative transparent material.

In another aspect, embodiments of the present invention encompass methods where the insulative transparent material of the preform includes $SiO_2$ and the insulative transparent material of the optical element includes $SiO_2$.

In another aspect, embodiments of the present invention encompass methods where the conforming surface of the optical surface has a shape selected from the group consisting of a square, a hexagon, a rectangle, and an ellipse.

In another aspect, embodiments of the present invention encompass methods where the exterior envelope of the optical element has a cross-section shape selected from the group consisting of a square, a rectangle, a hexagon, and a circular segment.

In another aspect, embodiments of the present invention encompass methods where the joining step includes forming an optical join between the optical element and the segment, the optical join having an optical-joining material that is substantially non-fluorescing, and where the optical element, the join, and the segment each have a respective index of refraction, the respective indices of refraction being substantially equal.

In another aspect, embodiments of the present invention encompass methods where the predetermined temperature is within a range from between 1,500° C. and 1,750° C. and the cylindrical monolithic preform has a drawing viscosity between $6 \times 10^6$ poise and $1,000 \times 10^6$ poise.

In another aspect, embodiments of the present invention encompass methods where the conforming surface of the optical element includes a concave shape.

In one aspect, embodiments of the present invention encompass transparent compound optical flow cells of the type used to characterize formed bodies passing through the flow cell. An exemplary optical flow cell can include an axially drawn preform having an axially-extending channel therethrough, an optical element having a conforming surface that conforms to a segment of the drawn preform, and an exterior non-cylindrical envelope of predetermined form and orientation relative to the conforming surface, and an optical join fixing the preform and the optical element in a desired spatial relationship. The conforming surface of the optical element is positioned so as to minimize non-axisymmetric refractive effects on optical characterizing parameters acquired from formed bodies passing through the cross-sectional area of the axially-extending channel of the drawn preform.

In another aspect, embodiments of the present invention encompass systems where the axially-extending channel of the axially drawn preform includes a cross-sectional area having a shape selected from the group consisting of a square, a hexagon, a rectangle, and an ellipse.

In another aspect, embodiments of the present invention encompass systems where the axially drawn preform includes an insulative transparent material and the optical element includes an insulative transparent material.

In another aspect, embodiments of the present invention encompass systems where the insulative transparent material of the preform includes $SiO_2$ and the insulative transparent material of the optical element includes $SiO_2$.

In another aspect, embodiments of the present invention encompass systems where the conforming surface of the optical surface has a shape selected from the group consisting of a square, a hexagon, a rectangle, and an ellipse.

In another aspect, embodiments of the present invention encompass systems where the exterior envelope of the optical element has a cross-section shape selected from the group consisting of a square, a rectangle, a hexagon, and a circular segment.

In another aspect, embodiments of the present invention encompass systems where the optical join includes an optical-joining material that is substantially non-fluorescing, and where the optical element, the join, and the segment each have a respective index of refraction, the respective indices of refraction being substantially equal.

In another aspect, embodiments of the present invention encompass systems where the axially drawn preform is drawn at a temperature within a range from between 1,500° C. and 1,750° C. and has a drawing viscosity between $6 \times 10^6$ poise and $1,000 \times 10^6$ poise.

In another aspect, embodiments of the present invention encompass systems where the conforming surface of the optical element includes a concave shape.

In another aspect, embodiments of the present invention encompass systems where a reference feature of the optical element is spatially positioned and aligned with respect to a reference feature of the drawn preform corresponding to the desired spatial relationship between the preform and the optical element.

Embodiments of the present invention and their various advantages will be better appreciated from the ensuing detailed description of exemplary embodiments, reference being made to the accompanying drawings, in which like reference characters denote like parts and in which for clarity all internal sample passageways are shown enlarged and out of proportion with respect to external envelopes of components in which they are comprised.

DETAILED DESCRIPTION OF THE INVENTION

Figure 2:
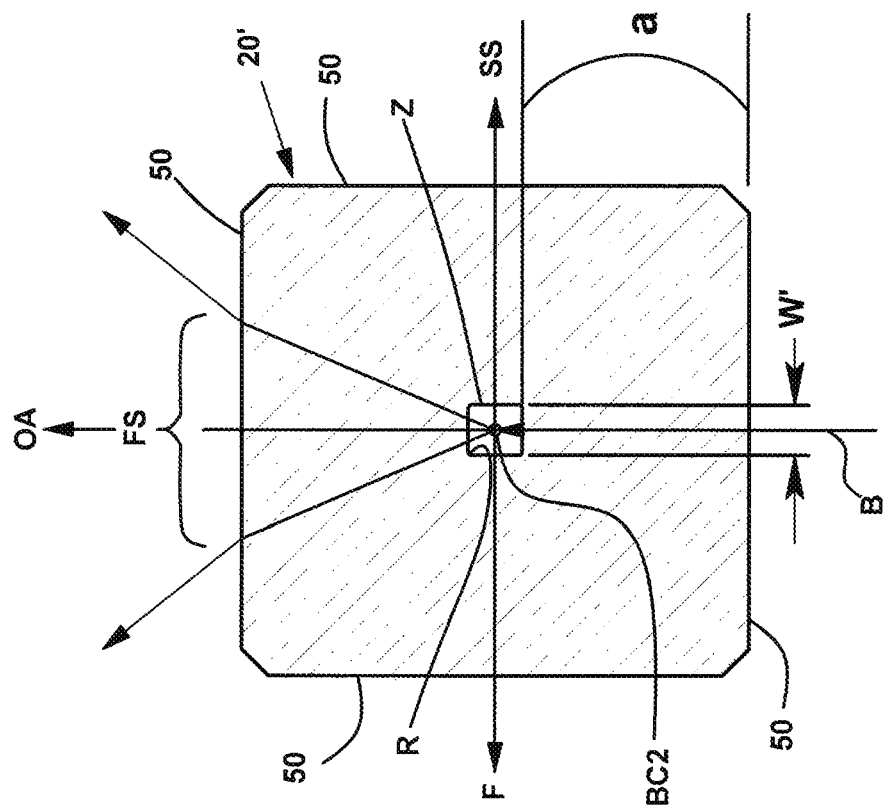
FIG. 2 illustrates a cross-sectional view through the prismatic parameter-acquisition zone of an exemplary prior-art monolithic flow cell which contains the liquid flow and Coulter excitation currents within a joinless flow channel and avoids the many disadvantages of composite flow cells.
Figure 1:
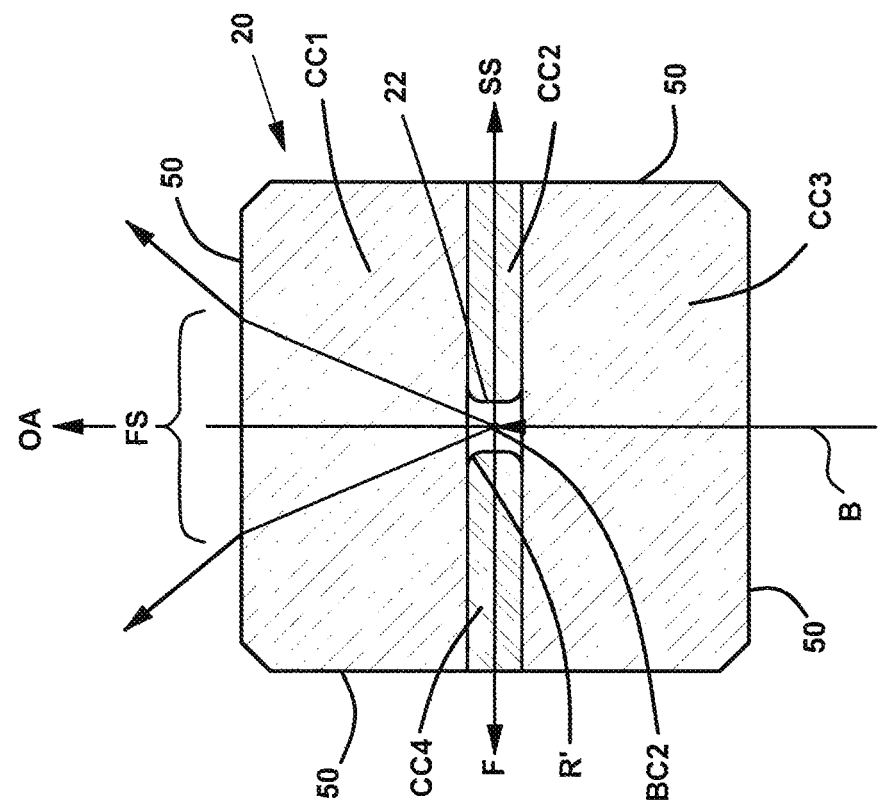
FIG. 1 illustrates a cross-sectional view through the prismatic parameter-acquisition zone of an exemplary prior-art composite optical flow cell comprising joined complementary components having the joins exposed to liquid flow and Coulter excitation currents within the flow channel.

Hematology analyzers and other flow cytometers acquire diagnostically important data from samples of patient body fluids containing various formed bodies or particles, and many different embodiments have been developed. These instruments comprise various components that are fluidically coupled to contain patient samples for characterization of formed bodies therein, acquire specific cytometric characterizing parameters from said particulate bodies, and direct analyzed samples and flushing fluids to appropriate receptacles. All incorporate an optical flow cell through an internal passageway of which such samples may be passed after undergoing various preparatory protocols and in which various properties of the particulate bodies may be sensed, whereby the several types of subpopulations of formed bodies therein may be differentiated and enumerated and the derived parameters processed and correlated to provide desired diagnostics. Hereinafter it will be understood that an optical flow cell may include or may be limited to include only: a) one or more elements made of insulative transparent material; b) an interior through passageway in one said element at least an axial portion of which permits sensing of formed-body characteristics by cytometric methods in a parameter-acquisition zone; and c) an external envelope on at least one element a surface of which forms with such passageway at least one wall of a parameter-acquisition zone through which an interrogating beam of optical radiation may be caused to interact with formed bodies transiting such parameter-acquisition zone, whereby one or more of the optical absorption, light-scattering, and fluorescence properties of such bodies may be sensed through one or more other such walls; here, "insulative" means not conducting electricity, and "transparent" means readily transmitting optical radiation, e.g., light. As noted in the introductory portion hereof, it is preferable that non-axisymmetric refractive effects be minimized at the external envelope surface of such flow cells and most preferable that such effects be minimized at surfaces of both the external envelope and parameter-acquisition, or sensing, portion of such passageway. In flow cells for acquisition of purely optical characterizing parameters such passageway is typically of uniform cross-section greater than about 150 micra in width. However, instruments incorporating simultaneous acquisition of optical and Coulter DC volume (V) and/or RF electrical conductivity (C) parameters from an individual formed body also require that the parameter-acquisition zone be a constriction, or volumeter conduit, in the internal passageway; such volumeter conduits are typically less than 100 micra in width and between 0.75 and 2.0 times their width in length. Examples of the latter flow cells and of hematology analyzers using them are more fully disclosed in above-mentioned, commonly assigned U.S. Pat. Nos. 5,125,737 and 6,228,652, contents of which are incorporated herein in entirety by reference. Briefly, such analyzers operate to automatically sense, differentiate, and count various types of formed bodies (e.g., red blood cells, white blood cells, platelets, etc.) contained in different samples of patient body fluids and to report their findings.

Figure 3:
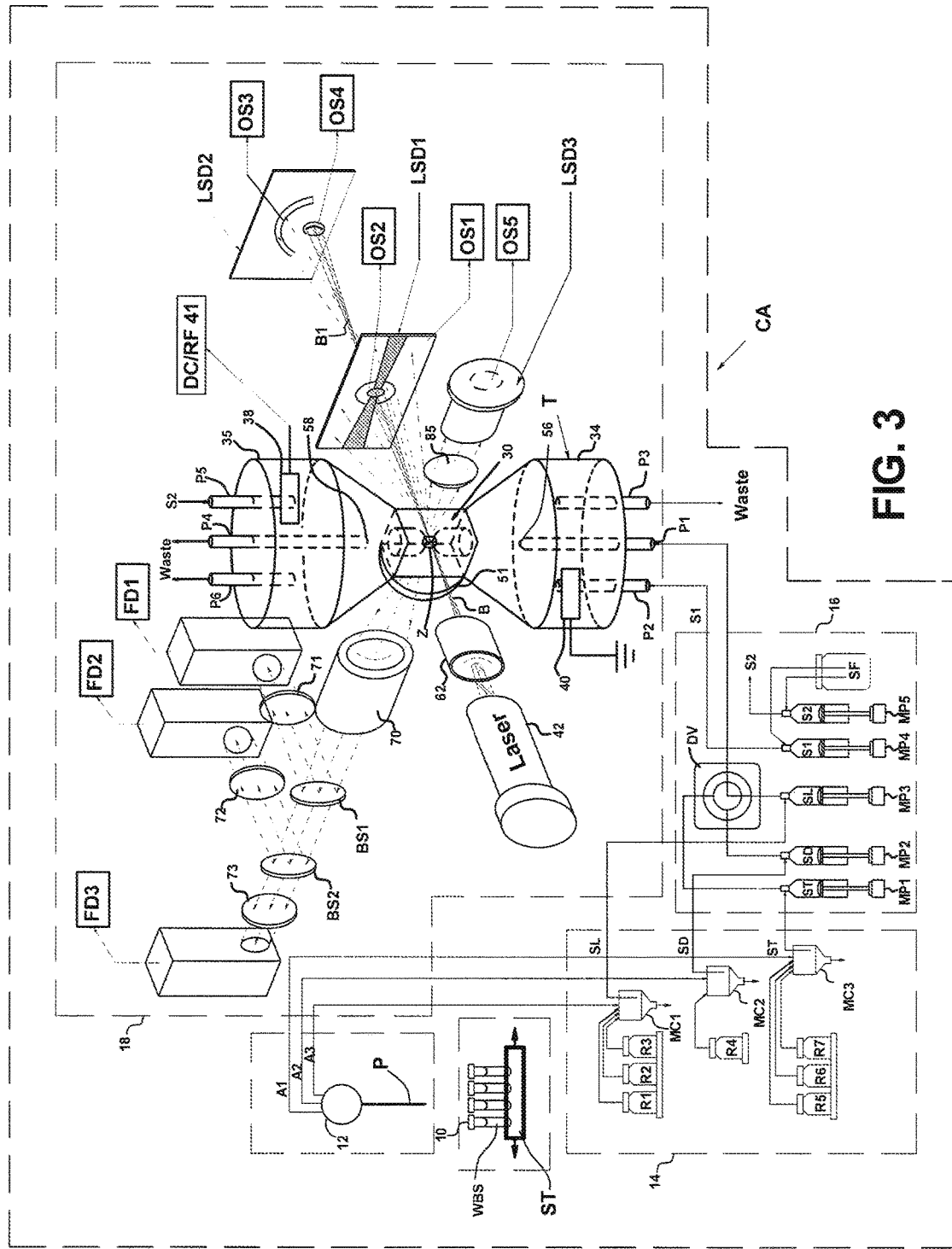
FIG. 3 is a schematic illustration of the sample-processing and data-acquisition portions of a flow cytometer incorporating a preferred embodiment of a four-sided compound optical flow cell designed and manufactured in accordance with the method of the present invention.
Figure 11:
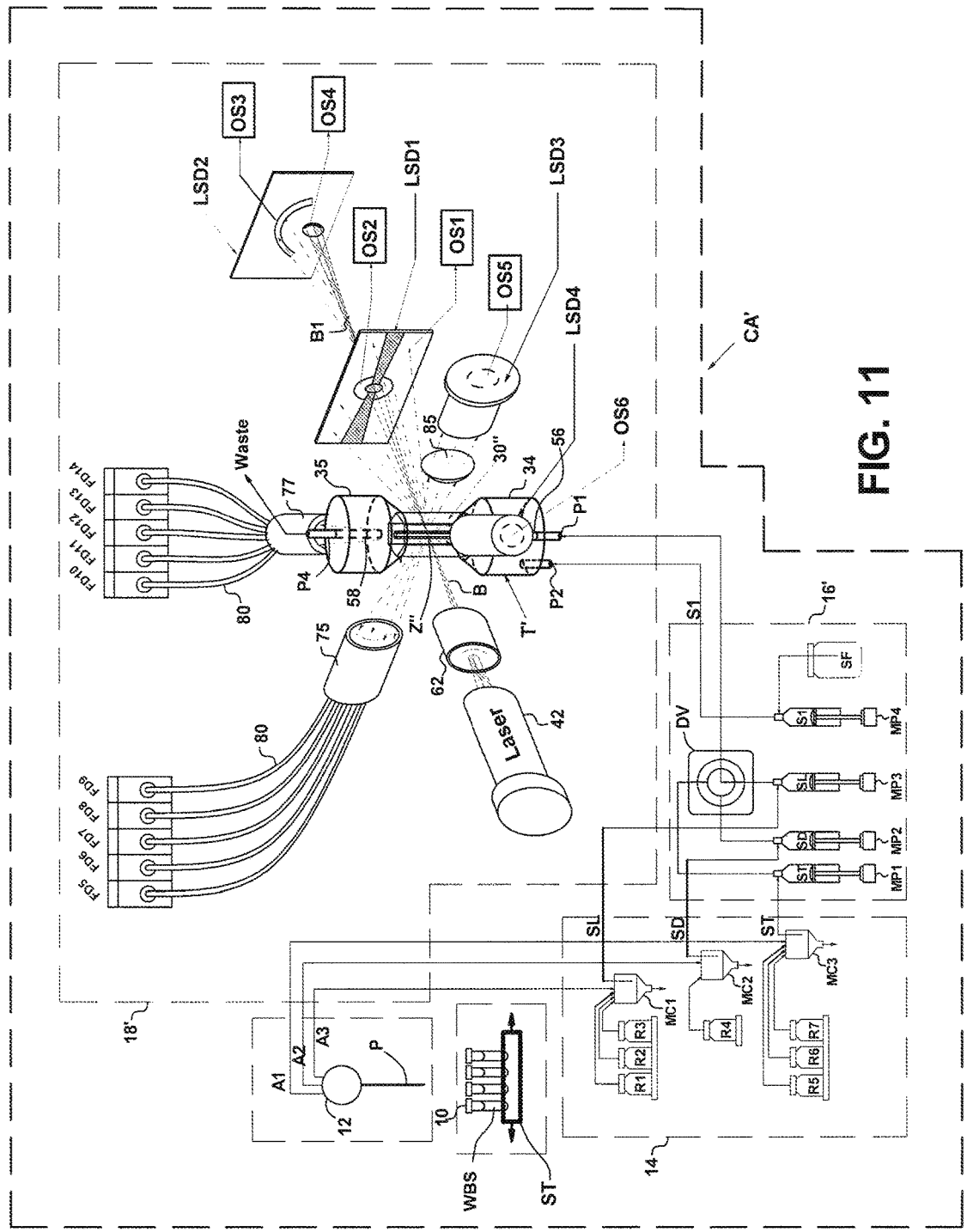
FIG. 11 is a schematic illustration of the sample-processing and data-acquisition portions of a flow cytometer that relies solely on optical properties of formed bodies to differentiate subpopulations of same, in which distinguishing parameters are acquired from formed bodies transiting the hexagonal parameter-acquisition zone of the compound optical flow cell illustrated in FIG. 10.

Referring now to the drawings, sample-handling and data-acquisition portions of an exemplary hematology analyzer CA are schematically illustrated in FIG. 3, while such portions of an exemplary flow cytometer CA' are similarly shown in FIG. 11. FIG. 3 analyzer CA employs simultaneous sensing of optical and Coulter V and/or C characterizing parameters from individual formed bodies in such samples, while FIG. 11 cytometer CA' senses only optical parameters of such formed bodies. Instruments illustrated in FIGS. 3 and 11 are distinguished from prior-art instruments in comprising a respective transducer assembly T or T' that is structured in accordance with the present invention; T or T' comprises, singly or in combination, a flow cell 30 or 30" and/or a sample inlet tube 56, both of which are structured and fabricated in accordance with other aspects of the present invention. Flow cell 30 or 30" is the central component of respective transducer assembly T or T' that operates to interrogate each formed body in a prepared sample as these pass through parameter-acquisition zone Z or Z" in a stream from inlet tube 56. Said flow cells are sealingly attached to cap elements 34 and 35 of respective FIG. 3 transducer assembly T or FIG. 11 transducer assembly T', which elements via their internal geometry define chambers, and are fluidically coupled at one end to the internal chamber in cap element 34 and at the other end to a similar chamber in cap element 35. Cap elements 34 and 35 are mounted in a supporting structure, not shown in FIG. 3 or 11, and are provided with a respective plurality of ports P1-P6 in FIG. 3 and P1, P2, and P4 in FIG. 11. Said ports are fluidically coupled to said internal chambers and serve to: 1) introduce into flow cell 30 or 30" one or more prepared samples to be analyzed through port P1 and inlet tube 56 and a sheath liquid S1 through port P2; 2) drain exiting sample(s) and sheath liquid to waste; 3) flush one or both internal chambers in cap elements 34 and 35 to waste; and 4) provide a vacuum to prime tubing supplying the various ports. It will be appreciated that transducer assemblies having similar functionality may be implemented in a variety of forms, e.g., sample injection via the multi-port nozzle of the '652 patent may be useful in certain embodiments. As will be discussed, transducer assemblies may be otherwise structured to provide enhanced cytometric function.

Transducer assemblies T and T' are supported by a fluidically coupled sample-handling system and interact with various components of transducer module 18 or 18' in respective FIG. 3 instrument CA or FIG. 11 instrument CA' to sense characterizing parameters of the various formed bodies in a patient sample. Patient samples (e.g., whole-blood samples WBS) are presented to such instruments in different test tubes or vials 10 which may be moved within the instrument by a sample transport ST. On presentation of such vials to an aspiration probe P, a predetermined volume of sample is aspirated from each. Each aspirated sample is segmented by a conventional blood-sampling valve 12 to produce a plurality of aliquots (e.g., A1-A3) that are then dispensed to different mixing chambers (e.g., MC1-MC3) within a sample-preparation component 14 of the analyzer. While in the mixing chambers, each aliquot is mixed with one or more reagents (e.g., R1-R7) adapted to selectively react with and/or dilute certain types of formed bodies in the sample. Sample-preparation component 14 can produce, e.g., a lysed and stained sample $S_L$ comprising predominantly white blood cells and other cells (e.g., nucleated red blood cells) that have been stained with a fluorescent dye; a diluted and stained sample $S_D$ containing all blood cell types in a highly diluted suspension, some of such cells (e.g., the reticulocyte subset) being stained with a fluorescent dye; and a lysed and tagged sample $S_T$ comprising predominantly white blood cells in a suspension, including selected white cells (e.g., cells positive for CD4 or CD8) that have been stained or otherwise labeled, e.g., via a monoclonal antibody, with a fluorochrome or fluorescent particle. Precisely metered volumes of each prepared sample, as provided by metering mechanism 16 (16' in FIG. 11), are then selected by a conventional distribution valve DV and pumped (e.g., by metering pumps MP1, MP2, or MP3) through sample input port P1 to sample inlet tube 56 of transducer assembly T or T'. Sample inlet tube 56 operates to regulate and direct the sample flow injected into sheath liquid in the chamber within cap element 34. Metering pump MP4 provides sheath liquid SF as S1 to ports P2 of said transducer assemblies so as to maintain a predetermined pressure differential between chambers within cap elements 34 and 35 and hydrodynamically center sample flows from inlet tube 56 upward through respective parameter-acquisition zone Z or Z" in flow cell 30 or 30" to waste via exit tube 58 and port P4. The sample-handling arrangement described hereto is common to the embodiments of FIG. 3 and FIG. 11, but it will be understood by those skilled in the cytometric art that other fluidic configurations may be used to prepare and deliver patient samples via port P1 and inlet tube 56 to flow cell 30 or 30" for acquisition of differentiating parameters of the formed bodies therein.

As samples individually exit inlet tube 56 and flow through the parameter-acquisition zone Z or Z" of respective flow cell 30 or 30" in FIGS. 3 and 11, certain optical properties of individual formed bodies or other particles therein are simultaneously sensed and converted to electrical signals as a result of interaction with optical radiation, e.g., laser beam B as shown in respective transducer modules 18 or 18'. Signals so derived occur as electrical pulses and are parameters of each formed body's absorption of radiation (A), its various light-scattering (S) properties [i.e., forward scatter (FS), side scatter (SS), and/or back scatter (BS)], and its fluorescence properties (F). In FIG. 3, Coulter volume V and/or RF conductivity C are also simultaneously determined as pulses via fluidly contacted electrodes 38 and 40 in the respective chambers of cap elements 35 and 34, said conventional electrodes being conductively connected to DC/RF circuit 41. Various combinations of such signals are processed by conventional cytometer components, such as disclosed in the '652 patent but not shown in FIG. 3 or 11, to provide information appropriate to correlation by algorithms providing desired diagnostic information. As will be appreciated by those skilled in cytometric art, FIGS. 3 and 11 illustrate but two of the wide variety of transducer modules suitable for acquisition of such signals.

Figure 16:
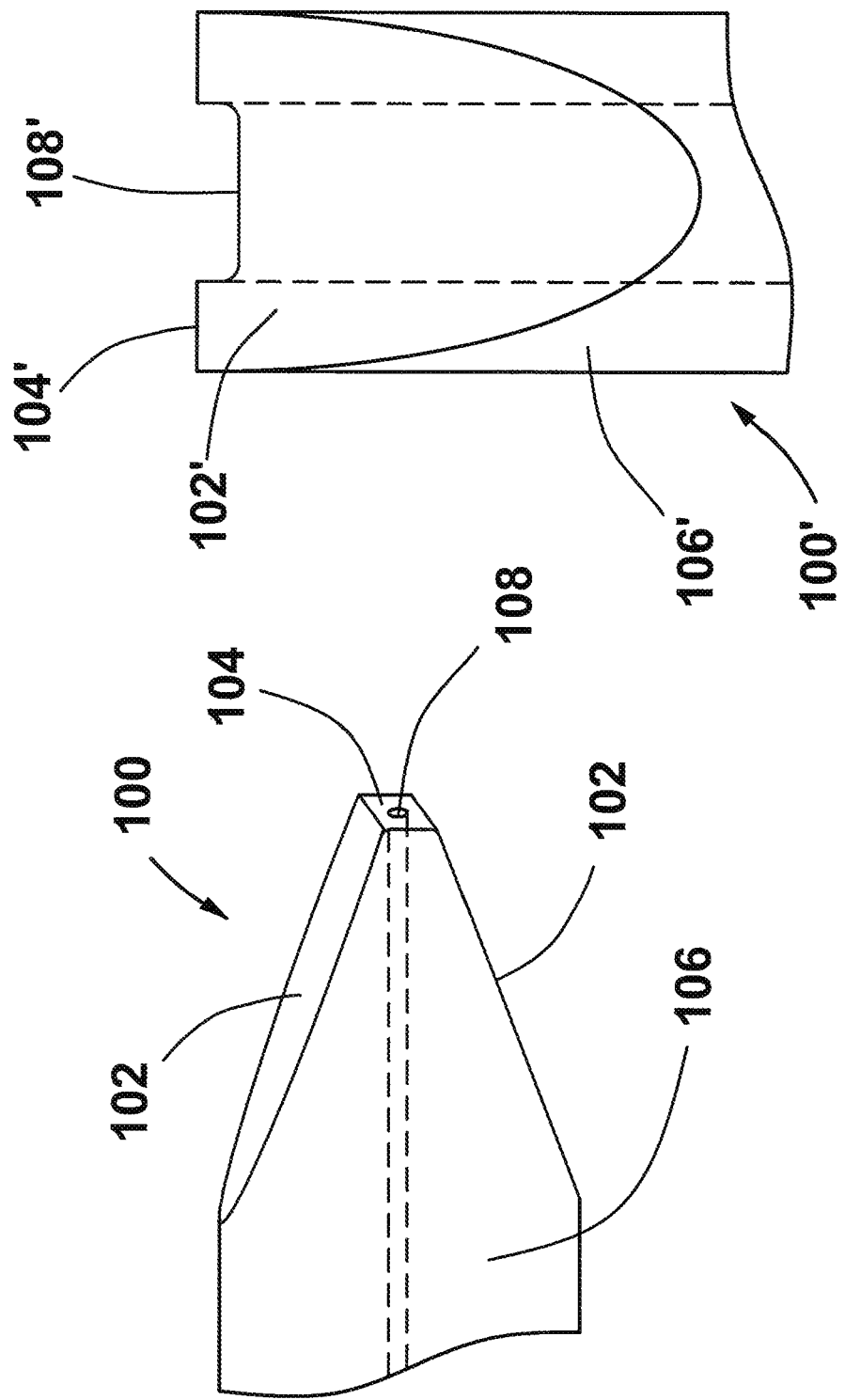
FIGS. 16A and 16B illustrate exemplary sample introduction tubes for use in transducer assemblies comprising optical flow cells.

The different sensing approaches used in respective transducer modules 18 and 18' of FIGS. 3 and 11 require different sample-handling support for transducer assemblies T or T' in instruments CA and CA'. The parameter-acquisition zone Z in FIG. 3 flow cell 30 is defined by the Coulter volumeter conduit therein, which due to its small cross-section typically requires close control of the differential pressure between cap elements 34 and 35 during parameter acquisition, with rigorous flushing of these chambers afterward. To minimize recirculation of formed bodies back into the ambient electric field of volumeter conduit Z and to maintain a predetermined pressure differential across the volumeter conduit, metering pump MP5 in metering mechanism 16 provides port P5 of cap element 35 with sheath liquid SF as S2, which exits port P4; the greater volume of S2 delivered thereby during the flush phase also exits port P6; cap element 34 is flushed with SF supplied as S1 by metering pump MP4 through port P2, with waste exiting port P3. (Understanding of the description hereto may be facilitated by examination of more-detailed FIGS. 16 and 18A-B.) For applications not requiring Coulter V and/or C characterizing parameters, one of the purely optical flow cells 30' in FIG. 7A or FIG. 7B, of appropriate cross-section in passageway 32', may be substituted for flow cell 30 in FIG. 3; absence of a volumeter conduit in flow cell 30' negates need for respective electrodes 38 and 40 in cap elements 35 and 34 and DC/RF circuit 41, but does require modification of other components of transducer module 18 or 18' related to acquisition of the several optical characterizing parameters. As indicated in FIG. 11, the larger typical sample passageways in such purely optical flow cells may allow elimination of other FIG. 3 constituents (e.g., metering pump MP5 in metering mechanism 16 and ports P3, P5, and P6 of transducer assembly T). As will be apparent to those skilled in this art, other fluidic arrangements may be used to move prepared samples through the parameter-acquisition zone Z or Z" of the flow cell 30 or 30" in transducer assembly T or T' and to a waste receptacle for proper disposal.

Optical flow cells, e.g., FIG. 3 flow cell 30 or FIG. 11 flow cell 30", may not only constitute an important element in transducer assemblies such as T or T', but may also determine the overall quality of characterizing parameters resulting from the transductive process. As reviewed in the introductory portion hereof, non-axisymmetric refraction at the inner and outer surfaces of flow-cell walls places a significant limitation on the quality of such parameters; as disclosed in the '187 patent, joinless prismatic optical flow cells minimize non-axisymmetric refractive effects at the flow-passageway surface of the parameter-acquisition zone. Such prismatic flow cells are a monolithic structure preferably made of $SiO_2$ by glass-forming methods and having a through channel formed during that process suitable for containing cells in a fluid stream, said channel being defined by at least three substantially planar surfaces and of sufficient length as to permit measurement of cell characteristics by cytometric methods. Because of the refractive difference between flow-cell walls and the surrounding air, for many cytometric applications the cylindrical envelope of such flow cells results in unacceptable non-axisymmetric refractive effects. The '187 patent teaches formation of an integral non-cylindrical envelope on prismatic flow cells, whereby non-axisymmetric refractive effects at both the inner and outer wall surfaces of monolithic flow cells may be minimized. Artifacts of glass-forming and machining processes used to fabricate monolithic flow cells were noted in the introductory portion hereof, as were disadvantageous consequences of such artifacts during processing and integration of such flow cells into acceptable transducer assemblies. Details of fabrication and structure for an exemplary monolithic flow cell are summarized in the first data column of Table 1.

Table 1. Comparison of a monolithic flow cell according to the method of the '187 patent and a compound flow cell according to the method herein described. Both exemplary flow cells are based on prismatic flow cells having a four-sided flow channel 52 micra between opposing surfaces and 10-micra corner radii; square envelopes having flat surfaces at least 4.2 mm in width are assumed. The radius used in calculation of the reciprocal radius of the channel wall surfaces is the average of at least 20 averaged radii of best-fit circles for each of the four wall surfaces as obtained by vision-system measurements.

Figure 6:
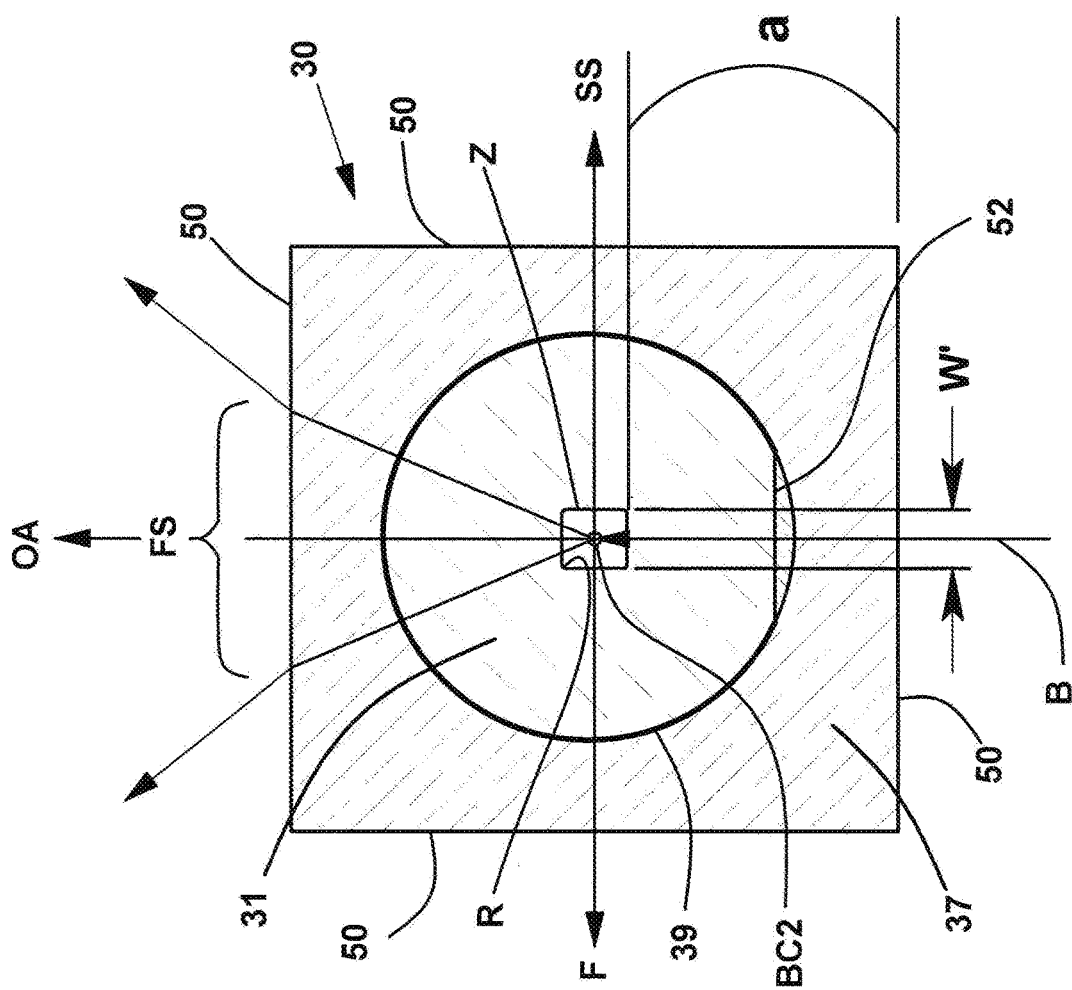

| Parameter | U.S. Pat. No. 8,189,187 | This application |
| --- | --- | --- |
| Collapsing and fusing temperature, C. ° | 1,610 to 1,860 | 1,610 to 1,860 |
| Collapsing and fusing viscosity, $\times 10^6$ poise | 60 to 1 | 60 to 1 |
| Oversleeve tubes in prismatic preform | 5 | 3 |
| Preform drawing temperature, C. ° | 1,610 to 1,860 | 1,500 to 1,750 |
| Preform drawing viscosity, $\times 10^6$ poise | 60 to 1 | 1,000 to 6 |
| Reciprocal radius of 28-micra span, $mm^{-1}$ | 0.30 | 0.19 |
| Structure of finished flow cell | Monolithic; FIG. 2 | Compound; FIG. 6 |
| Flow-channel contents in contact with join? | No; joinless. | No; external join. |
| Flow cell envelope | Integral, machined | Independent |
| Alignment of flow channel to envelope | Fixed by machining | Adjustable |

Figure 4:
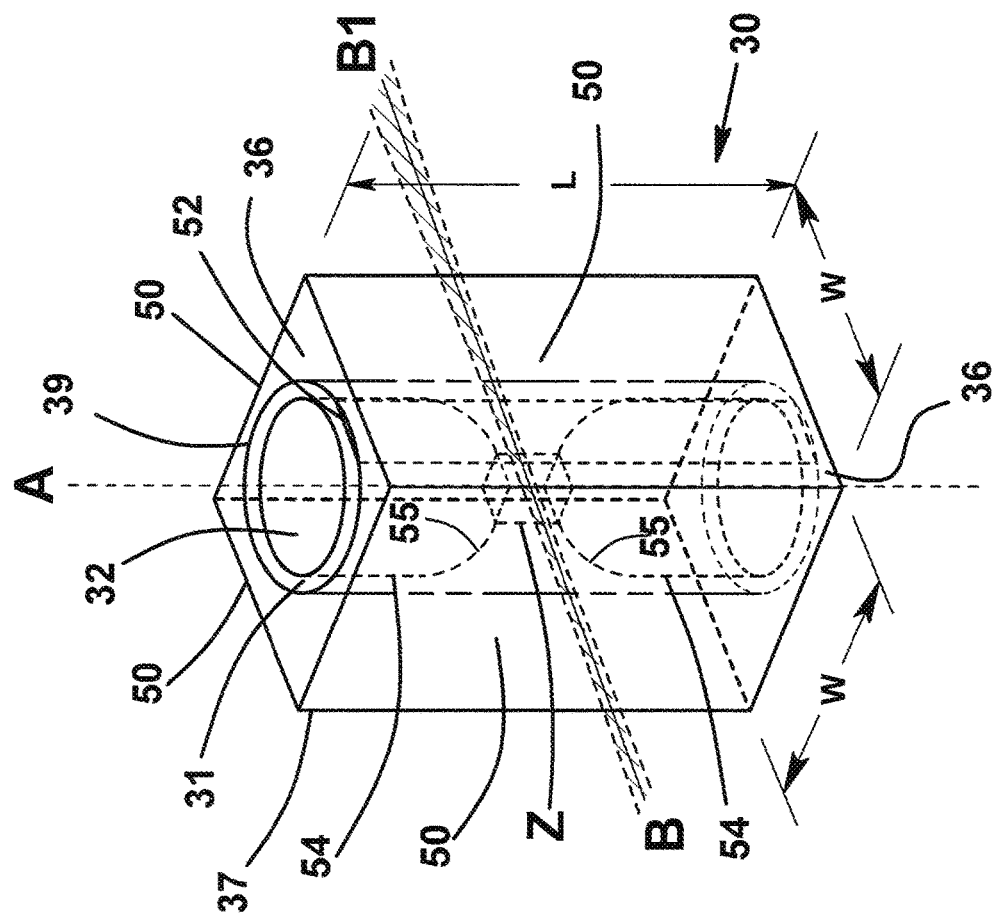
FIG. 4 is a perspective illustration of the compound optical flow cell used in the FIG. 3 instrumentation to acquire both optical and at least one of the Coulter volume (V) and conductivity (C) characterizing parameters of formed bodies passing through the prismatic parameter-acquisition zone of a joinless flow channel containing the liquid flow and Coulter excitation currents.
Figure 5:
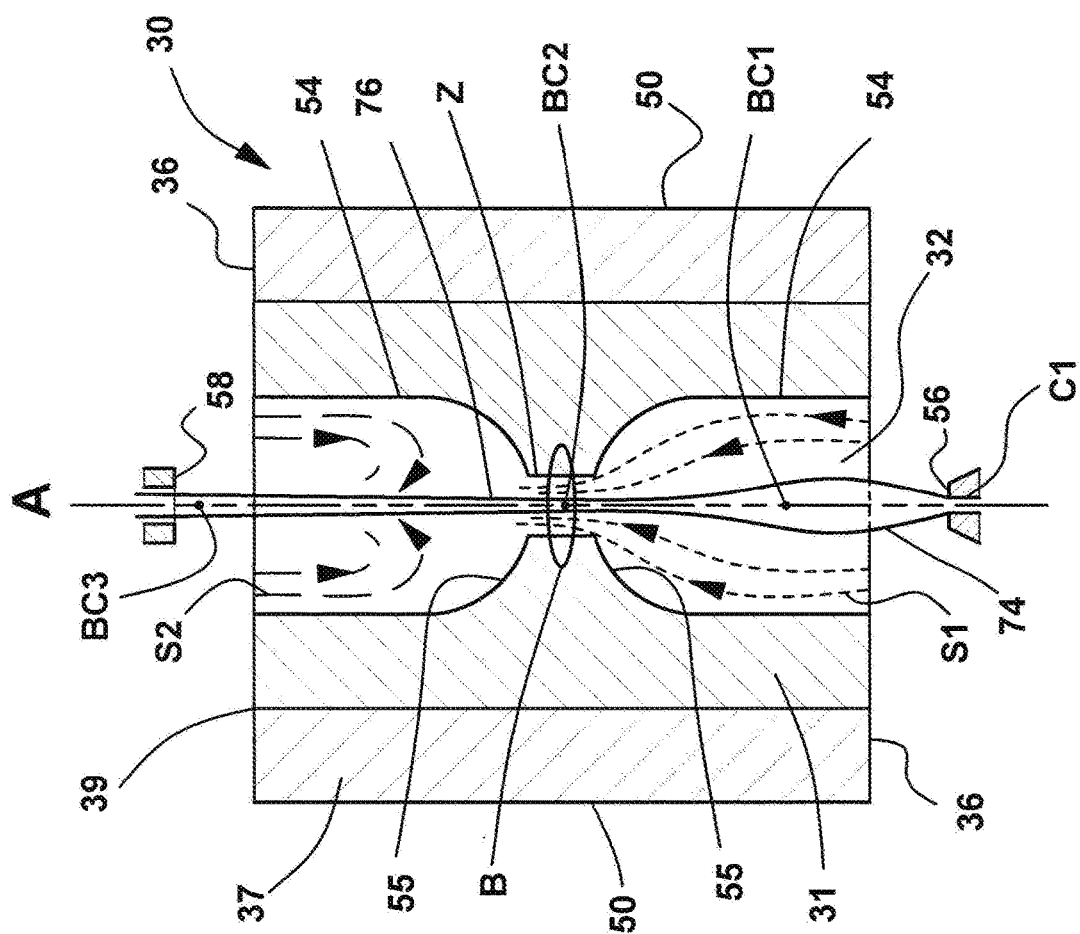
FIGS. 5 and 6 illustrate longitudinal and cross-section views of the square compound optical flow cell shown in FIG. 4, FIG. 5 including the flow-cell axis and FIG. 6 being taken in a plane through the four-sided parameter-acquisition zone that includes the optical axis of excitation.
Figure 9:
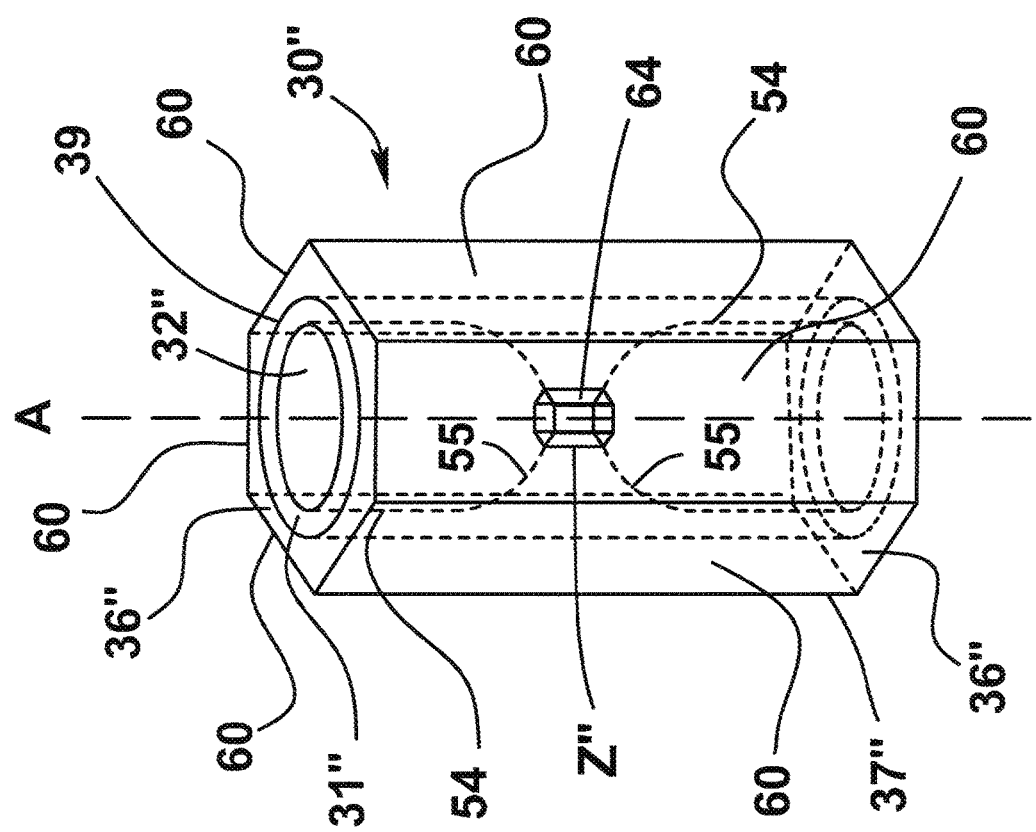
FIG. 9 is a perspective illustration of a six-sided compound optical flow cell that is readily made by the manufacturing method of the invention and is useful in another embodiment of the FIG. 3 instrumentation.
Figure 10:
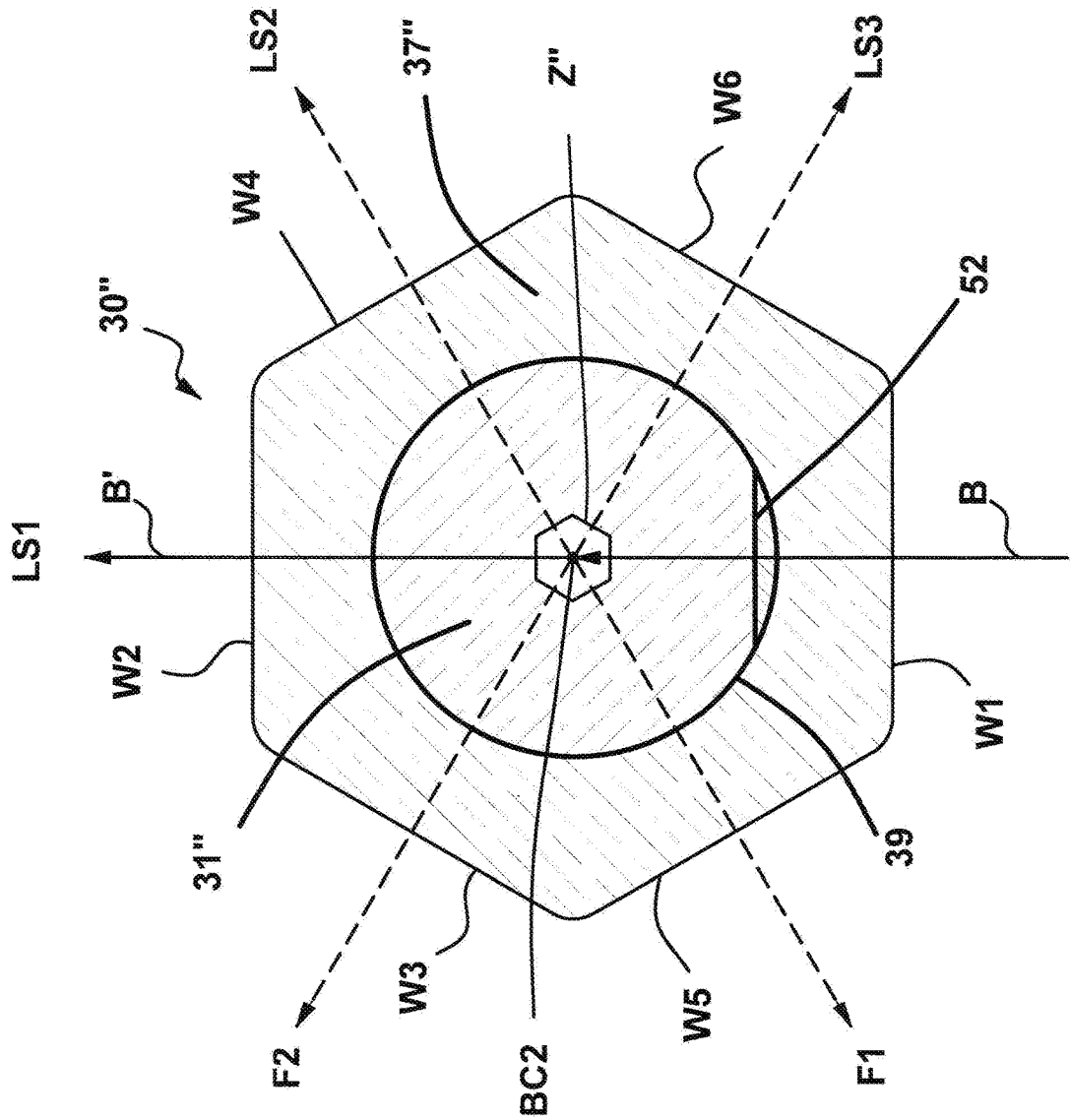
FIG. 10 illustrates a cross-sectional view through the six-sided parameter-acquisition zone of the compound optical flow cell of FIG. 9 and a manner of use.

The aforesaid commercial disadvantages of monolithic flow cells are herein addressed via compound flow cells fabricated according to a method of the present invention. As the following discussion of Table 1 will demonstrate, such method comprises improvements to the prismatic flow-cell art, is distinguished from other methods for making flow cells, distinguishes the product thereof from other flow cells including monolithic flow cells, and is generally applicable to a broad variety of flow-cell embodiments that retain the many proven cytometric advantages of monolithic flow cells while reducing the probability of aforesaid artifacts to which their method of fabrication is liable. Such method offers advantageously reduced costs and improved yields by providing at least two independent, mutually conforming, alignable elements made of insulative transparent material, the elements being then assembled and fixed together in a predetermined relation to form a flow cell having a compound structure through which optical parameters of formed bodies transiting an internal flow channel may be determined (e.g., flow cell 30 in FIGS. 3-6). A first element (e.g., 31 of flow cell 30 in FIGS. 4-6) is a substantially cylindrical monolithic element surrounding a seamless interior passageway (i.e., 32 in FIGS. 4 and 5), at least an axial portion of which (i.e., volumeter conduit Z in said figures) is surrounded by a continuous surface of preferably non-circular cross-section (i.e., Z in FIG. 6) to form a parameter-acquisition zone (i.e., Z in FIGS. 3-6). Such elements are preferably made as prismatic flow cells by processes that differ in key aspects from those described in the '187 patent; as will be discussed, such elements also comprise fewer oversleeve tubes than prismatic flow cells used to form comparable monolithic flow cells of the '187 patent. Element 31 of FIGS. 4-6 is preferably made by forming a volumeter conduit in an appropriate prismatic flow cell (e.g., element 31' of the flow cell in FIG. 7A or 7B) as described in the introductory portion hereof regarding the flow cell used in certain analyzers produced and sold by Beckman Coulter, Inc. The non-axisymmetric refractive effects originating in the cylindrical envelopes of such prismatic flow cells are herein optically improved not by machining an integral optical envelope thereon as for monolithic flow cells of the '187 patent, but by combining said prismatic flow cells with at least one independent second element (i.e., 37 in aforesaid figures) comprising both a concave surface conforming to said monolithic element (e.g., an interior cylindrical through-bore or portion thereof) and an exterior preferably non-cylindrical envelope having optical surfaces (e.g., planar optical flats 50) of predetermined orientation thereto as suited to the intended cytometric function. Said element 31 or 31' is assembled inside at least a portion of element 37, said conforming surface or portion thereof being positioned with respect to element 31 or 31', such spatial relationship being established via alignment of reference features on said elements (e.g., flat 52 on element 31 or 31' and a planar side 50 of element 37). Element 37 is then fixed to element 31 or 31' by optical join 39 so as to minimize non-axisymmetric refraction through the compound wall formed between a surface of respective passageway 32 or 32' in element 31 or 31' and the corresponding envelope surface 50 of element 37. Join 39 is preferably made with an optical joining material that is both substantially non-fluorescing and homogeneous optically with elements 31 or 31' and element 37, i.e., respective refractive indices $n_{31}(\lambda)$ or $n_{31'}(\lambda)$, $n_{37}(\lambda)$, and $n_{39}(\lambda)$ of the elements 31 or 31' and 37, and of the optical join material 39, are substantially equal. FIG. 3 flow cell 30 may also be made from compound flow cell 30' in FIG. 7A or 7B by forming a volumeter conduit in passageway 32' thereof in the aforesaid manner. Flow cell 30" in FIG. 11 differs from FIG. 3 flow cell 30 in having a hexagonal cross-section in both the parameter acquisition zone Z" and envelope as shown in FIGS. 9 and 10; its method of fabrication may be similarly illustrated by an analogous description of said figures. For both FIG. 3 flow cell 30 and FIG. 11 flow cell 30", the resulting structure thus generally comprises an internal passageway (e.g., 32 or 32") including a parameter-acquisition zone (e.g., Z or Z") through which aforesaid prepared samples can be metered and an external envelope (e.g., comprising surfaces 50 or 60) aligned thereto that is suited to acquisition of optical characterizing parameters from formed bodies in such samples as they transit said passageway. As will be apparent to those skilled in cytometric art, numerous compound flow-cell structures other than exemplary flow cells 30, 30' and 30" of the above-cited figures may be produced via the method herein described.

With reference to Table 1, advantages of flow cells according to the method of the present invention may be demonstrated with respect to glass-forming artifacts via comparison with similar monolithic flow cells made according to the '187 patent. Typical products of both methods preferably comprise a joinless monolithic element, or prismatic flow cell, having an internal seamless flow channel, or passageway, that surrounds and contains functional contents thereof and an optical envelope substantially coaxial thereto. As disclosed in the '187 patent, such monolithic element is fabricated as a preform made of an insulative transparent siliceous material caused to have an interior channel preferably bounded by three or more planar surfaces. Such preform is formed by collapsing a meticulously clean tube of insulative transparent material, preferably a form of silica ($SiO_2$) and most preferably synthetic amorphous silica made by a vapor deposition or sol-gel process, over a non-cylindrical mandrel having a cross-section similar to that of the desired final parameter-acquisition zone; such mandrel is prepared of a suitable material by standard machining operations to have the desired cross-section significantly larger than such zone as is known in the glass-forming art. In FIG. 8A, a mandrel M of square cross-section is shown inserted inside a silica tube T1 prior to the tube/mandrel pair being mounted on a lathe; while being rotated the tube is heated above its transition (or softening) temperature to produce a viscosity in the range between $60 \times 10^6$ and $1 \times 10^6$ poise, more preferably between $28 \times 10^6$ and $3 \times 10^6$ poise, and then collapsed onto the mandrel to begin a preform that will ultimately provide a parameter-acquisition zone of substantially square cross-section as shown in FIGS. 2, 4, 6, 7A, and 7B. Mandrels having other cross-sections may be used, e.g., FIG. 8B illustrates the finished collapse of such a tube T1' onto a mandrel M' for a preform suited to provide a parameter-acquisition zone of substantially hexagonal cross-section as shown in FIGS. 9 and 10; while generally not preferable, in some instances small radii R" on the mandrel corners may be beneficial. Following removal from the lathe, the mandrel is preferably removed from such collapsed first tube. Said first tube is then inserted into a larger silica sleeve tube of appropriate inner and outer diameters, and the tube pair mounted on a lathe where the sleeve tube is heated above its transition temperature while being rotated to attain a viscosity preferably in the range between $28 \times 10^6$ and $3 \times 10^6$ poise, thereby allowing its inner surface to be fused to the outer surface of the first tube comprising the axial channel formed by the mandrel. Such oversleeving step is repeated until a preform of sufficient outer diameter is formed; for a monolithic flow cell comprising a Coulter volumeter conduit, five or more oversleevings are typically required, with a cross-sectional ratio of mandrel area to envelope area preferably between $0.4 \times 10^{-4}$ and $5.1 \times 10^{-4}$ and most preferably about $1.5 \times 10^{-4}$. It may be preferred that a flat of sufficient width to provide a reference feature on the drawn preform (e.g., flat 52 on FIG. 4 element 31) be ground on the outer surface of the completed preform parallel to a channel surface. The preform is then appropriately cleaned, mounted in a conventional drawing tower, heated to a predetermined temperature sufficiently above its transition temperature that its viscosity permits deformation, and drawn downward in air at a constant angular orientation and at a controlled rate, preferably between 0.05 and 2 meters/minute, whereby the polygonal cross-sectional shape of the internal channel is maintained during the drawing operation and the desired cross-sectional area of reduced size is achieved in the axially extending channel. As a specific example, parameter-acquisition zone Z in FIG. 6 compound flow cell 30 may be compared with that of analogous monolithic flow cell 20' in FIG. 2. In FIGS. 2 and 6 are shown cross-sections through parameter-acquisition zone Z of the sample passageway in a four-sided flow cell; thus, these figures are equally representative of either a purely optical flow cell having a uniform square passageway (e.g., 32' in FIGS. 7A and 7B) or a flow cell enabling acquisition of both optical and Coulter parameters within a portion of such passageway comprising a volumeter conduit (e.g., 32 in FIGS. 4 and 5). Exemplars of the latter flow-cell type have the particle-sensing portion Z of such passageway in FIGS. 2 and 6 of width W' 52 micra and planar envelope sides 50 of width about 4.2 mm and length about 6.3 mm, which for prismatic flow cells useful in fabricating either monolithic and compound flow cells requires oversleeving and fusing multiple successive sleeve tubes of increasing diameter onto a first tube collapsed to contain a prismatic channel of substantially square cross-section. The probability of wall flatness being lost in parameter-acquisition zone Z in FIGS. 2 and 6, and of concentricity of the successive preform surfaces to the channel axis of Z, increases with the number of oversleeving steps, while the probability of airlines in the drawn preform increases with the total fusing area per unit length of preform (i.e., with the sum of the diameters of the several sleeve tubes). FIG. 2 monolithic flow cells 20' made from an exemplary prismatic flow cell comprising five sleeve tubes with fusing diameters reduced during drawing to 0.200, 0.436, 0.920, 2.440, and 4.812 mm, have a probability that is proportional to 5 for loss of concentricity and flatness of channel wall surfaces, but proportional to 8,808 per unit length for formation of airlines. Examination of FIGS. 2 and 6 will make apparent that for equal width of respective sides 50 therein, the wall thickness provided by independent conforming element 37 in FIG. 6 compound flow cell 30 reduces the number of sleeve tubes required to form element 31 to which it conforms, as compared to the prismatic flow cell required to permit machining the integral envelope of FIG. 2 monolithic flow cell 20'. As indicated in Table 1, it is feasible to form passageway 32, as described in introductory comments herein and shown in FIGS. 4 and 5, in elements 31 comprising three oversleeve tubes and having a 2.44-mm final outer diameter, thereby avoiding two oversleeving steps required by a comparable monolithic flow cell 20'. Thus, the probability of concentricity and flatness in channel wall surfaces being lost in such smaller preforms becomes proportional to 3, a 40% reduction, and proportional to 1,556 for formation of air lines, an 82% reduction. Such significant reduction in probability of all aforesaid artifacts arising in the oversleeving process is in itself advantageous, but as also indicated in Table 1, fewer oversleeving steps also facilitate drawing such smaller preforms at lower temperatures and greater viscosities. According to the '187 patent, prismatic preforms for use in monolithic flow cells were heated to drawing temperatures in the range between 1,610 C.° and 1,860 C.° to attain a viscosity in the range between $60 \times 10^6$ and $1 \times 10^6$ poise, with a smaller temperature range and a viscosity between $28 \times 10^6$ and $3 \times 10^6$ poise being more preferred. In contrast, the latter conditions are less preferred when drawing preforms intended for use as element 31 in compound flow cells; a cooler such draw at temperatures in the range between 1,500 C.° and 1,750 C.°, with a preform viscosity range between $1,000 \times 10^6$ and $6 \times 10^6$ poise, has been found to be most preferable. A portion of the final prismatic channel forms the critical parameter-acquisition zone Z of flow cells fabricated from segments cut from the drawn preform, e.g., 30 in FIGS. 4-6, 7A, and 7B, and such cooler drawing process offers improved control over flatness in channel surfaces thereof. As noted in Table 1, for aforesaid exemplary flow cells the average reciprocal radius of the best-fit circle over the central 28 micra of the four channel surfaces is 0.30 mm$^{-1}$ for prismatic flow cells made according to the method of the '187 patent (e.g., FIG. 2), compared to 0.19 mm$^{-1}$ for ones made according to the method of the present invention (e.g., FIG. 6); a truly flat surface has a reciprocal radius equal to zero. Both the reduction in number of oversleeving steps and the 37% reduction in channel-surface curvature favor better yields of prismatic flow cells providing desired optical performance, so requiring fewer selection processes during post-draw processing into compound flow cells and integration of these into transducer assemblies (e.g., such as T in FIG. 3 or T' in FIG. 11), with reduced costs and improved yields thereof.

Advantages may also be illustrated with respect to post-draw machining artifacts for flow cells according to the present invention. As previously noted, according to the '187 patent monolithic flow cells require improving prismatic flow cells by machining integral non-cylindrical envelope surfaces directly thereon, such improvement requiring appropriate alignment of secondary machining processes with either at least one channel surface within segments of a drawn preform or with a segment flat that was ground onto the preform substantially parallel to such a channel surface prior to the heating and drawing operations. Both alignments are difficult and require exceptional care if alignments to within less than about two angular degrees are to result. Additional variability arises via mounting techniques typically used during the secondary formation of planar envelope surfaces on prismatic flow cells, so that wall wedge angles (e.g., a between FIG. 2 flow-cell surface 50 and wall surface of Z) become more random, with tendency to become variably excessive. Separate optical components that individually comprise either wall surfaces of Z forming a desired channel cross-section or a finished envelope having a desired cross-section, such components being mutually conforming to each other and appropriately aligned one to the other in an assembly process, avoid the above-mentioned difficulties in improving prismatic flow cells. As an Internet search will demonstrate, prisms of many designs and spheres of many diameters, both of high precision and excellent surface quality in a variety of insulative transparent materials including silica ($SiO_2$), are commercially available from many suppliers of optical components. The independent control under which the optical surfaces of such conventional components are machined and finished to optical quality minimizes envelope variability by eliminating typical mounting and machining methods used during the aforesaid optical improvement required to convert prismatic flow cells into monolithic flow cells, while enabling a more-efficient analogous improvement via a compound, i.e., non-monolithic, structure that provides essential advantages of monolithic flow cells. Adapting an appropriate such commercial component to provide a suitable conforming element 37 (e.g., 37 in FIGS. 4, 7, 12, 14, and 15; 37' in FIG. 13; or 37" in FIG. 9) requires use of established glass-working methods to through-bore (or core) and finish such components so as to conform to a monolithic element 31 of the preferred length; less preferably, an appropriate portion of such a component may be form ground and finished to provide the conforming concave surface. A reference feature of prisms so machined (e.g., optical surface 50 in FIGS. 4-6, 7A, and 7B) or a flat surface formed parallel to the through-bore of such cored spheres as a window for an optical interrogation beam (e.g., 98 in FIG. 13C) can then be used to align such machined elements to either a channel surface in such cylindrical elements or a flat provided thereon prior to drawing the preform from which such cylindrical elements were separated (e.g., 52 in FIGS. 4, 6, 7A and 7B, and 10). Alignment of such conforming elements to cylindrical elements (e.g., 37 to 31 so as to minimize FIG. 6 wedge angle a) may use conventional optical methods of high precision (e.g., autocollimation) that are not readily adapted to the methods of the '187 patent. Such conforming and cylindrical elements are fixed in the aligned spatial configuration by bonding with an appropriate optical joining material (39 in aforesaid figures) to provide a flow cell of the invention; preferably, such bonding minimizes non-axisymmetric refractive effects across the cylindrical join via a joining material that is substantially non-fluorescing. Improved control over envelope geometry and surfaces thusly obtained, and the attendant facilitation of more-precise alignment of channel and envelope surfaces, both favor improved yields of flow cells giving desired optical performance with fewer selection processes during post-draw processing and integration into transducer assemblies (e.g., such as T in FIG. 3 or T' in FIG. 11).

Although both cylindrical monolithic elements and conforming annular elements (e.g., 31 and 37 of FIGS. 4-6) may be fabricated from a variety of optically clear materials, the unfavorable refractive index and other properties of many siliceous and most plastic materials make most preferable amorphous silica ($SiO_2$) synthesized through a chemical vapor deposition process or a sol-gel process and having a chemical impurity level less than 2600 ppm. Among advantageous properties such silica glass has exceptional transmission in the 250 to 400 nm wavelength range, very low intrinsic fluorescence, and excellent dielectric properties. Suitable silica tubes are available commercially in both standard and custom geometries; for the cylindrical monolithic elements 31 discussed herein, tubes have an inner diameter (ID) in the range between 2 and 30 mm, or more preferably between 6 and 20 mm, and an outer diameter (OD) in the range between 6 and 45 mm, or more preferably between 15 and 35 mm. The silica may contain dopants useful to adjust optical properties of the silica, e.g., refractive index, absorbance, or fluorescence, as well as physical properties such as softening point, strength, and stress distribution; for use in components described herein, it is crucial that any added dopants not induce fluorescence under irradiation by the interrogating radiation beam. In comparison to other silicate glasses, synthetically fabricated silica glass also has very good chemical resistance, low coefficient of thermal expansion, and very low concentration of defects. Furthermore, drawn silica structures such as the prismatic flow cells herein described have superior mechanical strength when compared to structures drawn from preforms fabricated from other glass types.

Elements of compound flow cells may be assembled and aligned via a variety of methods used in the electro-optical arts. After segments of a preferred length are conventionally cut from drawn cylindrical monolithic preforms and the cut ends thereof squared to acceptable perpendicularity, if necessary, such steps are preferably done using appropriate fixturing. As an example, such segments (e.g., 31 of FIGS. 4-6) may be mounted to a fixture so as to permit rotation about the axis of the internal flow channel and a reference feature thereof (e.g., the near wall of Z or flat 52) may be aligned perpendicular to the optical axis of an autocollimator, the cylindrical element then being secured in the oriented position. A conforming annular element (e.g., 37 of FIGS. 4-6) may be mounted with a reference feature (e.g., an envelope surface 50) in contact with a plate of the fixture, the surface of which is also perpendicular to the optical axis of the autocollimator, the plate and annular element then being moved so as to maintain said alignment while placing the annular element in the desired spatial relationship to the oriented cylindrical monolithic element (e.g., so that wedge angle a in FIG. 6 is acceptably minimized). With the said elements so aligned, a low-fluorescing optical adhesive, preferably UV-curable, is applied from a metering dispenser to the clearance space between the two elements; a regulated vacuum may be useful in achieving a complete fill so as to form a homogeneous optical join throughout the clearance space including that between any flat on the cylindrical element and the through bore in the annular element (e.g., 39 of FIGS. 4-6). The insulative transparent adhesive (e.g., Loctite 352) is most preferably cured prior to removing the flow-cell elements from the fixture. More preferably, after element 37 and optical joining material 39 are placed in final configuration on element 31 but prior to curing of the latter, element 37 is spatially positioned and aligned with respect to element 31 so as to limit non-axisymmetric refractive effects on optical parameters acquired on a predetermined acquisition axis (e.g., as illustrated by FIG. 4 laser beam B) from formed bodies passing through the parameter-acquisition zone Z in element 31 of flow cell 30. Most preferably, such positioning and alignment are done with the flow cell mounted in a test fixture also replicating the relevant portions of 18 or 18' in FIG. 3 or 11, i.e., provided with a laser 42 of appropriate wavelength as a radiation source, the laser's beam-shaping optics 62, and sufficient supporting fluidics to fill FIG. 4 passageway 32 with physiologic saline diluent; the interference pattern of the radiation passing through the parameter-acquisition zone of the filled flow cell may be projected onto a screen, or acquired via appropriate coupling optics and imaging sensor substituted for LSD1 and LSD2, and optimized by relative rotation between the two flow-cell elements to give a clean unimodal pattern as is known in the optical test art.

In view of the foregoing discussion it will be appreciated that the proven cytometric advantages of monolithic flow cells may be provided, with reduced commercial disadvantages arising in the fabrication processes thereof, via new flow cells structured and manufactured according to the method of the invention, i.e., compound flow cells comprising at least two elements made of insulative transparent material, preferably a form of synthetic amorphous silica ($SiO_2$). One element of such compound flow cells is preferably a prismatic flow cell similar to those that can be optically improved by the addition thereto of an integral non-cylindrical envelope to form a monolithic flow cell, but of simpler construction and lesser diameter. With reference to an exemplary flow cell, i.e., flow cell 30 in FIGS. 3-6, the first element (i.e., 31 in FIGS. 4-6) is monolithic, substantially cylindrical, and comprises a seamless internal flow channel (i.e., passageway 32 in FIGS. 4 and 5) at least an axial portion of which (i.e., volumeter conduit Z in last-said figures) is surrounded by a continuous surface of preferably non-circular cross-section (i.e., Z in FIG. 6) so as to define a particle-sensing zone (i.e., parameter-acquisition zone Z in FIGS. 3-6) for cytometric characterizing parameters. Other elements are annular in that they comprise both a concave surface conformed to first said element (i.e., preferably by an interior cylindrical through-bore or portion thereof adapted to receive said first element) and an exterior non-cylindrical optical envelope suited to the cytometric application and having a predetermined spatial relationship to said concave surface. For the dual-element embodiment 30 shown in FIGS. 4-6, annular conforming second element 37 comprises substantially planar optical surfaces 50 forming an optical envelope, encloses first element 31, and is optically bonded thereto by optical joining material 39. It is preferable that wedge angle a in FIG. 6 be minimized so that envelope surfaces 50 are made substantially parallel to the corresponding wall surfaces of parameter-acquisition zone Z in FIGS. 4 and 6, the wall between said surfaces thus forming an optical window of substantially uniform thickness so as to minimize non-axisymmetric refractive effects on optical parameters acquired on a predetermined acquisition axis (e.g., as illustrated by laser beam B) from formed bodies passing through parameter-acquisition zone Z in element 31 of flow cell 30. Minimization of such wedge angle may be facilitated by reference flat 52 formed on the preform surface parallel to a wall of the prismatic channel therein prior to drawing the preform. It will be appreciated that many embodiments of such flow cells other than exemplary flow cell 30 fall within the scope of the present invention (e.g., as shown in FIGS. 7A, 7B, 9, 12, 13A-13C, 14, and 15). Specifically, portions of one or more annular second elements may be used in lieu of the integral annular second elements illustrated in the several figures herein. Similarly, components of flow cells structured as described herein may, less preferably, be made of a glass other than a form of silica.

A preferred method for differentiating formed bodies using flow cells of the invention comprises the steps of: a) providing a flow cell of the type described herein that comprises at least two elements made of an insulative transparent material, the first element being a substantially cylindrical monolithic element that includes a seamless internal flow passageway at least an axial portion of which is surrounded by a continuous surface of preferably non-circular cross-section and the second element having both a concave surface conformed to such first element and an external non-cylindrical optical envelope of predetermined form and orientation, said second element being fixed to said first element by an optical join so as to minimize non-axisymmetric refractive effects in optical signals acquired through the compound walls (or windows) between corresponding surfaces of said passageway and said envelope; b) passing such liquid suspensions through a parameter-acquisition portion of the flow passageway while irradiating formed bodies therein with a beam of radiation passing through one of such walls; and c) detecting different optical parameters of the irradiated formed bodies through other of such walls. Preferably, such flow cell has at least three discrete walls (or windows) through two of which differentiating optical parameters of formed bodies in the parameter-acquisition zone can be sensed and, upon irradiating formed bodies therein with a beam of radiation passing through a first wall, forward-scatter radiation from the irradiated formed bodies may be sensed through a second wall and fluorescence characteristics of the irradiated formed bodies may be sensed through a third wall. More preferably, such flow cell has at least five discrete walls (or windows) through four of which differentiating optical parameters can be sensed and, upon irradiating formed bodies within the parameter-acquisition zone with a beam of radiation passing through a first wall, forward-scatter radiation from the irradiated formed bodies may be sensed through a second wall, back-scattered radiation from the irradiated formed bodies may be sensed through a third wall; fluorescence characteristics of the irradiated formed bodies may be sensed through a fourth wall; and side-scattered radiation from the irradiated formed bodies may be sensed through a fifth wall. As will be discussed, cytometric applications involving low-intensity optical signals, a second element having an envelope comprising a non-cylindrical surface of revolution, e.g., a spherical surface, is highly preferable. Most preferably, at least some of the aforesaid optical measurements are combined with Coulter volume V and/or conductivity C measurements simultaneously made on the irradiated formed bodies passing seriatim through the flow channel. Such differentiating parameters are correlated by conventional algorithms to provide desired diagnostic information.

An exemplary method of use for flow cells of the present invention will be first described for the embodiment of FIG. 3. Simultaneous acquisition of optical and Coulter V and/or C distinguishing parameters from an individual formed body in whole-blood samples requires that the parameter-acquisition portion Z of the sample passageway in FIG. 3 flow cell 30 be comparable in size to the formed bodies to be characterized, i.e., a constriction (or Coulter volumeter conduit) having relatively small cross-sections and lengths. Thus, if one or more Coulter parameters are desired, the flow channel width is typically 150 micra or less, with an axial portion of length typically between 0.75 and 2.0 times said width forming the volumeter conduit. Flow cells comprising such volumeter conduits typically have external envelopes of width between 4 and 8 mm and of length between 4 and 12 mm. To provide the exemplary flow-cell indicated in FIG. 3 and better illustrated in FIGS. 4-6, the parameter-acquisition portion Z in passageway 32 of flow cell 30 is four-sided, substantially square, and about 50 micra flat-to-flat, thus providing a cross-sectional area within parameter-acquisition zone Z of about 2,500 micra$^2$ within an envelope of which the respective width W of sides 50 is between 4 and 5 mm, or preferably about 4.2 mm, and the respective length L of each side 50 is between 6 and 10 mm, or preferably about 6.3 mm. As shown in FIGS. 4 and 5, passageway 32 extends between the opposing end surfaces 36 of flow cell 30 and is typically coaxial with the longitudinal axis A thereof; it contains liquid flows and Coulter excitation currents within a joinless flow channel formed by partially boring the original prismatic channel in cylindrical monolithic element 31 from both ends through the end surfaces thereof to form an hour-glass shape having cylindrical bores 54 (e.g., of diameter about 1.2 mm) and surfaces of revolution 55 (e.g., of radius about 600 micra) providing a smooth transition from said bores to a short length of original prismatic channel left in situ, i.e., parameter-acquisition portion Z in FIGS. 4 and 5. Most preferably, lengths for Z in flow cell 30 range between about 1.3 to 1.5 times the width of the channel, or between about 65 and 75 micra for the present preferred embodiment. Such passageway 32 may be formed in a cylindrical element 31 of 2.44-mm outer diameter and is preferably formed therein prior to assembly and joining of such element with conforming element 37; however, passageway 32 may also be formed after such assembly and joining, e.g., in an appropriate cylindrical element 31' of flow cells 30' in FIGS. 7A and 7B. Portion Z of the original prismatic channel thus defines in the vicinity of the axial midpoint of passageway 32 in FIGS. 4 and 5 a Coulter volumeter conduit of uniform polygonal cross-section, as shown in FIG. 6, within which the Coulter DC volume (V) and RF electrical conductivity (C) parameters of individual passing formed bodies can be determined. Moreover, the wall formed between aligned substantially planar wall surfaces of volumeter conduit Z and planar optical envelope surfaces 50 of flow cell 30 provides windows of uniform thickness that are well-suited to coupling an interrogating laser beam B into volumeter conduit Z for interaction with formed bodies therein and simultaneously also determining their aforesaid absorption of radiation (A), various light-scattering (S) properties [i.e., forward scatter (FS), side scatter (SS), and/or back scatter (BS)], and fluorescence properties (F). It will be understood that different volumeter lengths or passageways comprising longitudinal sections of other geometries may be advantageous in some applications. Some cytometric applications may require the interrogating radiation beam B to pass through particle-sensing zone Z parallel to reference surface 52 formed on cylindrical element 31 as shown in FIGS. 4 and 7A, while in others said beam B may pass substantially perpendicularly through such surface as shown in FIG. 6.

As has been noted, end surfaces 36 of flow cell 30 in FIGS. 4 and 5 are sealingly attached to cap elements 34 or 35 of FIG. 3 transducer assembly T so as to be fluidically coupled to the internal chambers therein; cap elements 34 and 35 are provided with a respective plurality of ports P1-P3 and P4-P6 which are fluidically coupled to other components of CA. Port P1 is fluidically coupled to the metering component 16 and serves to provide metered aliquots of sample $S_L$, $S_D$, or $S_T$, as selected by distribution valve DV, to FIG. 3 sample inlet tube 56 for injection into passageway 32 of flow cell 30. In FIG. 5, sample inlet tube 56 (which is only partially shown) has a channel C1 into which port P1 couples a volume of sample delivered under pressure from metering pump MP4 of FIG. 3; channel C1 serves to project a sample stream 74 towards particle-sensing zone Z. Port P2 is also fluidically coupled to the metering component 16 and serves to introduce metered volumes of a sheath liquid S1, under pressure by metering pump MP4, into the chamber in cap element 34. As shown in FIG. 5, sheath liquid S1 uniformly surrounds sample stream 74 and causes the sample to flow through the center of volumeter conduit Z, thus hydrodynamic focusing sample stream 74 through the volumeter conduit. The exiting stream 76 and sheath liquid S2 from metering pump MP5 are collected by FIG. 3 sample exit tube 58 (illustrated only partially in FIG. 5), thus preventing formed bodies from recirculating into the conduit's ambient electric field in the chamber in cap element 35 and thus interfering with determinations of Coulter DC volume (V) and RF electrical conductivity (C). In FIG. 5, a first blood cell BC1 is shown after exiting the channel in inlet tube 56, a second blood cell BC2 is shown in the center of volumeter conduit Z and in the path of focused laser beam B, and a third blood cell BC3 is shown entering the sample exit tube 58, which is connected to waste through port P4 in FIG. 3. To control fluid pressure in the chamber in cap 35 and thereby control the flow of sample after it exits passageway 32, said chamber is maintained full of sheath liquid S2, such liquid entering through port P5 and draining to waste through port P4. Following data acquisition from each sample, transducer assembly T is prepared for another sample by flushing the chambers in cap elements 34 and 35 with sheath liquid, respectively, S1 from MP4 into port P2 and out of port P3 and S2 from MP5 into port P5 and out of port P6.

As shown in FIG. 3, within the interior chambers in cap elements 34 and 35 are respective internal electrodes 40 and 38 that are operationally connected to a DC/RF circuit 41. Materials for electrodes, and electrode extensions through the walls of said chambers in cap elements 34 and 35 to form operative connections with DC/RF circuit 41, are preferably selected from a group of chemically inert materials including palladium or platinum; however, in some applications other materials, even well-passivated stainless steel (e.g., 316 alloy), may serve. The components of DC/RF circuit 41 operate to (a) produce DC and RF currents through FIG. 4 passageway 32 of flow cell 30, and (b) to detect modulations in the respective DC and RF currents produced by the passage of formed bodies through particle-sensing zone Z simultaneously with the DC and RF currents, whereby the Coulter DC volume V of a formed body may be determined, as well as its RF conductivity C. As more-fully described in the '652 patent, DC/RF circuit 41 comprises a DC current source, an AC oscillator/detector operating at a RF frequency, a coupling circuit, and preamplifiers. The coupling circuit linearly combines the currents produced by the DC source and the AC oscillator/detector, and applies the combined current to contents of passageway 32 in transducer assembly T, as previously described. Preferably, the AC component has a frequency of about 22.5 MHz. As formed bodies pass seriatim through volumeter conduit Z, the impedance of passageway 32 is altered, resulting in a modulation of the DC current as a function of the body's physical volume V (i.e., the DC volume) and a modulation of the RF current as a function of the cell's internal conductivity C. The coupling circuit separates the modulated currents such that a DC pulse signal V is conveyed to a DC preamplifier, and the modulated RF current is detected by the oscillator/detector, resulting in a pulse signal C which is conveyed to the RF preamplifier. Preferably, both Coulter V and C pulse signals are coupled to the analyzing component of the cytometric analyzer, but for some applications, only one of such signals may suffice. Alternatively, other applications may benefit by inclusion in RF/DC circuit 41 of a plurality of AC circuits such as here described, each operating at a different frequency.

As each formed body transits volumeter conduit Z in FIGS. 3-6, it is irradiated by passing through a focused laser beam B of appropriate energy distribution as provided by a suitable laser 42 and beam-shaping optics 62 in transducer module 18. A transducer module adaptable to such use is described in commonly assigned U.S. Pat. Nos. 8,094,299 and 8,339,585, incorporated herein in entirety and hereinafter referred to as the '299 patent or '585 patent. Laser 42 may be of any appropriate type (e.g., a diode laser as provided in said patents) providing radiation of a wavelength suited to the cytometric application, e.g., radiation in the 635 to 640 nm wavelength range if scatter (S) parameters are of primary interest or in the 485 to 490 nm wavelength range if certain fluorescence (F) parameters are also required. Radiation (light) scattered by each formed body may be sensed by one or more light-scatter photo-detectors (e.g., LSD1-LSD3) and fluorescent radiation, if any, emitted by the formed body's fluorescent stain or fluorescent label as a result of being excited by the laser radiation, may be sensed by one or more fluorescence detectors (e.g., FD1-FD3). In the longitudinal section of flow cell 30 shown in FIG. 5, said laser beam B is focused by said beam-shaping optics to provide an elliptical bi-directional Gaussian distribution of radiation centered on volumeter conduit Z with the major axis of the elliptical distribution perpendicular to the sample flow and preferably between 12 and 15 micra in height, but beam-shaping optics structured to provide a focused line of lesser width and uniform radiation intensity across said conduit is preferable in applications requiring smaller coefficients of variation in acquired optical parameters. It will be appreciated that multiple such shaped laser beams from one or more lasers may interrogate individual formed bodies within the typical Coulter volumeter conduit. In the cross-sectional view of flow cell 30 shown in FIG. 6, one such beam enters the forward wall surface of volumeter conduit Z, encounters blood cell BC2 in the optical sensing zone, and causes side-scatter radiation SS and fluorescent radiation F to pass through the opposing walls of volumeter conduit Z parallel to optical axis OA, while forwardly scattered light FS and axially absorbed light A (not shown in FIG. 6) pass through the rear wall of particle-sensing zone Z along optical axis OA. It will be understood that the bonding material used to form join 39 between aforesaid FIG. 6 elements 31 and 37, as well as to fill the space between flat 52 of such element 31 and the conforming surface of such element 37, must be of optical quality, appropriate refractive index, and minimal fluorescence when cured.

As noted above and as more fully described in the '652 and '585 patents, radiation (light) scattered from focused laser beam B by formed bodies, passing seriatim through such beam within particle-sensing zone Z of flow cell 30 as shown in FIGS. 5 and 6, is detected by light-scatter photo-detectors, e.g., LSD1 and LSD3 in FIG. 3. Detector LSD1 is structured and located to detect light scattered in a forward direction within a total angular range between approximately 9 degrees and 41 degrees of said beam's axis. This detector has two discrete photoactive regions, OS1 and OS2, to detect forward-scattered light in the angular ranges between about 21 and 41 degrees, referred to as upper median-angle light scatter (UMALS), and between about 9 and 20 degrees, referred to as lower median-angle light scatter (LMALS). Additionally, the signals from OS1 and OS2 are summed to detect light scattered within the angular range between approximately 9 and 41 degrees, referred to as median-angle-light scatter (MALS). Thus, LSD1 provides three forward-scatter (FS) signals, i.e., MALS, UMALS, and LMALS. Moreover, further to description in the '652 patent, LSD1 also includes a center opening through which both the laser beam emerging from flow cell 30 and light scatter at less than about 8 degrees pass unobstructed as beam B1. Photo-detector LSD2 is appropriately located behind LSD1 and has two discrete photo-active regions, OS3 and OS4, which are structured to detect light scattered at about 5.1 degrees, referred to as Low Angle Light Scatter (LALS), and the near-axial attenuation in B1, referred to as Axial Light Loss (ALL). Thus, detector LSD2 provides two additional signals for analysis, i.e., a fourth FS signal, referred to as LALS, and the absorption (A) signal, referred to as ALL. Detector LSD3 is located to detect light scattered in a direction substantially normal (i.e., at about 90 degrees±about 10 degrees) to the axis of beam B, through one of the two lateral faces of flow cell 30. Detector LSD3 preferably comprises a lens 85 which collects and directs side-scattered light onto a PIN diode OS5 or the like and provides one side-scatter (SS) signal. It is understood that any of aforesaid sensors may be structured to respond to radiation within other angular ranges. It is also understood that, if desired, a fourth photo-detector, structured similarly to LSD1 and suitably located between beam-shaping optics 62 and flow cell 30, would provide back-scatter (BS) signals from formed bodies in particle-sensing zone Z. Free-space coupling between laser 42 and beam-shaping optics 62, between beam-shaping optics 62 and flow cell 30, and between flow cell 30 and the several photo-detectors is shown in FIG. 3, but it is understood that in some embodiments fiber-optic coupling may advantageously replace such free-space coupling between any of such-functioning elements in transducer module 18.

Fluorescent radiation results when light at an appropriate irradiation wavelength stimulates light emission from fluorescent moieties at one or more different wavelength(s); as noted above, such moieties may be attached to or inserted into various formed bodies as is known in sample-preparation protocols for use with conventional fluorescence flow cytometers. As more-fully described in the '652 patent, fluorescent radiation from such formed bodies passing through aforesaid radiation beam B in particle-sensing zone Z of flow cell 30 is collected by plano-convex lens 51. Lens 51 is preferably coupled (e.g., by an optical cement or a gel of appropriate refractive index and having minimal fluorescence) to the lateral face of flow cell 30 opposite that through which side-scattered light is detected by LSD3, such lens functioning to optically couple fluorescent radiation out of cell-sensing zone Z to a second lens assembly 70 which relays it, through a network of beam-splitting dichroic mirrors BS1 and BS2 and band-pass filters 71, 72, and 73, to a plurality of fluorescence detectors FD1, FD2, and FD3, which may be photomultiplier tubes or the like. If radiation beam B originates from a laser 42 operating at, e.g., 488 nm, said network may for example be conventionally designed to couple, in the most efficient manner, light at 525 nm, 575 nm, and 695 nm to fluorescence detectors FD1-FD3. In a conventional manner, each fluorescence detector detects fluorescent radiation in such predetermined wavelength range according to the optical properties of the dichroic mirrors and filters preceding it and converts said radiation into corresponding electrical signals. It is understood that the network of beam-splitting dichroic mirrors and band-pass filters may be extended, to allow additional fluorescence detectors to provide signals at additional wavelengths from formed bodies in particle-sensing zone Z, or that in some embodiments fiber-optic coupling may advantageously replace free-space coupling between any of the optical elements in transducer module 18.

FIG. 9 illustrates another flow cell 30" adapted for use in other embodiments of the FIG. 3 instrumentation. As for FIG. 3 flow cell 30, FIG. 9 flow cell 30" comprises a cylindrical monolithic element 31", most preferably made of synthetic amorphous silica ($SiO_2$), and an optical second element 37" conforming to and fixed thereto by an optical join 39 according to the method of the present invention. A central particle-sensing zone Z", of a cross-section bounded by six planar surfaces 64 about 55 micra from their opposing surface, extends for about 70 micra along the longitudinal axis A of flow cell 30" to form a volumeter conduit between surfaces of revolution 55 and bores 54 within passageway 32" formed between planar end surfaces 36" as described for FIG. 3 flow cell 30. Opposing planar end surfaces 36" are similarly coupled into the supporting transducer assembly and fluidic circuit as described for end surfaces 36 of FIG. 3 flow cell 30, and Coulter V and/or C characterizing parameters are acquired from formed bodies passing through the volumeter conduit in passageway 32" as has also been described. However, its structure makes flow cell 30" more versatile than flow cell 30 of FIG. 3. The envelope of FIG. 9 flow cell 30" is also prismatic in form, being bounded by six lateral sides 60 of rectangular shape, and the aforesaid pair of opposing planar end surfaces 36" of hexagonal shape. Preferably, the respective hexagonal cross-sections of particle-sensing zone Z" and the envelope of flow cell 30" are substantially similar and coaxial, the six planar surfaces 60 defining the lateral boundary of said envelope being arranged during optical joining of said elements 31" and 37" to be substantially parallel to the respective six planar surfaces 64 of particle-sensing zone Z" as shown in FIG. 10. Said cross-sections being thus aligned, e.g., via use of flat 52 on cylindrical element 31", six walls of predetermined uniform thickness and forming flat windows are provided for introducing a beam of radiation into particle-sensing zone Z" and for coupling such radiation out of said particle-sensing zone after interaction with formed bodies passing seriatim through it, thereby optical characterizing parameters may be simultaneously acquired with aforesaid Coulter V and/or C parameters. In FIG. 10 a cross-section through the particle-sensing portion of the sample passageway in a six-sided flow cell 30" is shown; thus, FIG. 10 is equally representative of a purely optical flow cell having a uniform hexagonal flow channel or one enabling acquisition of both optical and Coulter parameters within a portion of such channel forming a volumeter conduit as shown in FIG. 9.

In the introductory portion hereof was noted the complexity in FIG. 3 transducer module 18 required to conventionally acquire several optical characterizing parameters through a single flow-cell window, e.g., the aforesaid network of beam-splitting dichroic mirrors BS1 and BS2 and band-pass filters 71, 72, and 73 to acquire multiple fluorescent parameters in FIG. 3 transducer module 18. Such complexity can be reduced via a method of use for flow cell 30" of FIGS. 9 and 10. In FIG. 10 laser beam B passes through window W1 to irradiate a formed body BC2 transiting the particle-sensing zone Z" in a direction perpendicular to the plane of the drawing. Absorbance (A) of beam B by irradiated formed body BC2 is determined from the intensity of the partially absorbed beam B' passing through window W2, e.g., by the OS4 portion of FIG. 3 photo-detector LSD2. Forward light scattered by the irradiated formed body is measured at two different angles (LS1 and LS2) through windows W2 and W4, e.g., LS1 through window W2 by one or more photoactive regions OS1, OS2, and OS3 of FIG. 3 photo-detectors LSD1 and LSD2; and LS2 through window W4 by suitably-located photoactive region OS5 of FIG. 3 photo-detector LSD3. Fluorescence radiation emitted at different wavelengths may be measured through one or more of the remaining windows W3, W5, and W6 via complete or partial replications of the collection and wavelength-separation network for fluorescence described in connection with the FIG. 3 embodiment. However, in many applications requiring fluorescence measurements such elaboration is not needed and, via the additional sides to the internal sensing zone and envelope of flow cells such as shown in FIGS. 9 and 10, multiple fluorescence parameters can be measured separately through a dedicated window, thus avoiding the practical complications due to serial beam-splitters BS1 and BS2 in the fluorescence detection path shown in FIG. 3. In such embodiments, F1 and F2 are measured through windows W3 and W5 respectively, e.g. by suitably-located replications of FIG. 3 lens 51, lens assembly 70, filter 73, and fluorescence detector FD3, but without BS1 and BS2 in the optical path. Light at low back-scattering angles is shown exiting window W6 but, if preferable, fluorescence radiation at a third wavelength could be measured through this window by a replication of FIG. 3 lens 51, lens assembly 70, filter 73, and fluorescence detector FD3.

Figure 7B:
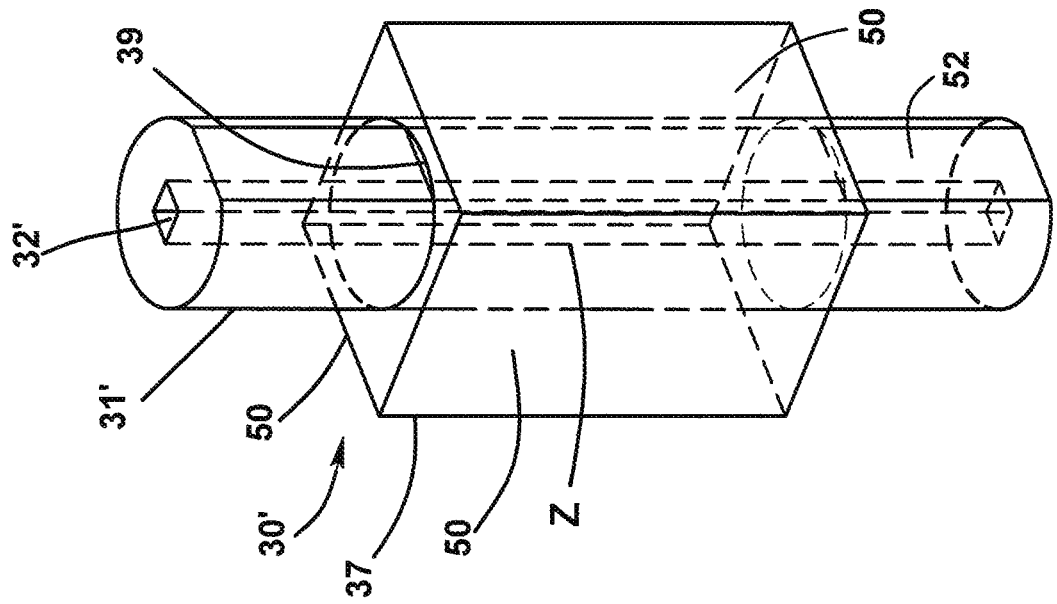
FIGS. 7A and 7B illustrate four-sided compound optical flow cells manufactured in accordance with the method of the invention and providing solely optical characterizing parameters.
Figure 7A:
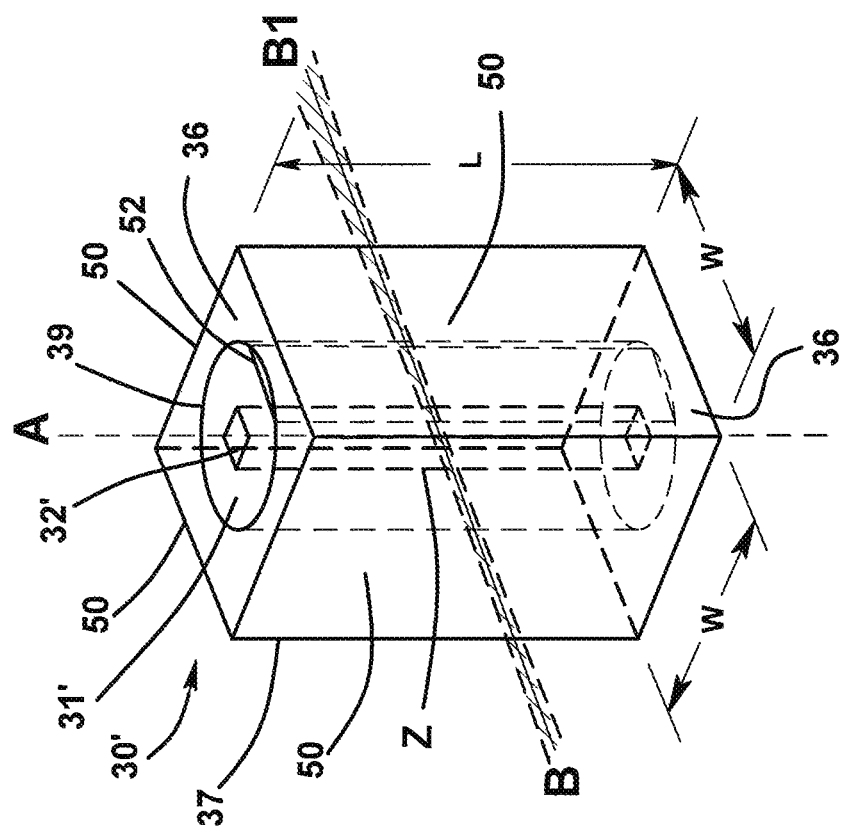
Figure 8B:
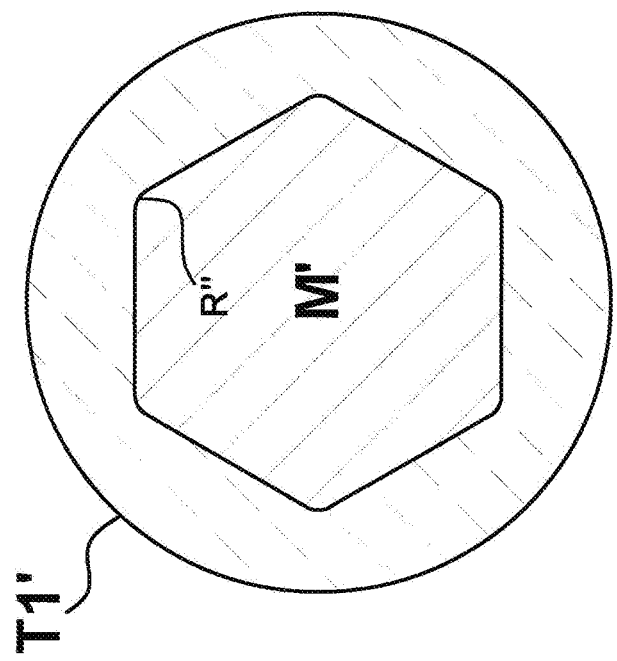
FIGS. 8A and 8B illustrate two steps of a preferred process for making a preform of the type used in producing the cylindrical monolithic element of compound optical flow cells of the invention.
Figure 8A:
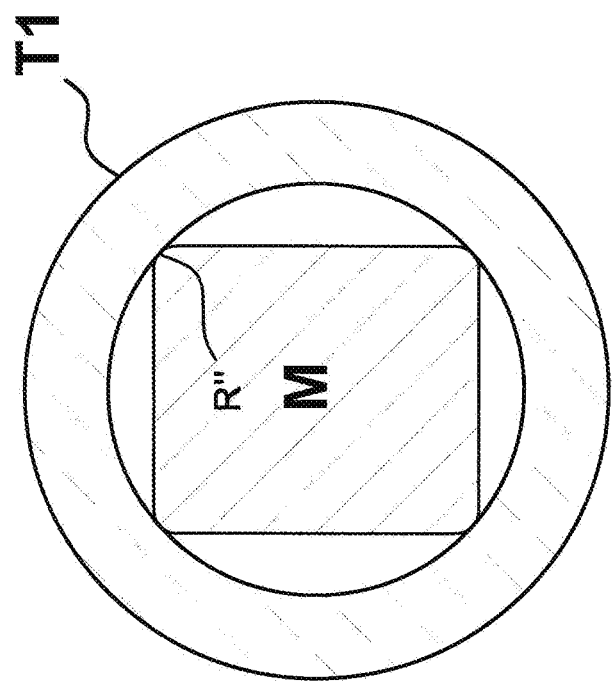

One such transducer module 18', for clarity of illustration relying solely on optical parameters, is illustrated in FIG. 11, where labels repeated from FIG. 3 have identical meanings and functions as indicated in discussion related thereto and where flow cell 30" is understood to be a purely optical flow cell having an appropriate sample passageway of uniform hexagonal cross-section, e.g., analogous to square passageway 32' in flow cells 30' in FIGS. 7A and 7B. In such applications absence of a Coulter volumeter conduit makes adequate post-analysis sample flushing of transducer assembly T' easier to achieve as has been discussed, so in addition to FIG. 3 Coulter electrodes 38 and 40 and RF/DC circuit 41, second sheath S2, its metering pump MP5, and associated ports P3, P5, and P6 in cap elements 34 and 35 of transducer assembly T do not appear in FIG. 11. Laser excitation beam B from laser 42 and beam-shaping optics 62, or their fiber-coupled beam-shaping equivalent, enters one window of FIG. 11 flow cell 30" and exits a second window opposite the first, after being scattered by formed bodies in prismatic flow channel Z". Signals responsive to radiation scattered by or resulting from the interaction of laser beam B with individual formed bodies are acquired in a direction substantially perpendicular to the other windows by appropriate sensors. Forward-scattered light is intercepted by photo-detectors LSD1 and LSD2 as described for the FIG. 3 embodiment, so producing analogous forward-scattered (FS) signals. Fluorescence radiation emitted by fluorescent moieties on or within the formed bodies (F1 and F2 in FIG. 10) is intercepted by at least one of suitably-located fiber-optic collection modules 75 and 77 through a third window (W3 or W5 in FIG. 10) and coupled to fluorescence detectors FD5-FD14 in FIG. 11 via fiber optics 80; examples of such fiber collection and coupling arrangements appear in commonly assigned U.S. Pat. Nos. 6,869,569 and 6,922,241, contents of which are incorporated herein in entirety by reference. Alternatively, such fluorescence interception and conversion to electrical signals may be accomplished with free-space optic coupling such as illustrated in FIG. 3, appropriately located to efficiently collect emitted fluorescence. Low-angle side-scattered light (LS2 through a fourth window W4 in FIG. 10) may be intercepted by suitably-located FIG. 11 collection lens 85 and photo-detector LSD3 for conversion by the photoactive region OS5 of the latter into a side-scatter (SS) signal. Similarly, low-angle back-scattered light (LS3 through a fifth window W6 in FIG. 10) may be intercepted by a suitably-located combination of a collection lens (not shown, to minimize confusion) and FIG. 11 photo-detector LSD4 for conversion by the photoactive region OS6 of the latter into a side-scatter (SS) signal; if preferable, fluorescence radiation at a third wavelength could instead be measured through this window by a third suitably-located fluorescence collection and transduction arrangement such as described above. It is understood that directly back-scattered light could be measured through FIG. 10 window W1 in much the same manner as described above for the embodiment in FIG. 3. If Coulter parameters V and/or C are desired, FIG. 11 flow cell 30" must comprise passageway 32" comprising a volumeter conduit between appropriate surfaces of revolution 55 and bores 54 as shown in FIG. 9; in addition, transducer assembly T' will require FIG. 3 electrodes 38 and 40 operatively connected to DC/RF circuit 41, metering pump MP5 and sheath S2, and some or all of ports P3, P5, and P6; all said components function as described for the exemplary embodiment illustrated in FIG. 3. It is understood that embodiments according to FIG. 9, but suited to particular cytometric applications, may benefit from having either more or less than the six windows illustrated therein, i.e., compound optical flow cells having similar polygonal cross-sections through the particle-sensing portion of their sample passageways and their envelopes aligned as described but having, e.g. three, five, seven, or eight windows.

Respective transducer modules 18 and 18' of FIGS. 3 and 11 develop scattering and fluorescence characterizing parameters resulting from interaction of an interrogating radiation beam B with individual formed bodies transiting seriatim through the parameter-acquisition portion Z of the flow passageway in flow cell 30 or 30". As is known in the cytometric art, formed bodies may also be differentiated into subpopulations via distinguishing characteristics captured in images obtained during their passage through such a beam; transducer assemblies T or T' comprising flow cells made and structured according to the present invention may be used with coupling optics and an appropriate imaging sensor in lieu of other sensor arrangements, e.g., of LSD1 and LSD2 in transducer modules 18 or 18'. Differentiating parameters derived from formed-body images so acquired can materially facilitate cytological and diagnostic determinations of broad clinical interest when processed alone by conventional correlation algorithms or, more preferably, so processed in combination with other characterizing parameters discussed in the preceding examples.

Instrument embodiments analogous to either FIG. 3 or FIG. 11 may comprise flow cells structured differently than flow cells 30 or 30" shown therein. For example, FIGS. 7A and 7B are perspective illustrations of four-sided flow cells 30' producible by the method of the invention. Flow cells 30' have rectilinear uniform passageways 32' in element 31' and, as noted above, are useful in embodiments of the FIG. 3 instrumentation that rely solely on optical properties to differentiate formed bodies into subpopulations. In such embodiments distinguishing parameters are acquired in the aforesaid manner from formed bodies passing seriatim through FIG. 3 laser beam B within particle-sensing zone Z while transiting an appropriately dimensioned square flow channel 32' in flow cell 30' as shown in FIG. 6. Element 31' may have a diameter of about 1.5 mm or greater; prismatic flow cells suited to use as such elements, of various lengths and having flow channels 32' of 47, 52, 65, 75, 100, 140, or 250 micra between their planar channel surfaces, have been fabricated. Alignment of reference features of elements 31' and 37 (e.g., flat 52 on element 31' with optical surfaces 50 of element 37) during assembly of flow cell 30', or assembly of a completed flow cell 30' in a transducer assembly, may be facilitated if element 31' is of a length greater than element 37 as shown in FIG. 7B. Passageway 32' of element 31' may be provided an hour-glass shaped passageway as described above for passageway 32 of flow cell 30 in FIGS. 4 and 5 prior to such assembly, in which operation flat 52 provides a reference surface for fixturing during the necessary machining of passageway 32'. If desired, extensions of element 31' beyond element 37 may be removed following alignment and fixing of the latter element to element 31'. Alternatively, flow cells 30' of FIGS. 7A and 7B, comprising a passageway 32' of desired dimensions in element 31' of appropriate diameter (e.g., about 2 mm or greater) and element 37 aligned and fixed thereto comprising optical surfaces 50 of desired width and length, may be further processed into flow cells 30 for use in the FIG. 3 instrumentation by forming a Coulter volumeter conduit in passageway 32' as has been described. Flow cells so made to comprise a volumeter conduit Z of 52-micra width and 70-micra length in an envelope having optical surfaces 50 of appropriate width and length are suited to use in certain hematology analyzers made and sold by Beckman Coulter, Inc. The flow-cell structures of FIGS. 7A and 7B may be adapted in an obvious manner to provide analogous flow cells 30" of FIG. 9 or 11 by the method of the invention, i.e., through use of appropriate elements 31" and 37".

Figure 12:
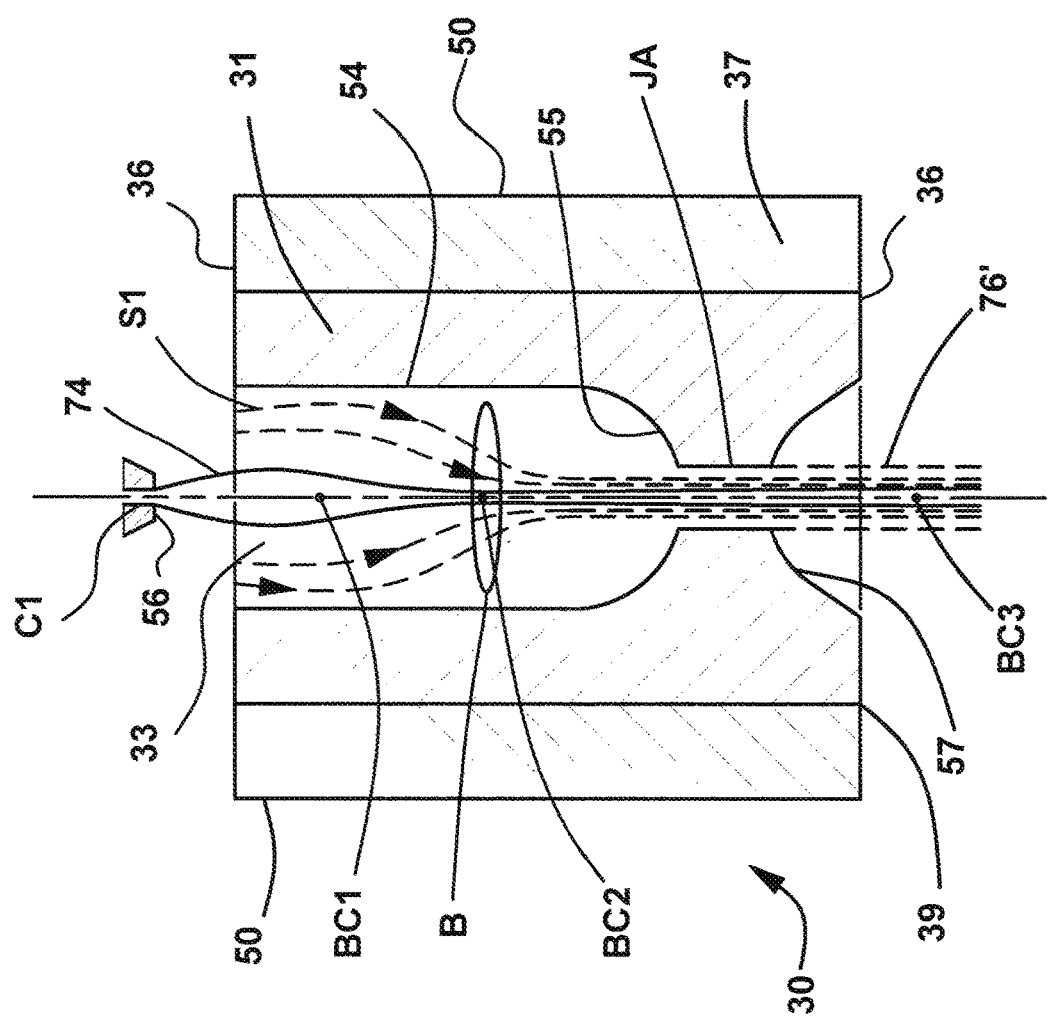
FIGS. 12, 13A-13C, 14, and 15 illustrate various views of other compound optical flow cells made by the method of the invention.

Downward flows through transducer assemblies are typically used in flow cytometers that sort selected formed bodies in a sample into individual receptacles according to their distinguishing characteristics. FIG. 12 illustrates a longitudinal section including the flow axis of another flow-cell embodiment useful in a flow cytometer that relies solely on optical properties of formed bodies (e.g., BC1-BC3) passing seriatim through laser beam B to differentiate and sort selected subpopulations according to their characterizing parameters, e.g. certain cell sorters made and sold by Beckman Coulter, Inc. FIG. 12 flow cell 30 is of similar size and structure as exemplary flow cell 30 of FIGS. 4-6 and may also be fabricated from flow cell 30' in FIG. 7A, jetting aperture JA therein being formed by the methods used to form volumeter conduit Z of flow cell 30 in FIG. 4. FIG. 12 flow cell 30 is sealingly attached and fluidically coupled only via its upper end surface 36 to FIG. 11 cap element 34, cap element 35 and its port P4 being unneeded; except for the downward flows indicated therein, items in FIG. 12 labeled identically to ones in FIG. 5 function in like manner, i.e., sample stream 74 is projected toward JA by channel C1 in inlet tube 56 and is surrounded by sheath liquid S1 in passageway 33 as has been described. Passageway 33 differs from FIG. 5 passageway 32 in having a longer bore 54 through upper end surface 36, so that the portion of original square channel forming jetting aperture JA is located close to the lower end surface 36 which, as noted, is unattached to instrument fluidics. Jetting aperture JA is a portion of the original prismatic passageway, of 75 by 75 micra cross-section, about 500 micra long between surfaces of revolution 55 and 57 and within a square envelope comprising planar surfaces 50 about 4 mm in width by 6 mm in length. Composite stream 76' of outer sheath and central sample streams exits through jetting aperture JA to form a jet in air. Although laser beam B is shown interrogating formed body BC2 in the sample stream above jetting aperture JA, it may be advantageous in some applications to couple the laser beam B as described for FIG. 3 instrumentation, i.e., through the flow-cell wall surrounding jetting aperture JA, so that optical sensing occurs within the jetting aperture itself. Alternatively, one or more laser beams B may be focused along the jet emerging from aperture JA, thereby allowing sequential acquisition of characterizing parameters from formed bodies (e.g., BC3) in stream 76' as in certain sorting flow cytometers made and sold by Beckman Coulter, Inc. Regardless of the specific optical interrogation method, drops containing desired formed bodies can then be electrostatically deflected in the conventional manner according to the characterizing parameters sensed by conventional optical transduction methods.

Figure 13:
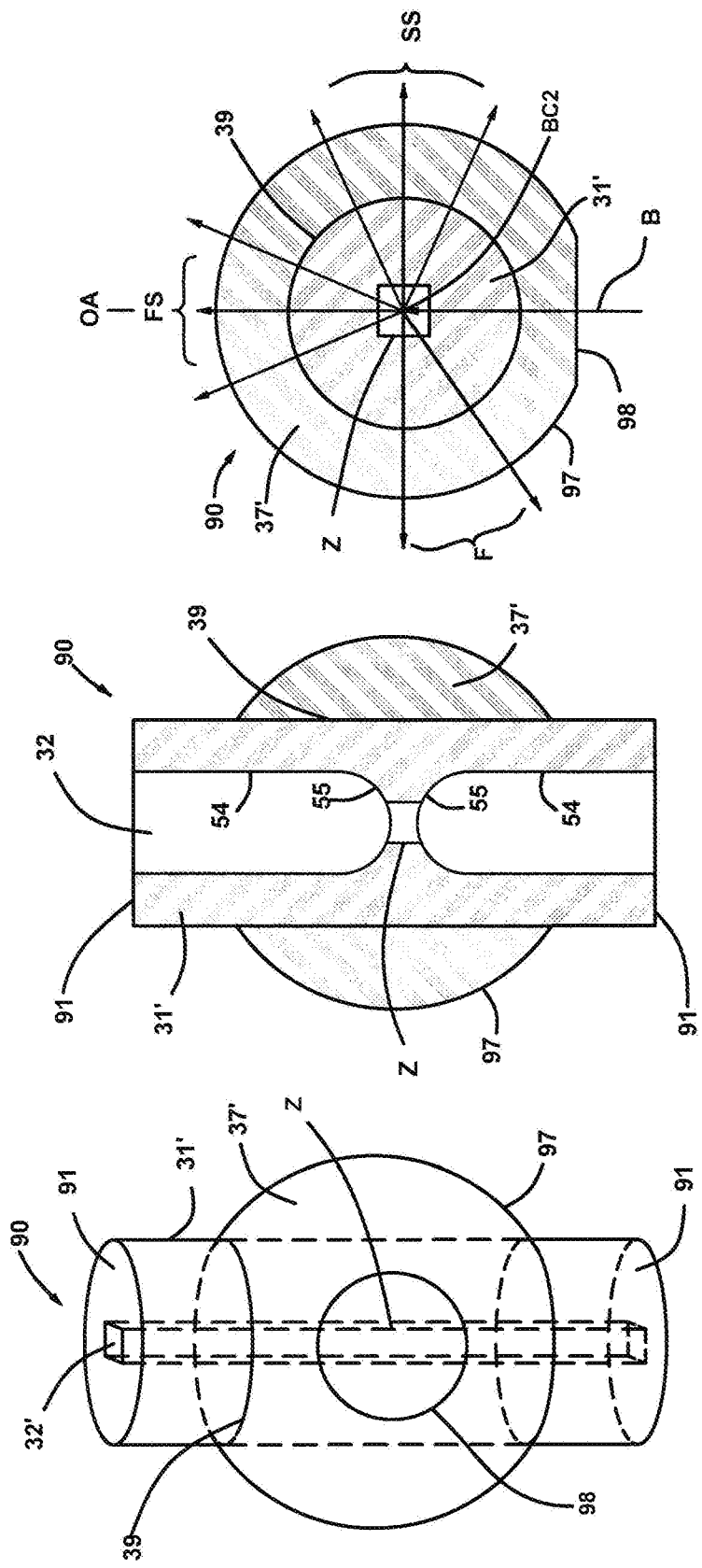
Figure 14:
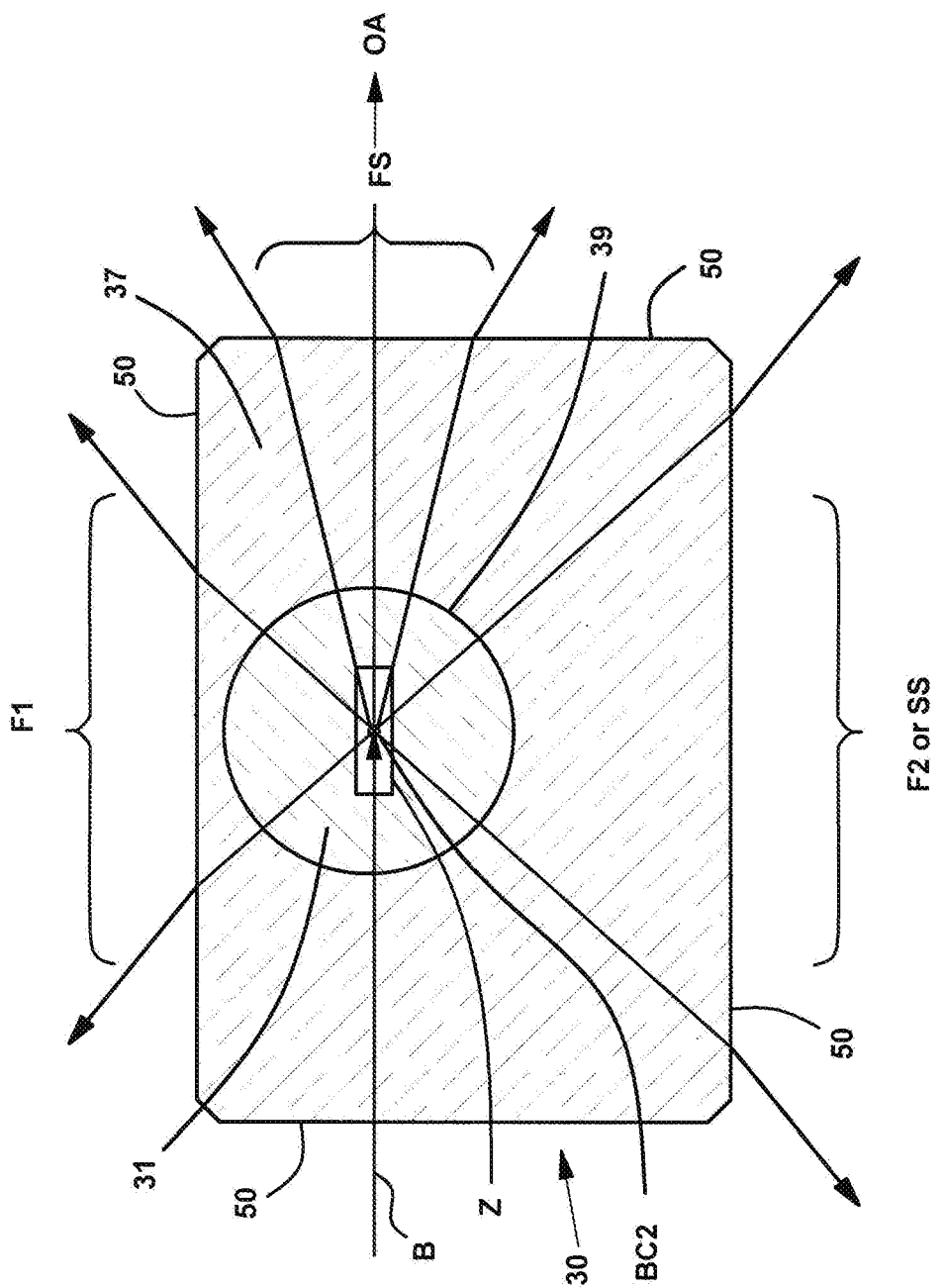
Figure 15:
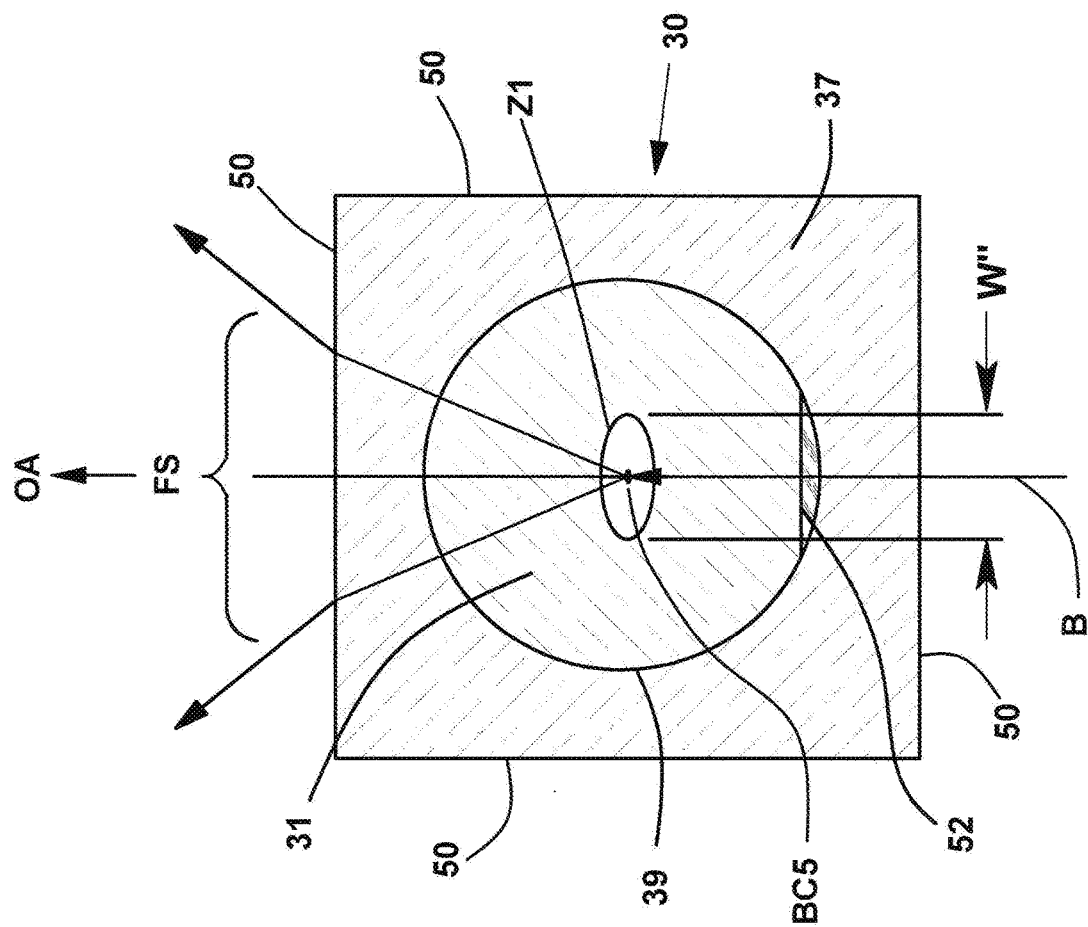

FIGS. 13A-13C, 14, and 15 illustrate other exemplary flow cells that illustrate other properties of flows cells within the scope of the invention. In FIGS. 13C, 14, and 15 appear cross-sectional views through the particle-sensing zone Z of various flow cells; such views are equally representative of flow cells having a uniform passageway for acquisition of purely optical characterizing parameters (e.g., in FIGS. 7A, 7B, and 13A); an hour-glass shaped passageway comprising a Coulter volumeter conduit (e.g., in FIGS. 4, 5, 9, and 13B); or a similar passageway comprising a jetting aperture for formed-body sorting (e.g., in FIG. 12). Such flow cells are suitable for instrumentation analogous to that illustrated in FIG. 3 or 11, to which in view of foregoing discussion they may be straightforwardly adapted by those skilled in the flow-cytometric art.

All flow cells described hereto have prismatic parameter-acquisition zones within an envelope having external surfaces parallel thereto so as to form windows of substantially uniform thickness through which cytometric parameters may be acquired of formed bodies transiting the particle-sensing portion within the flow-cell passageway. As discussed in the introductory portion hereof, such windows avoid non-axisymmetric refraction, but rays originating near the flow-cell axis will be refracted away from the surface normal at their incidence on the envelope surface ($\sin \theta_2 \approx 1.457 \sin \theta_1$), so producing a refractive increase in the effective angular aperture at the silica/air interface for light exiting the flow cell. FIGS. 13A-13C illustrate different aspects of flow cells 90 fabricated by providing a prismatic flow cell 31' with an envelope made by coring and fixing thereto a spherical solid 37' rather than cored prismatic solids as in foregoing examples of flow cells made by the method of the invention; element 37' is preferably fixed to element 31' at optical join 39 to be coaxial with prismatic passageway 32' in FIG. 13A or 32 in FIG. 13B. Preferably, flat 98 for coupling interrogating radiation into the sensing portion Z of such passageway is made as a reference flat parallel to the through-bore in element 37'. FIG. 13A is a perspective view of such a flow cell 90 suited for use in instrumentation relying solely on optical parameters for distinguishing types of formed bodies (e.g., that in FIG. 11). FIG. 13B illustrates an axial longitudinal section of a similar optical flow cell comprising a central volumeter conduit for simultaneous determination of both optical and Coulter V and/or C properties as in FIG. 3; made as was volumeter conduit Z in FIG. 4, passageway 32 comprises bores 54 from end surfaces 91 and transition surfaces of revolution 55 from bores to volumeter conduit Z. FIG. 13C is a transverse cross-section through the particle-sensing zone of the flow cell in FIG. 13A or 13B. Laser beam B enters flow cell 90 via flat 98 and interacts with formed bodies (e.g., BC2) within particle-sensing zone Z. Light scattered from laser beam B by formed bodies (e.g., FS along optical axis OA or SS perpendicular thereto), or emitted from fluorescence moieties used to mark some population of formed body (e.g., F), will be slightly deviated (i.e., $\sin\theta_2 \approx 0.915 \sin\theta_1$) in an axisymmetric manner on crossing the planar surface of flow channel 32' in FIG. 13A or volumeter conduit Z of FIG. 13B, while both the amount and non-axisymmetry of refractive deviation at cylindrical join 39 depend on the approximation to optical homogeneity through it. However, at the spherical envelope formed by surface of revolution 97 in FIG. 13C, $\sin\theta_2 = \sin\theta_1 = 0$, and such light will not be refractively deviated on passing through the glass/air interface, whereas light similarly passing through an envelope comprising planar surfaces is refractively deviated according to the relatively large mismatch in refractive index 1.475/1.000) between silica and air as shown in FIGS. 6, 14, and 15. Consequently, flow cells such as 90 in FIGS. 13A and 13B offer greater collection efficiency for a given acceptance aperture of the sensing apparatus and so are especially advantageous where low light levels must be sensed.

All flow cells described hereto are implicitly regular in cross-section, and none apply significant rotational forces to asymmetric formed bodies in sample flows. FIG. 14 is illustrative of flow cells 30 comprising non-regular prismatic flow channels capable of so acting to preferentially orient such formed bodies through the interrogation beam within the parameter-acquisition zone. Such flow cells are useful in instrumentation that relies solely on optical properties of formed bodies to differentiate subpopulations. In such flow cells optical parameters are acquired from formed bodies (e.g. BC2) transiting a rectangular flow channel Z in element 31, located off-center within conjoined element 37 but having preferably all optical surfaces 50 of the latter aligned parallel to corresponding surfaces of Z prior to formation of optical join 39. The thin window of flow cell 30, i.e., through which F1 is exiting, permits collection of fluorescence radiation excited by laser beam B with smaller and less-costly collection optics (e.g., lens 51 in FIG. 3) than needed with typical flow-cell wall thicknesses. Forward scatter (FS) signals along optical axis OA or other optical parameters, e.g., a second fluorescence (F2) signal or a side-scatter (SS) signal, may be acquired in the conventional manner through walls of typical thickness. Monolithic flow cells according to the '187 patent have been fabricated from prismatic flow cells having channels 320 by 140 micra, i.e., of aspect ratio approximately 2.3, and a diameter permitting a machined envelope comprising sides of width 5.0 mm prior to formation of said thin window; while such monolithic flow cells avoid the disadvantages of composite flow cells, the aspect ratio needed in the rectangular channel leads to unpredictable curvature in the longer channel surfaces of the drawn prismatic flow cells and, thus, to unpredictable non-axisymmetric refractive effects in both interrogation beam and resultant optical parameters. As noted in preceding portions of the present description, the fewer oversleeving steps required to form FIG. 14 cylindrical monolithic element 31 not only reduces the probability of wall flatness being lost during preform fabrication, but also facilitates better control over wall flatness during the cooler drawing process enabled by the smaller preform diameters required. It has been found that opposing passageway wall surfaces of major width about 300 micra, continuous with substantially flat opposing wall surfaces about 130 micra in width, may be produced with improved flatness in prismatic flow cells of a smaller diameter (e.g., about 1.5 mm) suitable as element 31 in FIG. 14 flow cell 30. The two major opposing wall surfaces of parameter-acquisition zone Z also facilitate alignment thereof to corresponding envelope optical surfaces 50, thereby minimizing need for flat 52 as shown for flow cells in FIGS. 4, 6, 7, and 10. It will be understood that radiation beam B may be coupled through flow cell 30 in a direction perpendicular to that shown in FIG. 14; alternatively, element 31 may be rotated 90° in element 37 therein. FIG. 14 flow cell 30 may be further processed into flow cell 30 for use in the FIG. 3 instrumentation by modifying the passageway in element 31 to form a Coulter volumeter conduit as has been described; however, this significantly reduces the orienting effect on asymmetric formed bodies. It will also be understood that other flow-cell embodiments according to the invention may be analogously structured, e.g., to provide the functionality of flow cells having a triangular volumeter conduit and a thin transparent plate for an optical window as described in U.S. Patent Application 2007/0085997. Such flow cells may be formed by aligning and fixing the appropriate irregular four-sided prism to a cylindrical element comprising a triangular passageway of desired dimensions (e.g., having channel surfaces approximately 125 micra in width), then lapping the longer of the unequal prism sides to the desired window thickness; the resulting window would comprise a central area of more or less exposed cylindrical element contingent to opposing areas on the prism, the optical join between the two elements being exposed to the environment, but not to passageway contents.

As noted in the introductory portion hereof, it is preferable that non-axisymmetric refractive effects be minimized at the envelope surface of optical flow cells and most preferable that such effects be minimized at surfaces of both the external envelope and sensing portion of the internal passageway. Flow cells 30 of FIGS. 4 and 14, 30' of FIGS. 7A and 7B, 30" of FIG. 9, and 90 of FIGS. 13A and 13B are of the most-preferable type, but other embodiments also fall within the scope of the invention. FIG. 15 illustrates such flow cells 30 in which parameter-acquisition zone Z1 in element 31 has an elliptical (i.e., oval) cross-section of major diameter W'" and is assembled within and aligned via flat 52 with a four-sided prismatic element 37 so that at least one optical surface 50 thereof is parallel to the major diameter of Z1 prior to formation of optical bond 39. As for the rectangular flow channel in FIG. 14 prismatic flow cell 31, such non-circular flow channels exert a rotational force on asymmetric formed bodies (e.g., BC5) so as to preferentially orient them in a sample stream; such channels may be provided by the same glass-forming process used to make the prismatic flow cells hereto discussed as element 31, 31' or 31" in the several figures, i.e., according to discussion of FIGS. 8A and 8B with use of an elliptical mandrel with respect to which flat 52 is appropriately formed. Such axially extending rectilinear channels having a cross-sectional aspect ratio, i.e., of major to minor diameters, of approximately 2.5 may be so produced; practicality of experimental flow cells having channel dimensions of 105×240 micra has been demonstrated. As indicated in discussion of FIG. 13 flow cell 90, for aforesaid flow cells 30, 30', or 30" having prismatic envelopes, refraction at the glass/air interface predominates, with non-axisymmetric refraction being minimized via parallel planar surfaces of the envelope and prismatic passageway 32, 32', or 32"; for such windows the liquid/glass interface of parameter-acquisition zone Z makes little contribution to refraction through the flow-cell wall. In contrast, refraction at the glass/air interface of flow cell 90 is minimized by the spherical flow-cell envelope, and refraction at the liquid/glass interface of Z preferably predominates, with non-axisymmetric refraction being minimized via a prismatic flow channel as for flow cells 30, 30' or 30". However, FIG. 15 flow cell 30 differs from the latter flow cells in having a parameter-acquisition zone Z1 within its flow passageway that is non-prismatic. As suggested in discussion of FIG. 14 flow cell 30, curvature of the surface of parameter-acquisition zone Z1 causes non-axisymmetric refraction affecting optical parameters resulting from interrogating laser beam B; in the plane perpendicular to the flow axis and containing the optical axis OA, such refraction is inversely proportionally to the radius of the osculating circle tangent to the surface of Z at the point through which the optical axis OA passes. Thus, due to the osculating circle of large radius at such point in FIG. 15, optical parameters acquired on or near optical axis OA in FIG. 15 may have non-axisymmetric refraction acceptable in a number of cytometric applications, particularly given better control of channel geometry attainable via the cooler drawing process by which element 31 may be produced. Moreover, purely optical analysis of cytometric samples containing asymmetric formed bodies may benefit more from the advantageous orienting forces applied to said bodies than suffer from the effects of such non-axisymmetric refraction; because such refraction in FIG. 15 flow cell 30 is relatively insensitive to wedge angle a of FIG. 6, some cytometric applications may benefit from elimination of optical join 39 therein, i.e., by providing a larger element 31 the machined integral envelope of a truly monolithic flow cell rather than an independent alignable envelope via element 37. Less preferably, but of potential value for use in lower-cost instruments, Z1 may have a cross-section of aspect ratio equal to 1.0, i.e., be circular rather than elliptical as illustrated in FIG. 15; cylindrical monolithic elements for use in flow cells of such low aspect ratios may be produced without use of the mandrel required for element 31 of FIG. 15 and are insensitive to rotation of element 37 during assembly and joining. If preferred, FIG. 15 flow cell 30 of any channel cross-sectional aspect ratio may be further processed into a flow cell for use in instrumentation analogous to that in FIG. 3, by modifying the passageway in element 31 to form a Coulter volumeter conduit as has been described.

A variety of cytometric instrumentation, whether acquiring only optical characterizing parameters as in FIG. 11 or acquiring both optical and Coulter characterizing parameters as in FIG. 3, may benefit from inclusion of other flow-cell embodiments fabricated in various configurations producible via the method of the invention. Such flow cells may have either more or less windows than comprised in the aforesaid examples, i.e., flow cells having similar aligned polygonal cross-sections through the parameter-acquisition portion of their sample passageways and their envelopes as described above but having, e.g., three, five, seven, or more windows arranged as may suit a particular cytometric application; said polygonal cross-sections need not be regular. Such flow cells may comprise elements made of glasses other than a form of silica, two or more elements made of different glass types, an optical-joining material chosen to minimize refractive mismatch through the optical joins, or such a material chosen to optimize a non-optical property of the aligned and fixed flow-cell components. Nor must envelopes of flow cells fabricated by the method of the invention be annularly complete so as to circumferentially enclose the cylindrical monolithic element, nor must such conforming elements be used singly, i.e., portions of two or more annular conforming elements of different materials or sections (longitudinal and/or transverse) may be used with a given cylindrical monolithic element as might be required to meet a specific cytometric application. It is understood that flow cells may be made by the method of the invention that comprise cylindrical monolithic elements having non-prismatic passageways, including those of circular cross-section; such flow cells refract non-axisymmetrically at the curved surface of the parameter-acquisition zone in their passageways, but are serviceable in instrument embodiments useful in less-demanding cytometric applications.

Preforms made and drawn as described above, but comprising fewer oversleeves and having a smaller outer diameter after the drawing process, provide advantages when adapted to other uses in instrumentation illustrated in FIG. 3 or 11. Such preforms need be neither optically transparent nor insulative and may be formed in glasses other than silica which, however, is preferable. For example, transducer assemblies in the latter figures rely on a sample inlet tube (e.g., FIG. 3 introduction tube 56) to inject prepared samples into sheath liquid S1 in the chamber of cap element 34 for passage through respective parameter-acquisition zone Z or Z" of flow cell 30 or 30". Such tubes are conventionally made of commercial tubing, tolerances on the channel of which cause unit-to-unit variability of sample flows through such parameter-acquisition zones (upper portion of Table 2). It has been found possible via the above-described glass-forming methods to significantly improve control over the dimensions of passageways through cylindrical monolithic elements; as a result of work leading hereto, production flow cells according to the '187 patent have such dimensions toleranced at ±2 micra (±0.000079 inch). Similar tolerances on flow channels in sample inlet tubes significantly reduce unit-to-unit variability in sample volumetric flow rates through parameter-acquisition zones. Prototype sample inlet tubes were fabricated from preforms made to have a flow-channel aspect ratio of 1.0 as described regarding FIG. 15, a post-draw channel ID of (0.00516±0.0005) inch, and an outer diameter (OD) of (0.061±0.0004) inch; segments cut to a length of (0.575±0.005) inch so as to have ends perpendicular to the channel axis and be chip-free about the channel edge were provided a conical frustum tapering at an angle of (22.5±2.5°) to a minor diameter of (0.020±0.003) inch at the exit end. Sealingly mounted in cap element 34 in FIG. 3 or 11 and fluidically coupled to port P1, such tubes reduce variability in volumetric sample flows through respective parameter-acquisition zone Z or Z" of flow cells 30 or 30" by about 80% (lower portion of Table 2). Such sample introduction tubes facilitate greater stability in both the diameter and spatial position of the sample core in hydrodynamically focused flow, thereby reducing coefficients of variation in characterizing parameters acquired via the interaction of formed bodies with an interrogating radiation beam of Gaussian profile. For some applications it may be advantageous to combine the functions of inlet tube 56 and port P1 into a single tubular inlet component 56/P1, i.e., inlet tube 56 itself serves as the connecting element whereby prepared sample flows are fluidically coupled into the chamber in cap element 34. In such cases a small, non-critical bevel on the OD of the entry end is advantageous. Such multi-function inlet tubes can also provide the volumetric-flow regulation of those single-purpose ones described here.

Table 2. Comparison of inlet tubes made from commercial tubing and from silica preforms drawn as described in this application, both having the geometry described in the accompanying text and a cylindrical channel length of (0.575±0.005) inch. The ID variation of the drawn inlet tube is 16% of that for the inlet tube made from commercial tubing; variation in sample volumetric flow rate at a pressure differential of 9.0 psi (pounds per square inch) is thereby reduced to 19.4% of that seen with inlet tubes made from commercial tubing.

| Inlet Tube 56 | | ID tolerance | ID, inch | Flow, μl/sec |
|---|---|---|---|---|
| Commercial tubing | | Maximum | 0.00550 | 31.081 |
| | | Nominal | 0.00500 | 21.044 |
| | | Minimum | 0.00450 | 13.688 |
| | Total allowed variation | | 0.00100 | 17.393 |
| Drawn silica preform | | Maximum | 0.00524 | 25.608 |
| | | Nominal | 0.00516 | 23.870 |
| | | Minimum | 0.00508 | 22.230 |
| | Total allowed variation | | 0.00016 | 3.378 |

It was noted regarding flow cells illustrated in FIGS. 14 and 15 that some non-circular flow channels exert an orienting rotational force on asymmetric formed bodies so as to preferentially orient them in a sample stream. The probability of an asymmetric formed body, e.g., an erythrocyte, passing through the center of parameter-acquisition zone Z of FIG. 3 flow cell 30 or FIG. 11 flow cell 30″ in a particular orientation with respect to the interrogating beam B, e.g., with a discoid face perpendicular to said beam, follows a uniform distribution that depends on the acceptable tolerance for such spatial relation, i.e., if such tolerance be ±10° for the discoid face being truly perpendicular to such beam, then the probability is (20°/360°), or 5.5%, that a particular such orientation will occur. For experimental flow-cell elements 31 having the rectangular or elliptical passageways of FIG. 14 or 15 about 12-mm length, approximately 17% of erythrocytes were rotated within ±10° of perpendicularity to the optical axis of interrogating laser beam B when said beam traversed the minor dimension of the respective flow channels. This result indicates a 68% reduction in the randomness of erythrocyte orientation about the flow axis; via reduction in the coefficients of variation of optical characterizing parameters, such improved orientation of asymmetric formed bodies offers advantages in a great number of cytometric applications and may be readily attained in flow cells fabricated by the method of the present invention. For FIG. 3 inlet tube 56 discussed above, no such orienting force is applied, and the probability of an asymmetric formed body, e.g., an erythrocyte, exiting it and passing through the center of a circular or non-regular prismatic parameter-acquisition zone Z of a flow cell within ±10° of such specific orientation is also about 5.5%.

Random orientation of asymmetric formed bodies about the flow axis results in increased coefficients of variation in their acquired optical characterizing parameters. The probability of such a formed body transiting the parameter-acquisition zone Z of a flow cell in a preferred orientation may be significantly increased, while retaining improved control of volumetric sample flows, via geometric modifications to aforesaid inlet tube 56. Such improvements apply a rotating force to asymmetric formed bodies in such sample flows so that a greater number thereof pass seriatim through the parameter-acquisition zone of a flow cell in a preferred orientation. Thus, in addition to regulating sample volumetric flows through parameter-acquisition zones, sample inlet tubes comprising such improvements preferentially orient non-axisymmetric formed bodies in such flows during their passage through such zones. These combined improvements are gained independently of the cross-section of the parameter-acquisition zone in the flow cell and, with appropriate alignment with such zones comprising cross-sections of sufficient non-unity aspect ratio, such inlet tubes may be caused to interact synergistically with orienting forces originating in flow passageways having non-unity aspect ratios, e.g., the rectangular or elliptical parameter zones Z or Z1 of flow cells 30 in FIG. 14 or 15. Such synergistic interaction can further reduce randomness in the presentation of asymmetric formed bodies to the interrogating radiation beam, thereby further decreasing coefficients of variation in optical characterizing parameters thereof acquired with transducer assemblies comprising both inlet tubes and flow cells having flow passageways having cross-sections of non-unity aspect ratio.

Respective FIGS. 16A and 16B illustrate inlet tubes 100 and 100' fabricated from preforms made and drawn according to the methods described above, but for which opposing polished inclined flats 102 or 102' have been substituted for the conical frustum discussed regarding FIG. 3 inlet tube 56. The dimensions of flow channel 108 or 108' may be adapted to the needs of a cytometric application as is known in the flow-restrictor art. The residual of cylindrical surface 106 or 106' extends to the exit tip 104 or 104', and it will be understood that said flats are symmetric about the axis of inlet tubes 100 or 100'. Flats 102 or 102' are formed at an angle with respect to the tube axis between 20° and 25°; for sheath flow rates used in instrumentation such as is illustrated in FIG. 3, said angle is most preferably about 22.5°, whereas an angle of about 21° is more preferable at higher sheath flow rates, e.g., such as typically used in instrumentation illustrated in FIG. 11. All other geometrical details and dimensions are as discussed for FIG. 3 inlet tube 56. Inlet tubes 100 and 100' are sealingly mounted in cap element 34 of respective FIG. 3 or 11 and fluidically coupled to port P1, flats 104 or 104' being positioned to apply fluidic orienting forces to asymmetric formed bodies so as to rotate them about the axis of channel 108 or 108' into a preferred spatial relationship to the interrogating radiation beam B, e.g., if it is preferred that erythrocytes pass through such beam with a discoid face perpendicular to the beam, the long edge of said flats should be perpendicular to the beam. In FIG. 16A channel 108 is cylindrical and surfaces through flat 104 as a circular exit; about 44% of erythrocytes emerging from such exits could be oriented with a discoid face perpendicular within approximately ±10° to interrogating beam B when such experimental inlet tubes were substituted in instrumentation otherwise analogous to that illustrated in FIG. 3, i.e., approximately eight times as many as expected to be so oriented with the comparative inlet tube having the exit tip shaped as the conical frustum described above. For inlet tips having the exit flat 104' reduced to the minimum thickness permitted by detrimental chipping, about ten times as many such erythrocytes were so oriented as with inlet tubes having the aforesaid conical frustum; flats 102', so made, intersect and partially remove the channel wall of such inlet tubes at the tube exit, e.g., as illustrated for rectangular channel 108' in FIG. 16B. For optimum orientation of asymmetric formed bodies, flats 102 or 102' should be symmetric about the channel axis, and the edges of such flats and tip 104 or 104' should be chip-free. Aforesaid inlet tubes having tips of either geometry and being chip-free at the exit edge of channel 108 or 108' provided repeatable reduction of variability in sample volumetric flow rates as noted above.

Inlet tubes may also be fabricated from preforms made as described for flow cells discussed in connection with FIG. 14, except only comprise one or two oversleeves so as to form a drawn cylindrical monolithic element (i.e., a prismatic flow cell) having a suitable outer diameter. Experimental inlet tubes, made from such preforms and provided a conical frustum at the exit end as described above, oriented an estimated 24% of erythrocytes within ±10° of perpendicularity to an interrogating laser beam B when prototype inlet tubes were tested in instrumentation otherwise analogous to that illustrated in FIG. 11. Other experimental inlet tubes likewise made, but having a uniform elliptical channel as discussed regarding FIG. 15, oriented an estimated 27% of erythrocytes when similarly tested. However, experimental inlet tubes having either such rectangular or elliptical channels oriented approximately 57% of erythrocytes when the tube exit tips were flatted as illustrated in FIG. 16A, but about 62% of such formed bodies when the tube exit tips were flatted to minimum thickness as illustrated in FIG. 16B. Flats 102 or 102' being symmetrical and all tip edges being chip-free are crucial to repeatable orientation of the asymmetric erythrocytes. Acceptable inlet tubes having either of the aforesaid tip geometries provided the expected reduction of variability in sample volumetric flow rates.

Figure 17:
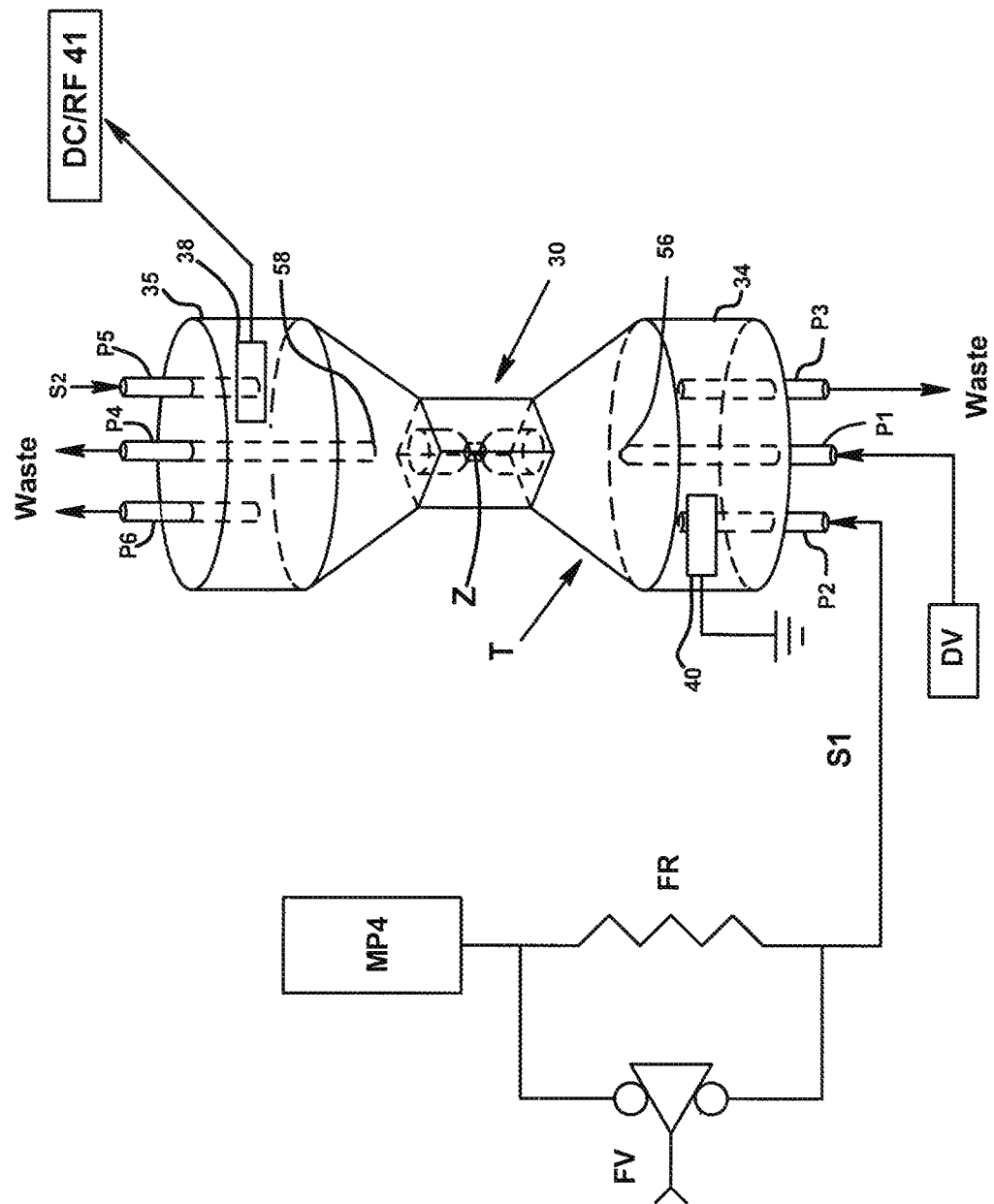
FIG. 17 is a schematic illustration of a cytometric transducer assembly, the sample and sheath flows through the flow cell of which are regulated by sample introduction and sheath restrictor tubes according to the invention.
Figure 18A:
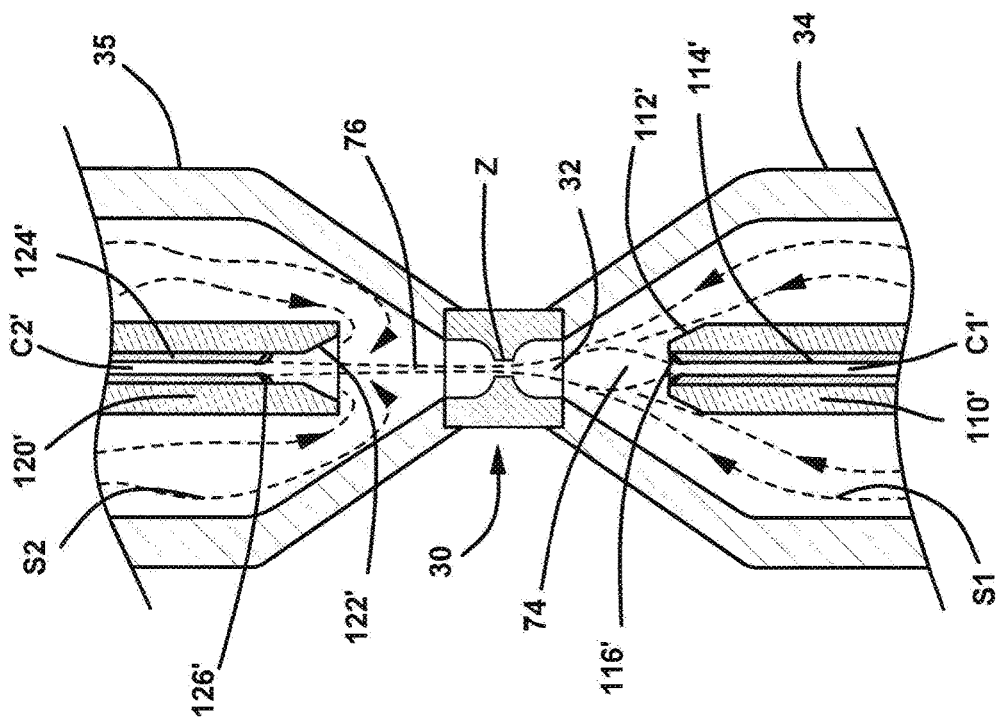
FIGS. 18A and 18B illustrate sample introduction and exit tubes for use in transducer assemblies, said tubes comprising electrode elements for acquisition of Coulter volume (V) and/or conductivity (C) characterizing parameters of formed bodies passing through the parameter-acquisition zone of a flow cell.
Figure 18B:
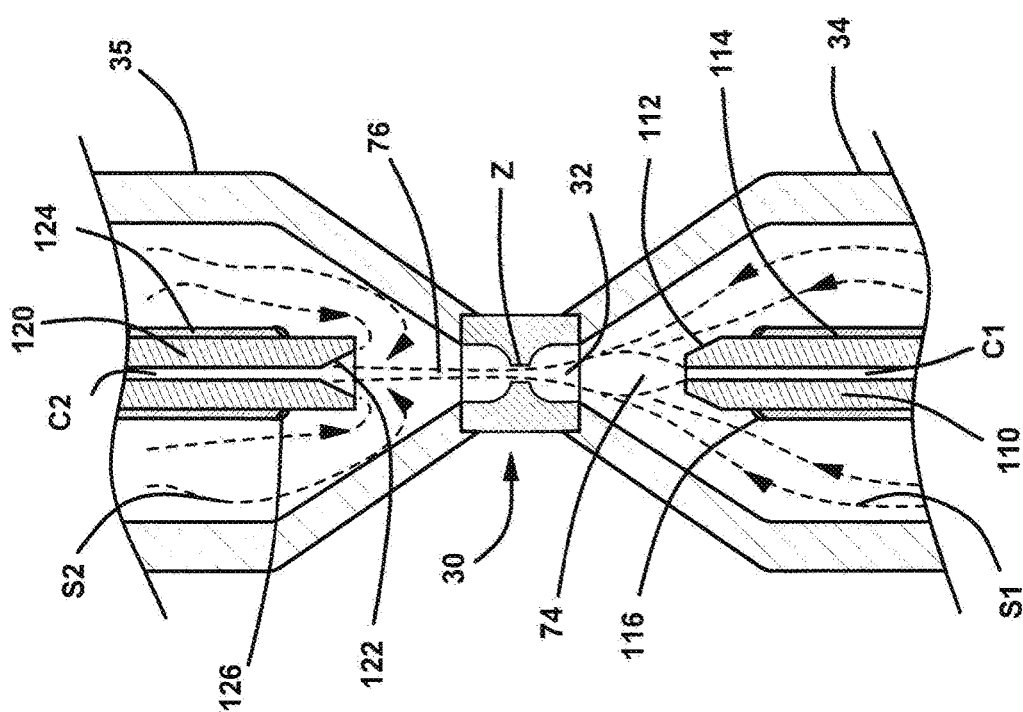

To illustrate still other forms of inlet tubes, FIGS. 17, 18A, and 18B isolate the portion of FIG. 3 transducer assembly T that is contiguous to flow cell 30; references therein like those in previous figures indicate like parts. As has been discussed, Coulter V and/or C characterizing parameters are acquired via FIG. 17 electrode 40 in the chamber of cap element 34, electrode 38 in the chamber of cap element 35, and DC/RF circuitry 41 to which both said electrodes are operatively connected. In FIGS. 18A and 18B, respective inlet tubes 110 or 110' bear cylindrical conductive elements 114 or 114' which are fluidly contacted and operatively connected to FIG. 17 DC/RF circuitry to function as electrode 40, while respective exit tubes 120 or 120' bear cylindrical conductive elements 124 or 124' similarly contacted and connected to function as FIG. 17 electrode 38. Such conductive elements may be any preferred form of the many forms known in electrode art, e.g., palladium tubing of appropriate dimensions bonded to the fluidic tubes, platinum foil appropriately applied, or conductive emulsion fired there onto. The dual-function structures 110/114 and 120/124 illustrated in FIG. 18A provide better volumetric flow regulation through parameter-acquisition zone Z of flow cell 30 and so are preferred; however, the electric-field configuration provided by the analogous structures in FIG. 18B may be advantageous in some cytometric applications. With either the structure of FIG. 18A or 18B, prepared sample from FIG. 17 distribution valve DV enters transducer assembly T via port P1, which is fluidically coupled to the inlet tube, e.g., inlet tubes 110 or 110' in FIG. 18A or 18B. Inlet tube 110 or 110' injects prepared sample 74 from channel C1 or C1' into sheath liquid S1 in the chamber in cap element 34, and hydrodynamically focused flow carries the formed bodies therein through parameter-acquisition zone Z in passageway 32 of flow cell 30 as has been described. The composite flow 74 from sensing zone Z enters sheath liquid S2 in the chamber in cap element 35, is entrained in the sheath liquid, enters channel C2 or C2' in exit tube 120 or 120', and exits the transducer assembly through FIG. 17 port P4 to waste as has been described. The internal flow pattern just summarized is facilitated by the conical frustum 122 or 122' on inlet tubes 110 or 110', which acts to keep sheath flow from separating at the tube tip, and by the conical recess 122 or 122' in the tip of exit tubes 120 or 120', which acts to guide flow into channel C2 or C2'. Inlet tube 110 in FIG. 18A may be as described regarding Table 2, above, or one of the ones described regarding FIGS. 16A-16B and orienting inlet tubes; it is preferable that inlet tube 110' in FIG. 18B be geometrically similar to inlet tube 110, but having a channel compatible with the desired conductive element 114' and any required bonding clearance. The geometry and dimensions of exit tubes 120 or 120' are less critical than for inlet tubes 110 or 110'. To avoid interference by electrolytic bubble generation at the end of conductive element 114 or 114' and 124 or 124', it is important that such ends be insulated by a bead of insulative material 116 or 116' and 126 or 126'. Transducer assemblies T comprising structures combining fluidic/electrode functions as herein described are more readily assembled and provide Coulter V and/or C characterizing parameters of formed bodies that equal or exceed in quality those provided by conventional separate functional components.

A preferred method for differentiating formed bodies in a liquid suspension using sample introduction (or inlet) tubes of the invention comprises the steps of: a) providing a sample introduction (or inlet) tube of the type described herein that comprises a flow channel applying a rotational force to asymmetric formed bodies in such liquid suspensions; b) positioning and fixing such sample inlet tube in said transducer assembly relative to the optical axis of an interrogating beam so that asymmetric formed bodies in such liquid suspensions are preferentially oriented relative to said optical axis; c) passing such liquid suspensions through a parameter-acquisition portion of the flow passageway in an optical flow cell while irradiating formed bodies therein with a beam of radiation passing through one wall of said flow cell; and d) detecting different optical parameters of the irradiated formed bodies through other of such walls. Preferably, the flow channel in such sample inlet tube is uniformly rectangular or elliptical in cross-section. Such flow cell preferably has at least three discrete walls (or windows) through two of which differentiating optical parameters of formed bodies in the parameter-acquisition zone can be sensed and, upon irradiating formed bodies therein with a beam of radiation passing through a first wall, forward-scatter radiation from the irradiated formed bodies may be sensed through a second wall and fluorescence characteristics of the irradiated formed bodies may be sensed through a third wall. For cytometric applications involving low-intensity optical signals, a second element having an envelope comprising a non-cylindrical surface of revolution, e.g., a spherical surface, is highly preferable. Most preferably, at least some of the aforesaid optical measurements are combined with Coulter volume V and/or conductivity C measurements simultaneously made on the irradiated formed bodies passing seriatim through the flow channel. Such differentiating parameters are correlated by conventional algorithms to provide desired diagnostic information.

From the foregoing description, it will be appreciated that a new and improved optical flow cell has been provided.

Being comprised of cylindrical monolithic elements offering better control over channel geometry and independent alignable elements having a preferred optical envelope, all of the above-noted disadvantages of glass-forming and machining processes used to fabricate monolithic optical flow cells are minimized as indicated in Table 1 and yields of acceptable flow cells may be increased, thereby reducing costs and selection processes during assembly of acceptable flow cells into transducer assemblies. Further, the method of manufacture used to provide the exemplary flow cells is generally applicable to manufacture of a broad variety of optical flow-cell embodiments. It will also be appreciated that glass-forming methods herein described for fabrication of such cylindrical monolithic elements have been adapted to provide sample introduction (or inlet) tubes that reduce variability in sample volumetric flows through the parameter-acquisition zone of optical flow cells, thereby enabling simplification in fluidic systems supporting sample delivery to optical flow cells that is of commercial value.

The improved volumetric flow control provided by the above-described drawn elements also has other advantageous applications in instrumentation such as illustrated in FIGS. 3 and 11. With reference to FIG. 17, wherein FIG. 3 transducer assembly T is isolated together with metering pump MP4 for sheath liquid S1, flow restrictor FR provides an exemplar; in said figures like reference characters denote like parts. During sample analysis, metering pump MP4 must provide port P2 a controlled volume of sheath liquid S1 determined by the volumetric sample flow from distribution valve DV through port P1 and inlet tube 56; this is done with flush valve FV open so that the flow of sheath liquid S1 is regulated by flow restrictor FR. However, metering pump MP4 must be able to provide a significantly greater flow of sheath liquid S1 during the post-analysis flush required to clear the chamber in cap element 34 of the sample just analyzed; flush valve FV is then opened to bypass flow restrictor FR. A conventional flow restrictor is a segment of commercial polyetheretherketone (PEEK) cylindrical tubing having a channel ID of (0.016±0.001) inch and a length of (4.75±0.04) inch; the flow properties are given in the upper portion of Table 3; the lower portion of Table 3 contains similar data for experimental flow restrictors FR fabricated from a drawn cylindrical monolithic element as described above to have a cylindrical channel ID of (0.012±0.00016) inch and length of (1.500±0.005) inch. In addition to the less-intrusive physical size, such flow restrictors FR reduce the variability in volumetric sheath flow to about one-fifth of that seen with the conventional flow restrictor. It will be appreciated that such flow restrictors FR may be used to balance sample and sheath volumetric flow rates in hydrodynamically focused flow through the parameter-acquisition zone Z or Z" in FIG. 3 or 11, so advantageously providing both improved control of total flow through the parameter-acquisition zone and the dynamic behavior of the supporting fluidic systems. Furthermore, some applications of instrumentation illustrated in FIGS. 3 and 11 may benefit if cylindrical exit tube 58 is fabricated from an appropriate cylindrical monolithic element made by the methods herein described.

Table 3. Comparison of conventional sheath flow restrictors made from commercial PEEK tubing and from silica preforms drawn as described in this application. The ID variation of the drawn restrictor tube is 16% of that for the restrictor tube made from the commercial tubing; variation in sheath volumetric flow rate at a pressure differential of 8.0 psi (pounds per square inch) is thereby reduced to 21.9% of that seen with inlet tubes made from the commercial tubing.

| Sheath Flow Restrictor FR | ID tolerance | ID, inch | Flow, μl/sec |
|---|---|---|---|
| | Maximum | 0.017 | 413.53 |
| Commercial PEEK tubing | Nominal | 0.016 | 321.75 |
| | Minimum | 0.015 | 246.47 |
| Total allowed variation | | 0.002 | 167.06 |
| | Maximum | 0.01216 | 341.05 |
| Drawn silica preform | Nominal | 0.01200 | 328.38 |
| | Minimum | 0.01184 | 304.51 |
| Total allowed variation | | 0.00032 | 36.54 |

The multiple improvements in methods and components herein described may be comprised, singly or in combination, in cytometric instrumentation to provide improved function while at the same time reducing costs during fabrication of components and assembly thereof. For example, instrumentation illustrated in FIG. 3 or 11 comprises in transducer assembly T or T' only a flow cell 30 or 30" according to the invention, but an improved inlet tube structured and fabricated in accordance with the present invention as described regarding Table 2 or FIGS. 16A and 16B may be substituted for inlet tube 56 in transducer assembly T or T'; alternatively, such improved inlet tube may be used with a prior-art optical flow cell substituted for a flow cell 30 or 30" in transducer assembly T or T'. Similarly, structures combining fluidic and electrode functions such as described regarding FIGS. 18A and 18B may be used alone in T or T' or with any of the aforesaid combinations of components of the invention. Further, an improved flow restrictor such as described regarding Table 3 and FIG. 17 may be beneficial when used alone in metering mechanism 16 or 16' in the instrumentation illustrated in respective FIG. 3 or 11, when used in other instrumentation analogous thereto with an improved transducer assembly T or T' comprising either the flow cell or inlet tube of the invention, or when used in yet other instrumentation with an improved transducer assembly T or T' comprising both the flow cell and inlet tube of the invention. Finally, back reflections from the entry face of the flow cell 30 or 30" used in T or T' in any of the aforesaid embodiments potentially may cause instability in interrogating laser beam B; such eventually may be avoided by rotating the transducer assembly in its supporting structure (not shown in FIG. 3 or 11) during assembly so that a perpendicular to the face of such flow cells through which the laser beam enters is approximately offset one degree (1°) left or right of the optical axis of the laser or, less preferably, by causing the transducer assembly T or T' to tilt so that such perpendicular is offset approximately one degree (1°) above or below the said axis. Other combinations of improved methods and components according to the present invention will be apparent to those skilled in the cytometric art.

A preferred method for differentiating formed bodies in a liquid suspension using transducer assemblies of the invention comprises the steps of: a) providing a flow cell of the type described herein that comprises at least two elements made of an insulative transparent material, the first element being a substantially cylindrical monolithic element that includes a seamless internal flow passageway at least an axial portion of which is surrounded by a continuous surface of preferably non-circular cross-section and the second element having both a concave surface conformed to such first element and an external non-cylindrical optical envelope of predetermined form and orientation, said second element being fixed to said first element by an optical join so as to minimize non-axisymmetric refractive effects in optical signals acquired through at least three compound walls (or windows) between corresponding surfaces of said passageway and said envelope through which optical characterizing parameters resulting from interaction of said formed bodies with an interrogating radiation beam may be acquired; b) providing a sample introduction (or inlet) tube of the type described herein that comprises a flow channel applying a rotational force to asymmetric formed bodies in such liquid suspensions; c) positioning and fixing such flow cell and/or such sample inlet tube, singly or in combination, in said transducer assembly relative to the optical axis of an interrogating beam so that non-axisymmetric refractive effects on radiation passing through said walls are minimized and/or such asymmetric formed bodies are preferentially oriented relative to said optical axis; d) passing such liquid suspensions through a parameter-acquisition portion of the flow passageway while irradiating formed bodies therein with a beam of radiation passing through one of such walls; and e) detecting different optical parameters of the irradiated formed bodies through other of such walls. Preferably, the flow channel in such sample inlet tube is uniformly rectangular or elliptical in cross-section. Such flow cell preferably has at least three discrete walls (or windows) through two of which differentiating optical parameters of formed bodies in the parameter-acquisition zone can be sensed and, upon irradiating formed bodies therein with a beam of radiation passing through a first wall, forward-scatter radiation from the irradiated formed bodies may be sensed through a second wall and fluorescence characteristics of the irradiated formed bodies may be sensed through a third wall. For cytometric applications involving low-intensity optical signals, a second element having an envelope comprising a non-cylindrical surface of revolution, e.g., a spherical surface, is highly preferable. Most preferably, at least some of the aforesaid optical measurements are combined with Coulter volume V and/or conductivity C measurements simultaneously made on the irradiated formed bodies passing seriatim through the flow channel. Such differentiating parameters are correlated by conventional algorithms to provide desired diagnostic information.

The invention has been described in detail while making reference to a number of specific embodiments. It will be appreciated, however, that various changes and modifications beyond those herein discussed can be made without departing from the spirit of the invention and the scope literally defined by the appended claims. For example, all prismatic conforming second elements in preceding discussion of the new flow cells were illustrated as cored about their center of mass through an end surface, but flow cells fabricated by the method of the invention need not have either envelopes or parameter-acquisition axes symmetrical about their passageways, i.e., it is within the spirit of the invention that a cube of a preferred glass be cored corner-to-corner along a major diagonal to accept the cylindrical monolithic element, with a third corner appropriately flatted to provide an entry for an interrogating radiation beam, thereby providing six ports for out-of-plane acquisition of scatter and/or fluorescence characterizing parameters.

All patents, patent publications, patent applications, journal articles, books, technical references, and the like discussed in the instant disclosure are incorporated herein by reference in their entirety for all purposes.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. In certain cases, method steps or operations may be performed or executed in differing order, or operations may be added, deleted or modified. It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention. Accordingly, the present invention is not limited to the embodiments described above or depicted in the drawings, and various embodiments and modifications can be made without departing from the scope of the claims below.

What is claimed is:

1. A method for differentiating formed bodies by optical characterizing using a flow cell, comprising:
    a) providing a flow cell comprising at least first and second elements made of an insulative transparent material;
        the first element comprising a substantially cylindrical monolithic element that includes a seamless internal flow passageway comprising a parameter-acquisition zone, at least an axial portion of which is surrounded by a continuous surface of non-circular cross-section;
        the second element comprising (i) an internal concave surface conformed to the first element and (ii) an external non-cylindrical optical envelope of predetermined form and orientation, the second element fixed to said first element by an optical join;
    b) passing a liquid suspension through the parameter-acquisition zone of the internal flow passageway while irradiating formed bodies therein with a beam of radiation passing through at least a first wall of the parameter-acquisition zone; and
    c) detecting different optical parameters of the irradiated formed bodies through at least a second wall of the parameter-acquisition zone.

2. The method of claim 1, wherein the parameter-acquisition zone of the flow cell comprises at least three discrete walls functioning as windows.

3. The method of claim 2, wherein the differing optical parameters of the irradiated formed bodies are sensed through at least two of the walls.

4. The method of claim 2, further comprising:
    irradiating the formed bodies through the first wall;
    sensing forward-scatter radiation from the irradiated formed bodies through the second wall; and
    sensing fluorescence characteristics of the irradiated formed bodies through a third wall.

5. The method of claim 1, wherein the parameter-acquisition zone of the flow cell comprises at least five discrete walls functioning as windows.

6. The method of claim 5, wherein the differing optical parameters of the irradiated formed bodies are sensed through at least four of the walls.

7. The method of claim 5, further comprising:
    irradiating formed bodies through the first wall;
    sensing forward-scatter radiation from the irradiated formed bodies through the second wall;
    sensing back-scattered radiation from the irradiated formed bodies through the third wall;

sensing fluorescence characteristics of the irradiated formed bodies through the fourth wall; and sensing side-scattered radiation from the irradiated formed bodies through the fifth wall.

8. The method of claim 1, wherein the second element comprises an envelope comprising a non-cylindrical surface of revolution.

9. The method of claim 8, wherein the non-cylindrical surface is a spherical surface.

10. The method of claim 1, wherein the parameter-acquisition zone comprises a four-sided cross section.

11. The method of claim 1, further comprising combining optical measurements with Coulter volume (V) measurements, Coulter conductivity (C) measurements, or both, simultaneously made on the irradiated formed bodies passing through the internal flow channel.

12. The method of claim 1, wherein the at least a portion of the external envelope is non-cylindrical, through which various cytometric optical parameters may be derived of formed bodies passing through the flow channel.

13. The method of claim 1, wherein the seamless internal flow passageway of the first element comprises an hourglass shape.

14. The method of claim 1, wherein the parameter-acquisition zone comprises a constriction space with a reduced diameter.

15. The method of claim 14, wherein the reduced diameter comprises a channel width of 150 micra or less.

16. The method of claim 1, wherein the parameter-acquisition zone contains Coulter excitation currents within a joinless flow channel.

17. The method of claim 1, wherein the parameter-acquisition zone comprises a central volumeter conduit for simultaneous determination of both optical and Coulter V and/or Coulter C properties.

18. The method of claim 1, wherein an irradiating laser beam enters the flow cell through a flat surface of the second element and interacts with formed bodies in the parameter-acquisition zone.

* * * * *